(12) United States Patent
Doll et al.

(10) Patent No.: US 6,214,828 B1
(45) Date of Patent: Apr. 10, 2001

(54) TRICYCLIC AMIDES USEFUL FOR INHIBITION OF G-PROTEIN FUNCTION AND FOR TREATMENT OF PROLIFERATIVE DISEASE

(75) Inventors: Ronald J. Doll, Maplewood; Joseph M. Kelly, Parlin; Alan K. Mallams, Hackettstown; F. George Njoroge, Union; Stacy W. Remiszewski, Washington Township; Arthur G. Taveras, Rockaway, all of NJ (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 09/190,362

(22) Filed: Nov. 12, 1998

Related U.S. Application Data

(62) Division of application No. 08/766,601, filed on Dec. 12, 1996, now Pat. No. 5,874,442.
(60) Provisional application No. 60/013,350, filed on Mar. 13, 1996, and provisional application No. 60/009,180, filed on Dec. 22, 1995.

(51) Int. Cl.[7] ............... A61K 31/496; C07D 403/04; C07D 403/14; A61P 35/00
(52) U.S. Cl. ................. 514/253.03; 544/361
(58) Field of Search ............... 544/361; 514/254, 514/253.03

(56) References Cited

U.S. PATENT DOCUMENTS

| | | | |
|---|---|---|---|
| 4,144,337 | 3/1979 | Bastian | 514/254 |
| 4,282,233 | 8/1981 | Villani | 514/290 |
| 4,826,853 | 5/1989 | Piwinski et al. | 514/290 |
| 4,831,042 | 5/1989 | Villani | 514/316 |
| 4,863,931 | 9/1989 | Schumacher et al. | 514/290 |
| 5,089,496 | 2/1992 | Piwinski et al. | 514/253 |
| 5,104,876 | 4/1992 | Piwinski et al. | 514/254 |
| 5,141,851 | 8/1992 | Brown et al. | 435/15 |
| 5,151,423 | 9/1992 | Piwinski et al. | 514/290 |
| 5,185,248 | 2/1993 | Barbacid et al. | 435/15 |
| 5,204,348 | 4/1993 | Fukazawa et al. | 514/183 |
| 5,393,890 | 2/1995 | Syoji et al. | 546/80 |
| 5,405,843 | 4/1995 | Fukazawa et al. | 514/253 |

FOREIGN PATENT DOCUMENTS

| | | |
|---|---|---|
| 4243496 | 3/1994 | (DE) . |
| 0042544 | 12/1981 | (EP) . |
| 0270818 | 6/1988 | (EP) . |
| 0347123 | 12/1989 | (EP) . |
| 0363212 | 11/1990 | (EP) . |
| 0396083 | 11/1990 | (EP) . |
| 0495484 | 7/1992 | (EP) . |
| 0535730 | 4/1993 | (EP) . |
| WO88/03138 | 5/1988 | (WO) . |
| WO89/10363 | 11/1989 | (WO) . |
| WO90/13548 | 11/1990 | (WO) . |
| WO92/00293 | 1/1992 | (WO) . |
| WO92/11034 | 7/1992 | (WO) . |
| WO94/04561 | 3/1994 | (WO) . |
| WO94/05693 | 3/1994 | (WO) . |
| WO94/24107 | 10/1994 | (WO) . |
| WO95/00497 | 1/1995 | (WO) . |
| WO 95/10515 | 4/1995 | (WO) . |
| WO95/10516 | 4/1995 | (WO) . |
| WO 96/30018 | 10/1996 | (WO) . |
| WO 96/30363 | 10/1996 | (WO) . |
| WO 96/31478 | 10/1996 | (WO) . |

OTHER PUBLICATIONS

Cell, 65, 1–4 (1991).

J. Biol. Chem., 266, (24) 15575–15578 (1991).

Proc. Natl. Acad. Sci. USA, 87, 3042–3046 (1990).

Proc. Natl. Acad. Sci. USA, 88, 8631–8635 (1991).

Nature, 356, 713–715 (1992).

Proc. Natl. Acad. Sci. USA, 87, 7541–7545 (1990).

J. Biol. Chem., 265, (25) 14701–14704 (1990).

Proc. Natl. Acad. Sci. USA, 87, 7926–7929 (1990).

Cell, 62, 81–88 (1990).

Biochemistry, 31, 3800–3807 (1992).

Science, 260, 1934–1937.

Science, 260, 1937–1942.

Piwinski, et al., J. Med. Chem., 34, (1) 457–461 (1991).

Masci, J. Chem. Soc., Chem. Commun., 1262–1263 (1982).

Masci, J. Org. Chem., 50, 4081–4087 (1985).

Sebti, et al., Proc. Ann. Meeting AM Assoc. Cancer Res., 33:A2217 (1992).

Villani, et al., J. Med. Chem., 15, (7) 750–754 (1972).

Billah, et al., Lipids, 26 (12) 1172–1174 (1991).

Villani, et al., Arzneim.–Forsch/Drug Res., 36(II), 1311–1314 (1986).

Yokoyama et al, Proc. Natl. Acad. Sci. USA, 88, 5302–5306 (1991).

Omer et al, Biochemistry, 32, 5167–5176 (1993).

Furth et al, J. Virology, 43, 294–304 (1982).

Price et al, Proc. Natl. Acad. Sci. USA, 84, 156–160 (1987).

Khosravi–Far et al, Cell Growth & Differentiation, 3, 461–468 (1992).

Advanced Organic Chemistry, 3rd ed., Part B: Reactions and Synthesis (1990), 571–573.

Sarges, et al, J. Med. Chem., 33, 1859–1865 (1990).

Graham, Exp. Opin. Ther. Patents, 5, 1269–1285 (1995).

Sepp–Lorenzino et al, Cancer Res., 55, 5302–5309 (1995).

Nagasu et al, Cancer Res., 55, 5310–5314 (1995).

Chemical Abstracts, 121 (1994) 301326v.

Search Report for PCT/US96/19603 filed Dec. 19, 1996 (now WO 97/23478 published Jul. 3, 1997)—Applicants' Foreign counterpart of the above identified application.

US 6,214,828 B1
Page 2

*Primary Examiner*—Evelyn Mei Huang
(74) *Attorney, Agent, or Firm*—Henry C. Jeanette; Margaret M. Albanese

(57) ABSTRACT

Novel compounds, such as:

(1.0)

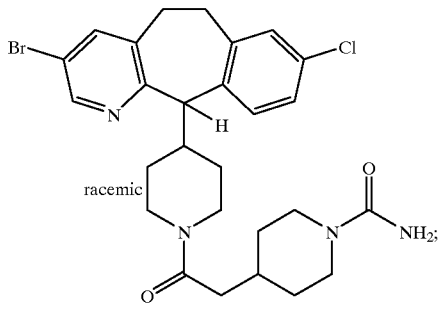

(4.0)

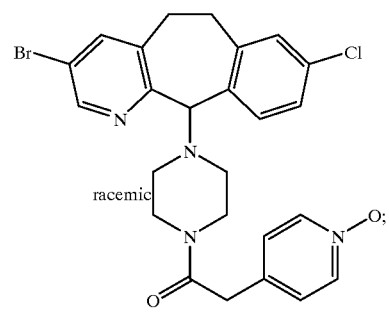

(22.0)

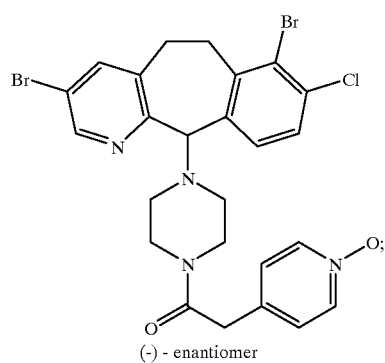

-continued (27.0)

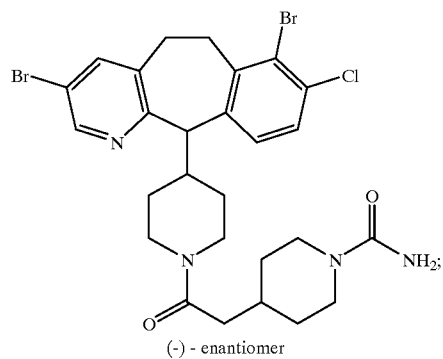

(32.0)

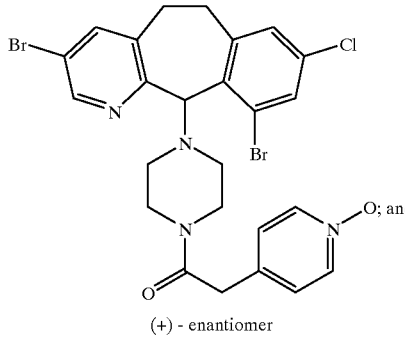

(39.0)

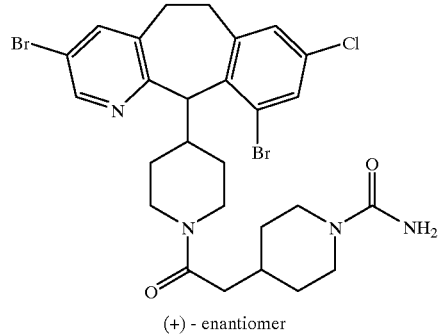

are disclosed. Also disclosed are methods for inhibiting the abnormal growth of cells, for inhibiting farnesyl protein transferase and for treating cancers using the novel compounds.

12 Claims, No Drawings

TRICYCLIC AMIDES USEFUL FOR INHIBITION OF G-PROTEIN FUNCTION AND FOR TREATMENT OF PROLIFERATIVE DISEASE

REFERENCE TO RELATED APPLICATIONS

This application is a divisional of application Ser. No. 08/766,601 filed Dec. 12, 1996, U.S. Pat. No. 5,874,442 which application claims the benefit of U.S. Provisional Application Ser. No. 60/013,350 filed Mar. 13, 1996, and U.S. Provisional Application Ser. No. 60/009,180 filed Dec. 22, 1995.

BACKGROUND

The biological significance of the Ras oncogene, and the role of both Ras and the enzyme known as farnesyl protein transferase in the conversion of normal cells to cancer cells, are described in PCT International Publication Nos. WO95/00497 and WO95/10516. Each of those publications also describes a distinct class of compounds which inhibit the activity of the enzyme farnesyl protein transferase, and thereby the farnesylation of the Ras protein.

PCT International Publication No. WO95/10516 relates to tricyclic amide and urea compounds of the general formula (1.0)

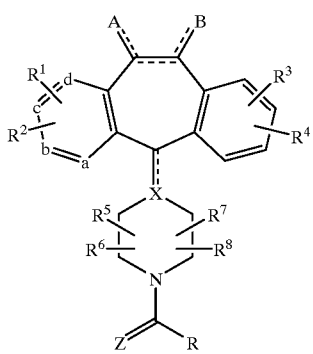

(1.0)

and their use in a method for inhibiting Ras function and the abnormal growth of cells. A number of sub-generic classes of compounds of formula (1.0) are described, which include compounds of the formulae (5.0c), (5.1c) and (5.2a)

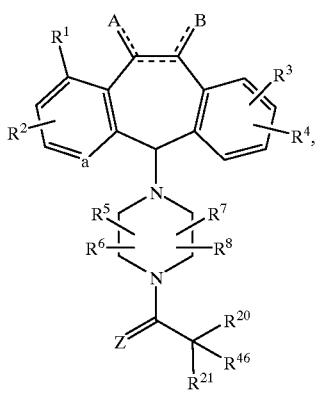

(5.0c)

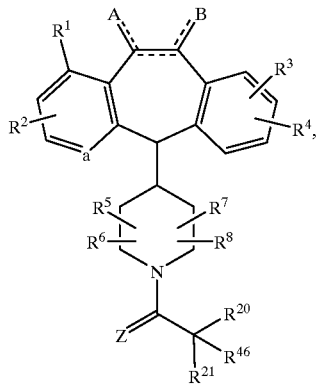

(5.1c)

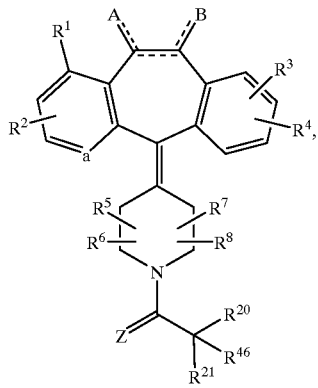

(5.2a)

as well as the 11-R-isomer and 11-S-isomers of compounds (5.0c) and (5.1c). A number of specific compounds within each such sub-genus are also described therein, as is the biological activity of those compounds.

SUMMARY OF THE INVENTION

The present invention provides novel tricyclic amide compounds selected from the group consisting of:

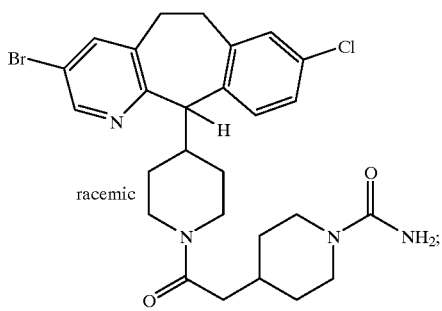

(1.0)

(2.0)
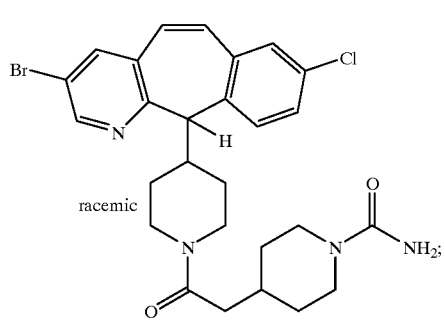
(3.0)
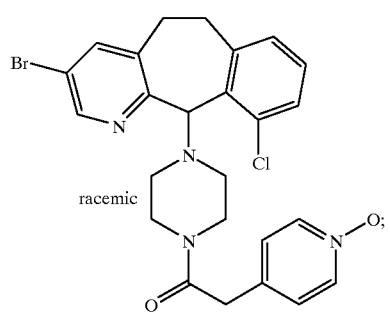
(5.0)
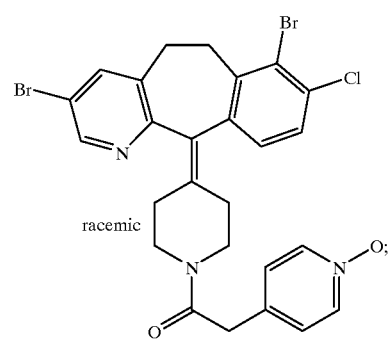
(6.0)
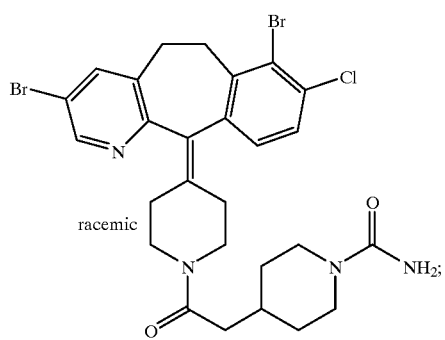
(7.0)
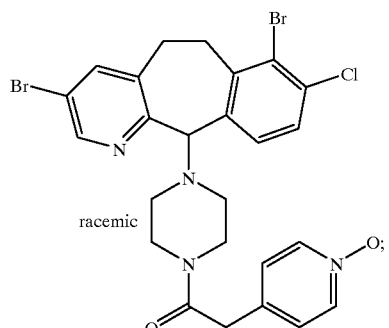
(7.0A)
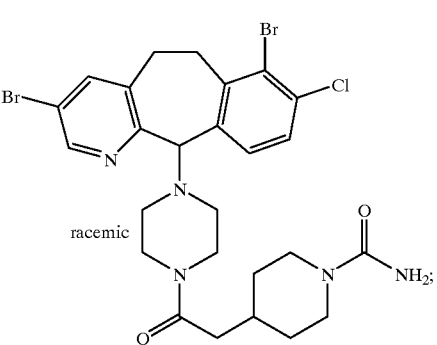
(8.0)
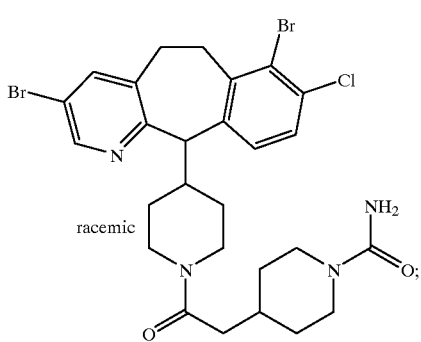
(8.0A)
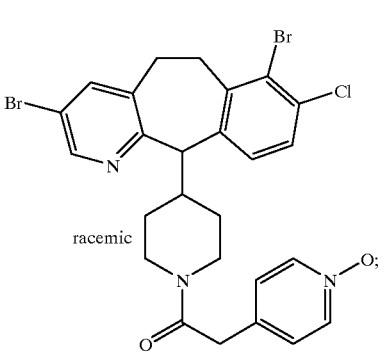

-continued
(9.0)
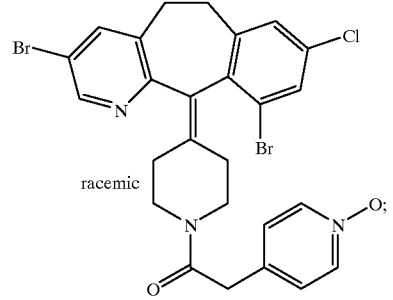
(10.0)
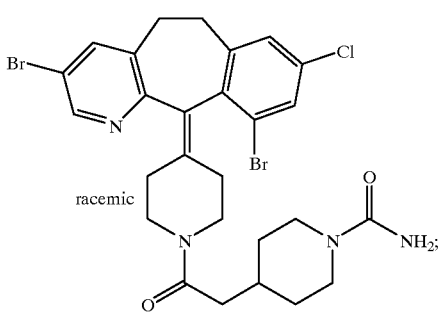
(11.0)
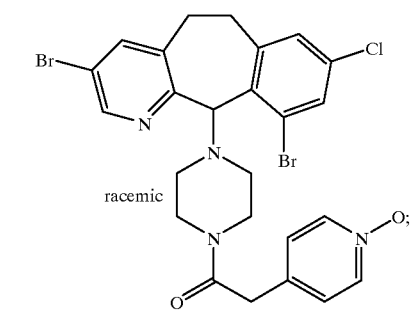
(12.0)
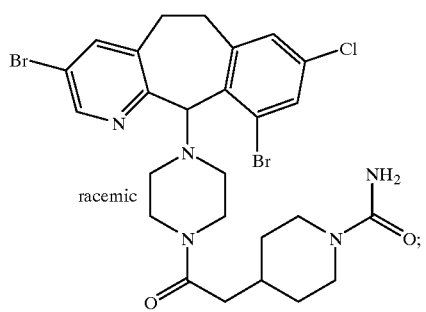
(13.0)
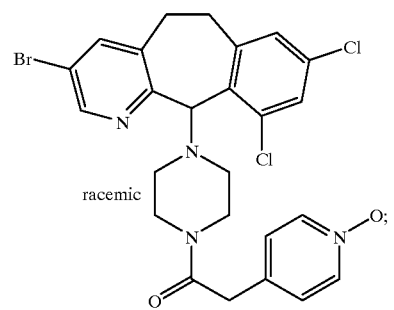
-continued
(14.0)
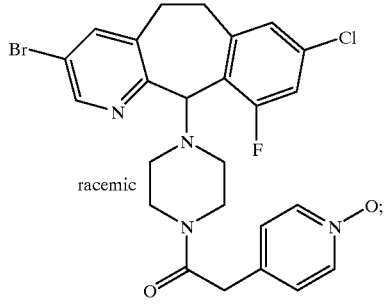
(15.0)
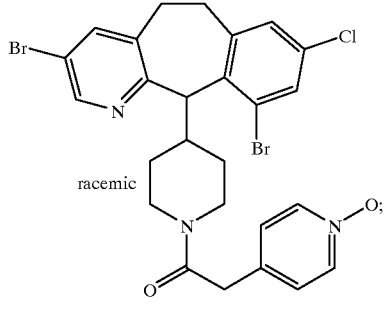
(16.0)
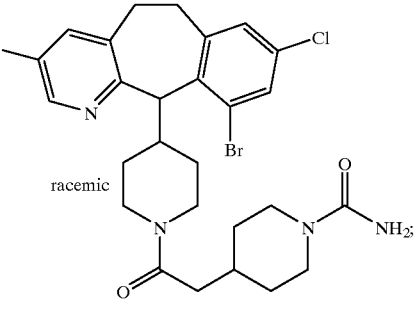
(17.0)
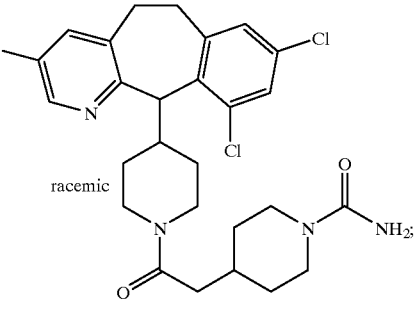
(18.0)
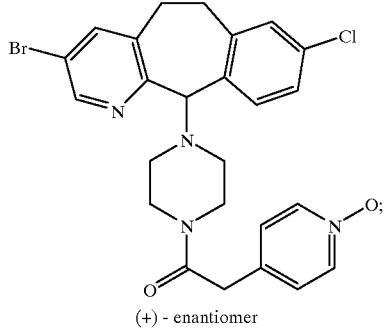
(+) - enantiomer -continued
(19.0)
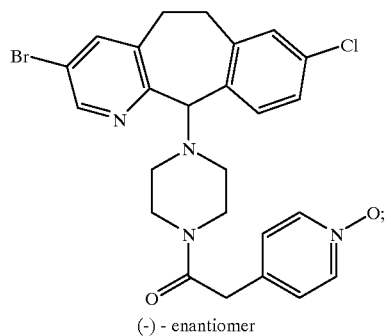
(−) - enantiomer
(20.0)
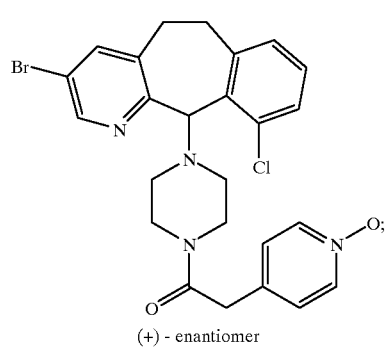
(+) - enantiomer
(21.0)
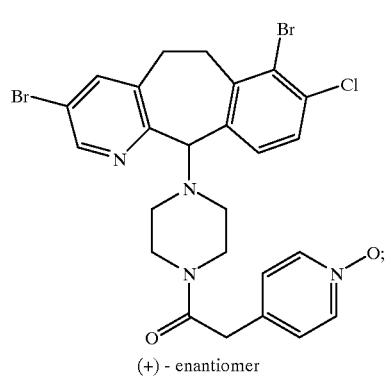
(+) - enantiomer
(22.0)
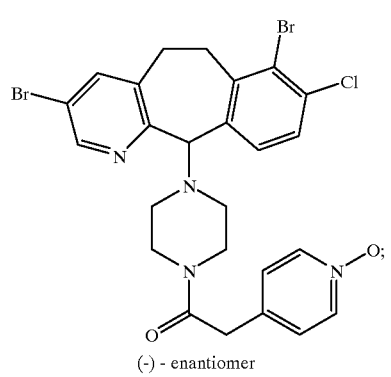
(−) - enantiomer
-continued
(23.0)
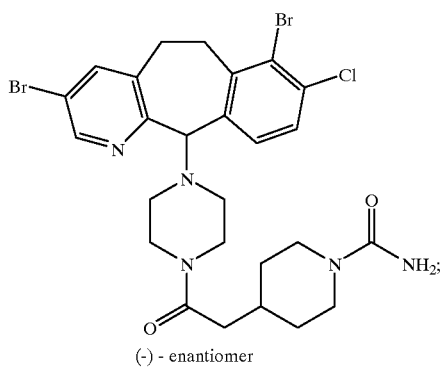
(−) - enantiomer
(24.0)
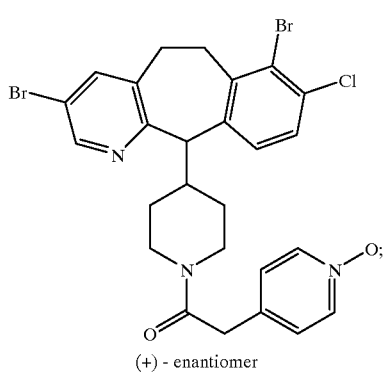
(+) - enantiomer
(25.0)
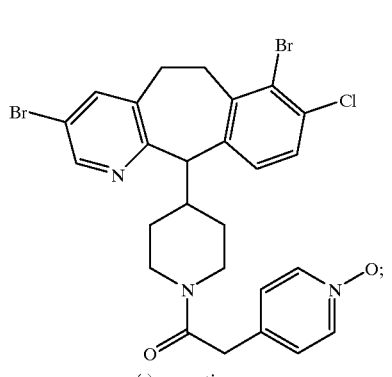
(−) - enantiomer
(26.0)
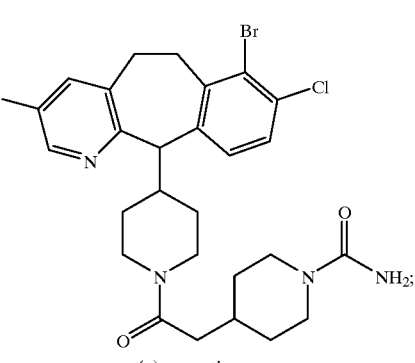
(+) - enantiomer -continued
(27.0)
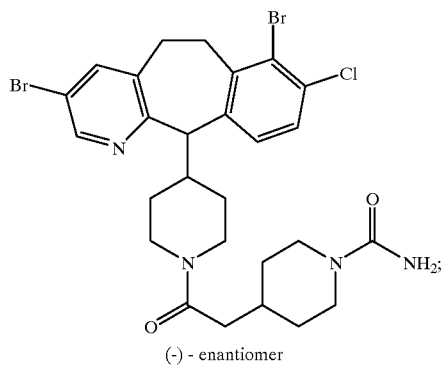
(−) - enantiomer
(28.0)
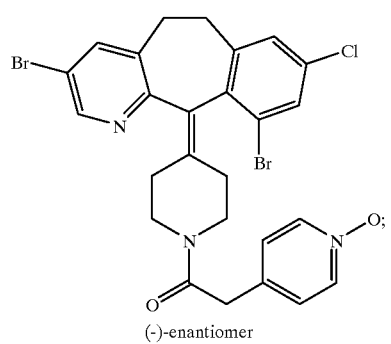
(−)-enantiomer
(29.0)
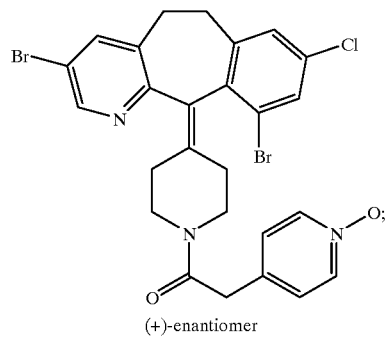
(+)-enantiomer
(30.0)
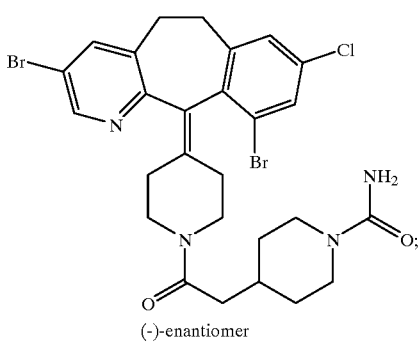
(−)-enantiomer
-continued
(31.0)
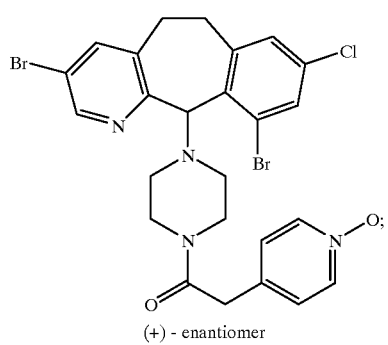
(+)-enantiomer
(32.0)
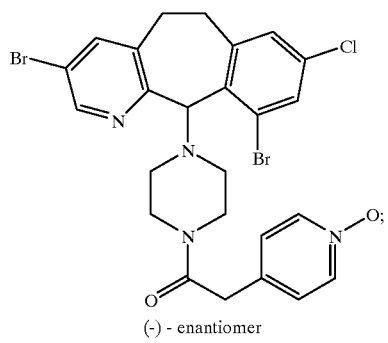
(+) - enantiomer
(33.0)
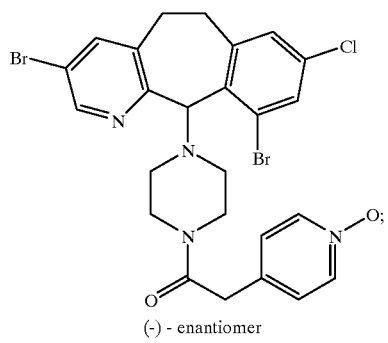
(−) - enantiomer
(34.0)
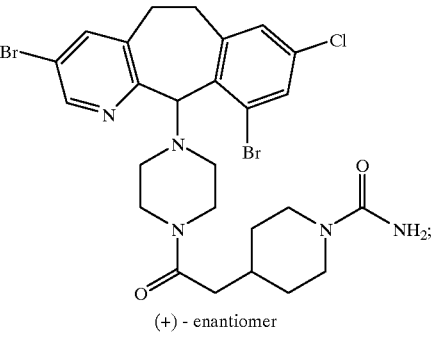
(+) - enantiomer

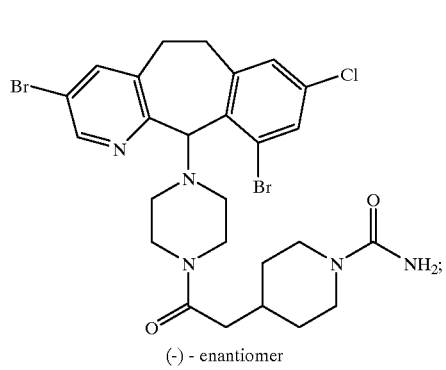
(35.0)
(-) - enantiomer
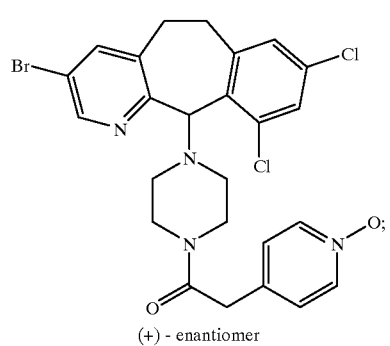
(36.0)
(+) - enantiomer
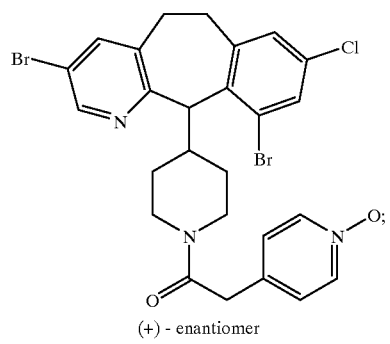
(37.0)
(+) - enantiomer
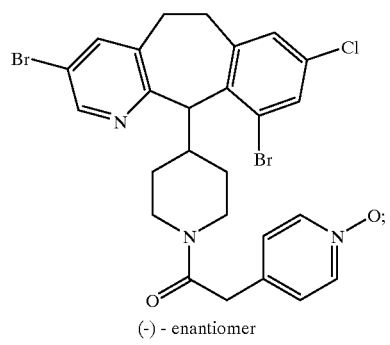
(38.0)
(-) - enantiomer
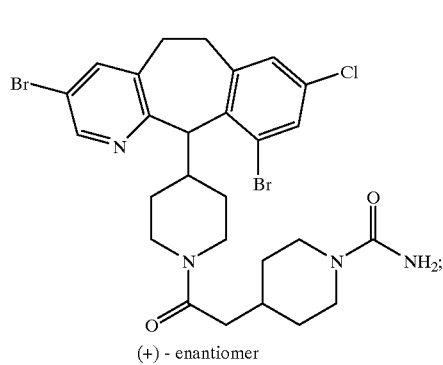
(39.0)
(+) - enantiomer
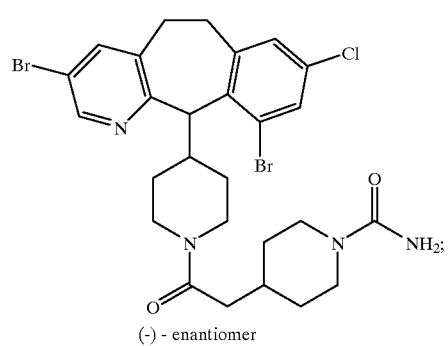
(40.0)
(-) - enantiomer
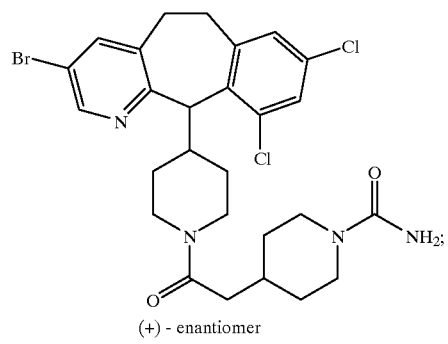
(41.0)
(+) - enantiomer
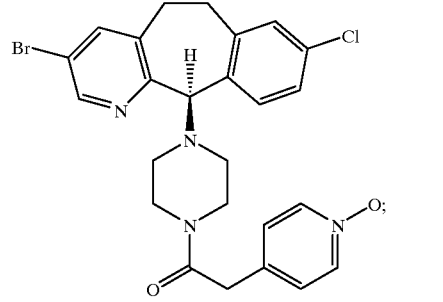
(42.0)

(43.0), (44.0), (45.0), (46.0), (47.0), (48.0), (49.0), (50.0), (51.0)

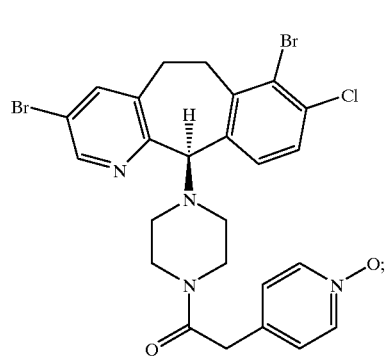
(52.0)
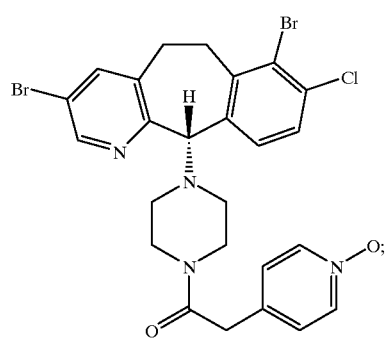
(53.0)
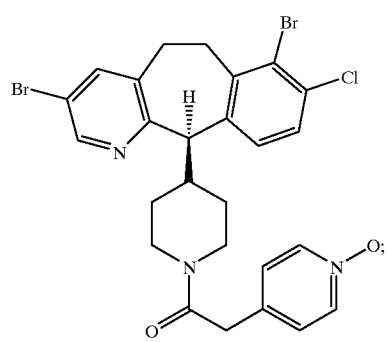
(54.0)
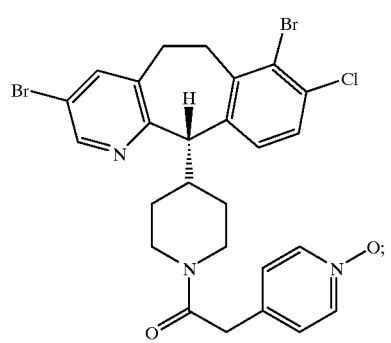
(55.0)
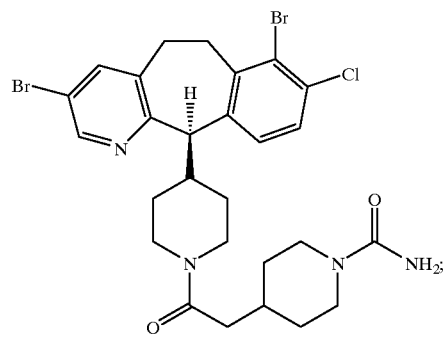
(56.0)
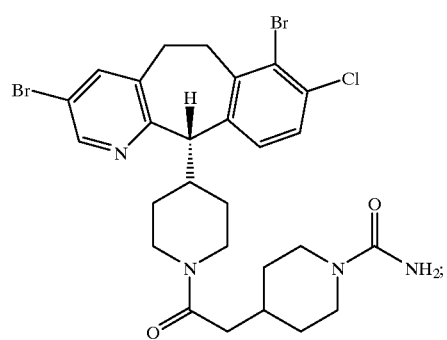
(57.0)
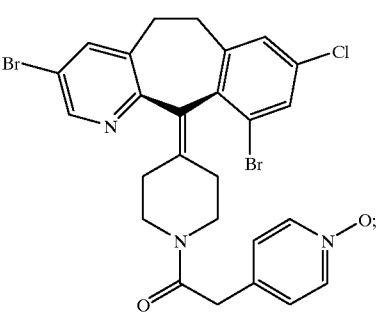
(58.0)
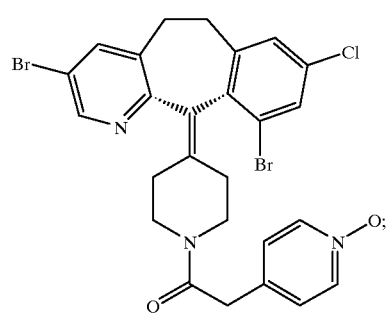
(59.0)

(60.0) 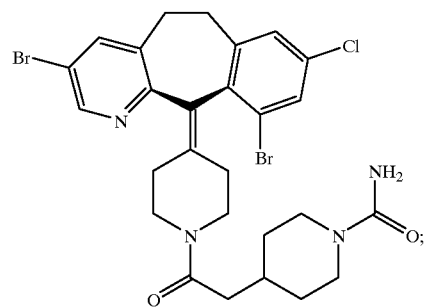
(61.0) 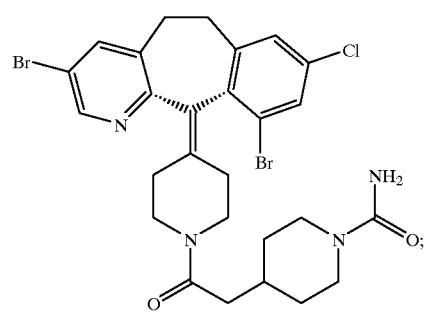
(62.0) 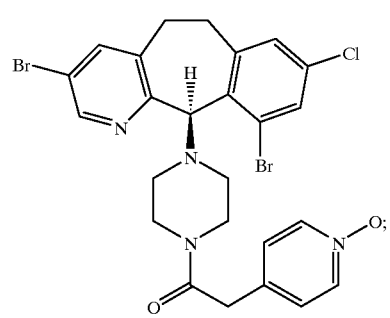
(63.0) 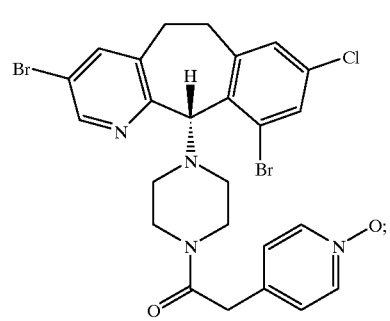
(64.0) 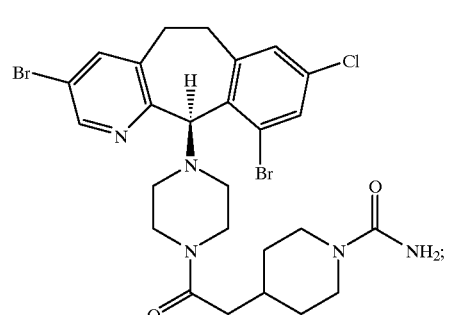
(65.0) 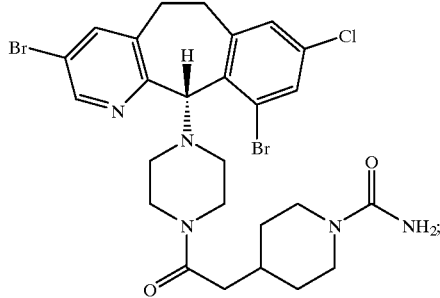
(66.0) 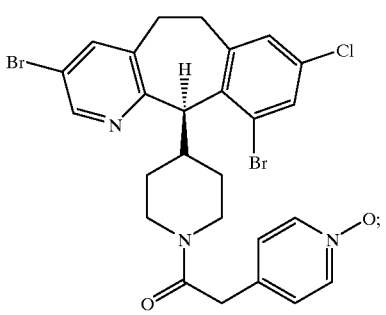
(67.0) 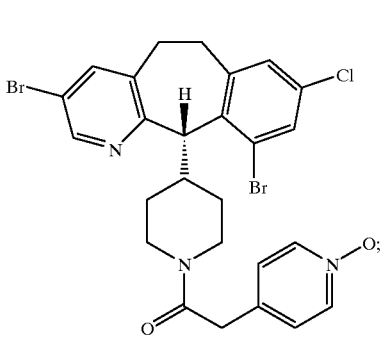
(68.0) 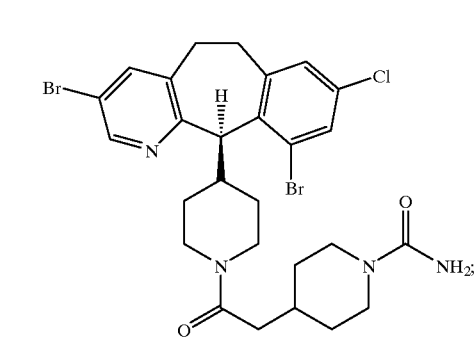
(69.0) 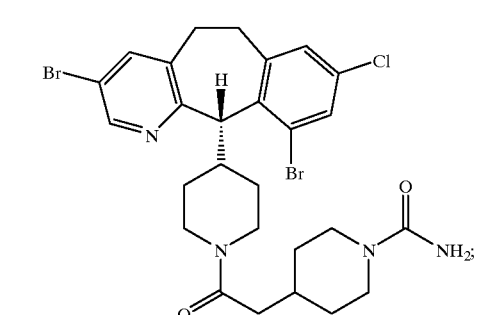

(70.0) 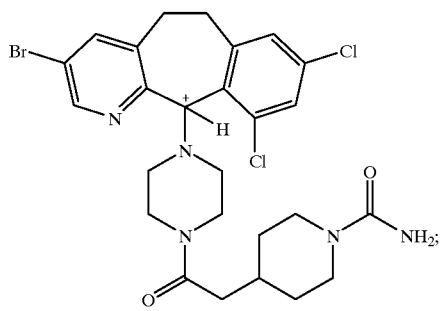
(75.0) 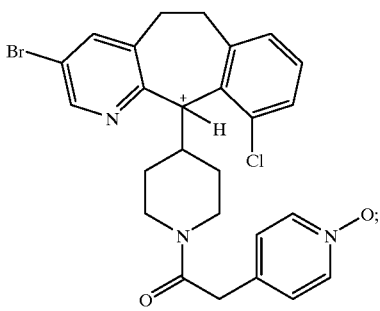
(71.0) 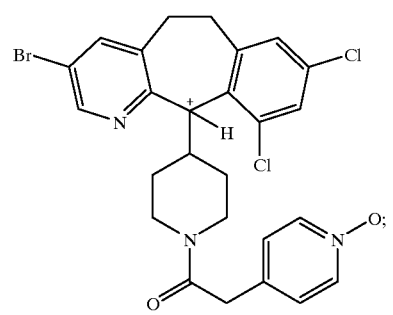
(76.0) 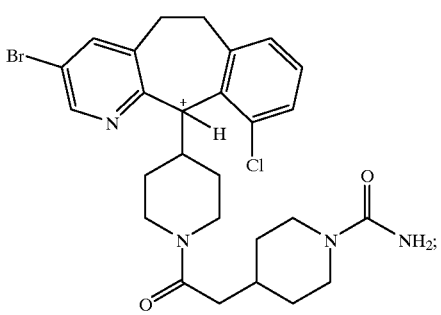
(72.0) 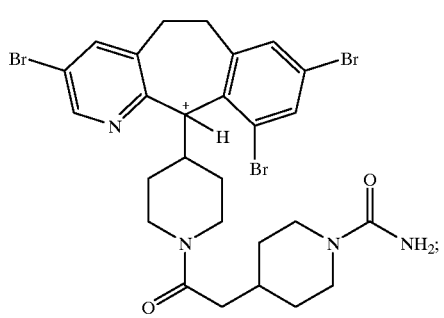
(77.0) 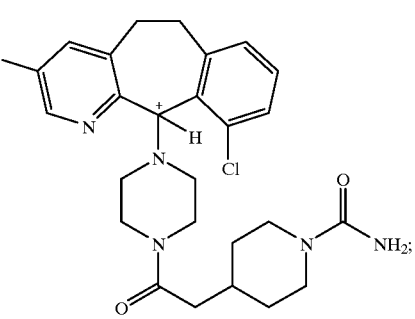
(73.0) 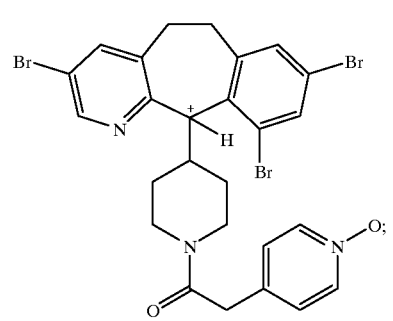
(78.0) 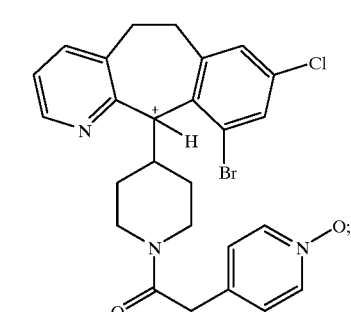
(74.0) 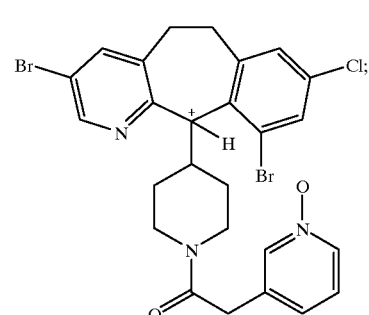
(79.0) 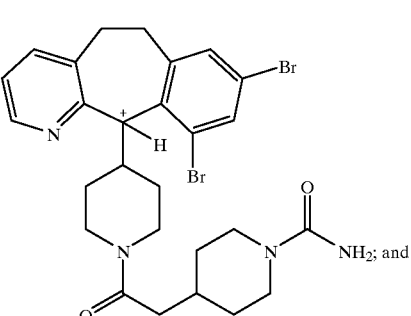

21

-continued

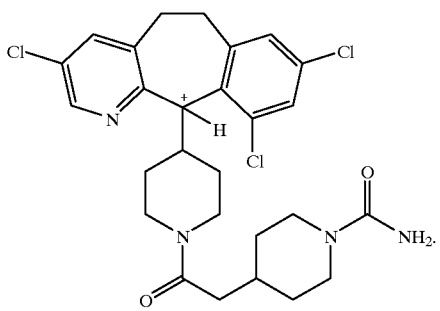

(80.0)

or pharmaceutically acceptable salts thereof.

Optical rotation of the compounds ((+)- or (−)-) are measured in methanol or ethanol at 25° C.

This invention includes the above compounds in the amorphous state or in the cyrstalline state.

Thus, compounds of this invention include compounds selected from the group consisting of: Compounds 1.0, 2.0, 3.0, 50.0, 6.0, 7.0, 7.0A, 8.0, 8.0A, 9.0, 10.0, 11.0, 12.0, 13.0, 14.0, 15.0, 16.0, and 17.0, or pharmaceutically acceptable salts thereof, wherein said compounds are as defined above.

Compounds of this invention also include compounds selected from the group consisting of: Compounds 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, and 41.0, or pharmaceutically acceptable salts thereof, and wherein said compounds are as defined above.

Compounds of this invention also include compounds selected from the group consisting of: (+)-enantiomer Compounds 70.0, 71.0, 72.0, 73.0, 74.0, 75.0, 76.0, 77.0, 78.0, 79.0 and 80.0, or pharmaceutically acceptable salts thereof, and wherein said compounds are as defined above.

Also, compounds of this invention include compounds selected from the group consisting of: Compounds 42.0, 43.0, 44.0, 45.0, 46.0, 47.0, 48.0, 49.0, 50.0, 51.0, 52.0, 53.0, 54.0, 55.0, 56.0, 57.0, 58.0, 59.0, 60.0, 61.0, 62.0, 63.0, 64.0, 65.0, 66.0, 67.0, 68.0 and 69.0, or pharmaceutically acceptable salts thereof, wherein said compounds are as defined above.

Preferred compounds include the 3,7,8-trihalo compounds having a (−)-optical rotation. For example, Compounds 22.0, 23.0, 25.0 and 27.0.

Preferred compounds also include the 3,8,10-trihalo compounds having a (+)-optical rotation. For example, Compounds 29.0, 31.0, 32.0, 34.0, 36.0, 37.0, 39.0 and 41.0.

Preferred compounds also include the 3,10-dihalo compounds having a (+)-optical rotation, for example, Compound 20.0.

Preferred compounds also include the 3,7-dibromo-8-chloro compounds having S stereochemistry at the C-11 position. For example, Compounds 50.0, 53.0, 55.0 and 57.0.

Preferred compounds also include the 3,10-dibromo-8-chlorocompounds having R stereochemistry at the C-11 position. For example, Compounds 62.0, 64.0, 66.0 and 68.0.

Preferred compounds also include Compounds 16.0, 17.0, 39.0, 40.0, 41.0, 68.0 and 69.0.

More preferred compounds are Compounds 16.0, 39.0, 40.0, 68.0 and 69.0. Most preferred compounds are Compounds 16.0, 39.0 and 68.0. Even more preferred is Compound 39.0 or 68.0.

22

Those skilled in the art will appreciate that the tricyclic ring system is numbered:

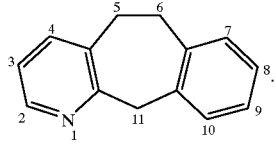

Those skilled in the art will also appreciate that the S and R stereochemistry at the C-11 bond are:

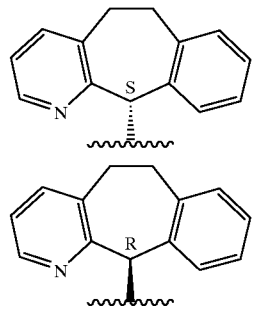

Inhibition of farnesyl protein transferase by the tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras. The compounds of this invention have been demonstrated to have anti-tumor activity in animal models.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting tumor growth by administering an effective amount of the tricyclic compounds, described herein, to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancers and prostate cancers.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the tricyclic compounds described herein.

The compounds of this invention inhibit farnesyl protein transferase and the farnesylation of the oncogene protein Ras. This invention further provides a method of inhibiting ras farnesyl protein transferase, in mammals, especially humans, by the administration of an effective amount of the tricyclic compounds described above. The administration of the compounds of this invention to patients, to inhibit farnesyl protein transferase, is useful in the treatment of the cancers described above.

The tricyclic compounds useful in the methods of this invention inhibit the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

$M^+$-represents the molecular ion of the molecule in the mass spectrum;

$MH^+$-represents the molecular ion plus hydrogen of the molecule in the mass spectrum;

Pyridyl N-oxides are herein represented by the group

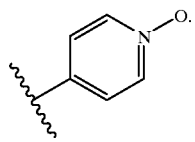

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxy-benzotriazole (HOBT); m-chloroperbenzoic acid (MCPBA); triethylamine (Et₃N); diethyl ether (Et₂O); ethyl chloroformate (ClCO₂Et); 1-(3-dimethylaminopropyl)-3-ethyl carbodiimde hydrochloride (DEC); diisobutylaluminum hydride (DIBAL); isopropanol (iPrOH); dimethylsulfoxide (DMSO).

Certain compounds of the present invention may exist in different isomeric forms (e.g., enantiomers or diastereoisomers) including atropisomers (i.e., compounds wherein the 7-membered ring is in a fixed conformation such that the 11-carbon atom is positioned above or below the plane of the fused beznene rings due to the presence of a 10-bromo substituent). The invention contemplates all such isomers both in pure form and in admixture, including racemic mixtures. Enol forms are also included.

Certain basic tricyclic compounds also form pharmaceutically acceptable salts, e.g., acid addition salts. For example, the pyrido-nitrogen atoms may form salts with strong acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such salts are intended to be pharmaceutically acceptable salts within the scope of the invention and all are considered equivalent to the free forms of the corresponding compounds for purposes of the invention.

The compounds of the present invention can be prepared by the procedures described below.

The compound of Example 10 is obtained in the cyrstalline state. Those skilled in the art will appreciate that compounds obtained in the amorphous state can be obtained in the cyrstalline state by cyrstallizing the amorphous materials from solvents or solvent mixtures such as acetone, diethyl ether, ethyl acetate, ethanol, 2-propanol, tert-butyl ether, water and the like according to procedures well known in the art.

Those skilled in the art will also appreciate that the racemic mixture of Compound 7.0A can be made according to the procedures described below. For Example, the intermediate of Preparative Example 6 can be used to prepare Compound 7.0A.

PREPARATIVE EXAMPLE 1

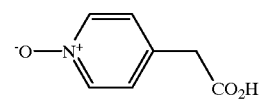

Step A:

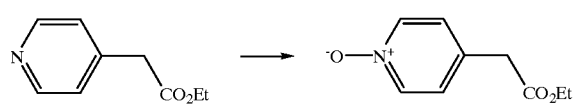

Combine 10 g (60.5 mmol) of ethyl 4-pyridylacetate and 120 mL of dry CH₂Cl₂ at −20° C., add 10.45 g (60.5 mmol) of MCPBA and stir at −20° C. for 1 hour and then at 25° C. for 67 hours. Add an additional 3.48 g (20.2 mmoles) of MCPBA and stir at 25° C. for 24 hours. Dilute with CH₂Cl₂ and wash with saturated NaHCO₃ (aqueous) and then water. Dry over MgSO₄, concentrate in vacuo to a residue, and chromatograph (silica gel, 2%–5.5% (10% NH₄OH in MeOH)/CH₂Cl₂) to give 8.12 g of the product compound. Mass Spec.: MH⁺=182.15

Step B:

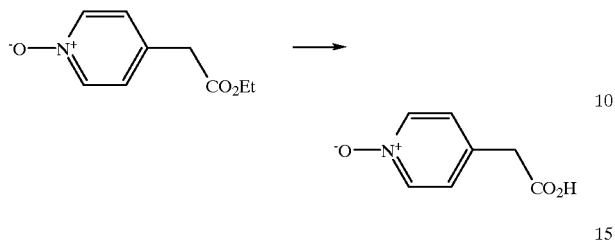

Combine 3.5 g (19.3 mmol) of the product of Step A, 17.5 mL of EtOH and 96.6 mL of 10% NaOH (aqueous) and heat the mixture at 67° C. for 2 hours. Add 2 N HCl (aqueous) to adjust to pH=2.37 and concentrate in vacuo to a residue. Add 200 mL of dry EtOH, filter through celite® and wash the filter cake with dry EtOH (2×50 ml). Concentrate the combined filtrates in vacuo to give 2.43 g of the title compound.

PREPARATIVE EXAMPLE 2

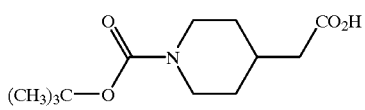

The title compound is prepared via the process disclosed in PCT International Publication No. WO95/10516.

PREPARATIVE EXAMPLE 3

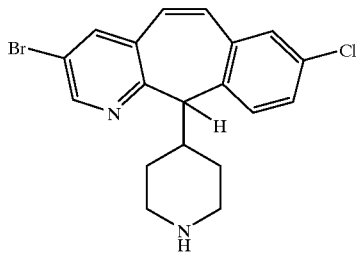

Step A:

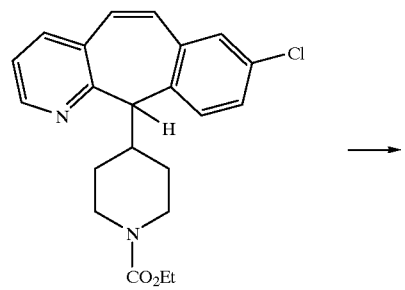

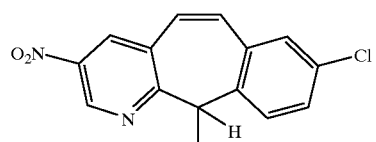

3A (i)

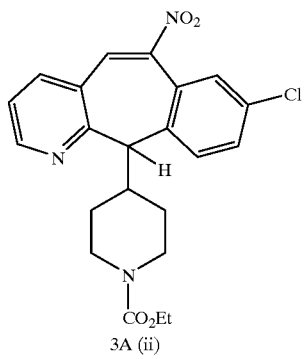

3A (ii)

Combine 14.95 g (39 mmol) of 8-chloro-11-(1-ethoxycarbonyl-4-piperidinyl)-11H-benzo[5,6]cyclohepta[1,2-b]pyridine and 150 mL of CH₂Cl₂, then add 13.07 g (42.9 mmol) of (nBu)₄NNO₃ and cool the mixture to 0° C. Slowly add (dropwise) a solution of 6.09 mL (42.9 mmol) of TFAA in 20 mL of CH₂Cl₂ over 1.5 hours. Keep the mixture at 0° C. overnight, then wash successively with saturated NaHCO₃ (aqueous), water and brine. Dry the organic solution over Na₂SO₄, concentrate in vacuo to a residue and chromatograph the residue (silica gel, EtOAc/hexane gradient) to give 4.32 g and 1.90 g of the two product compounds 3A(i) and 3A(ii), respectively.

Mass Spec. for compound 3A(i): MH⁺=428.2.

Mass Spec. for compound 3A(ii): MH⁺=428.3.

Step B:

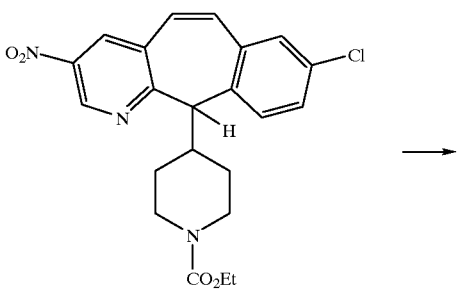

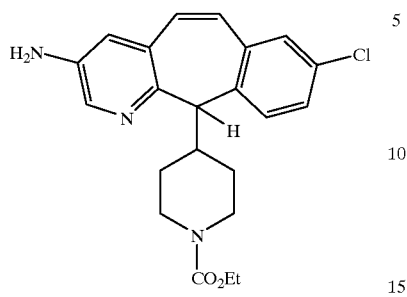

Combine 22.0 g (51.4 mmol) of the product 3A(i) from Step A, 150 mL of 85% EtOH (aqueous), 25.85 g (0.463 mole) of Fe powder and 2.42 g (21.8 mmol) of CaCl₂, and heat at reflux overnight. Add 12.4 g (0.222 mole) of Fe powder and 1.2 g (10.8 mmol) of CaCl₂ and heat at reflux for 2 hours. Add another 12.4 g (0.222 mole) of Fe powder and 1.2 g (10.8 mmol) of CaCl₂ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, MeOH/CH₂Cl₂ gradient) to give 16.47 g of the product compound. MH⁺=398.

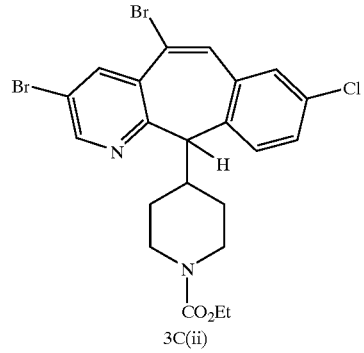

Combine 16.47 g (41.4 mmol) of the product from Step B, and 150 mL of 48% HBr (aqueous) and cool to −3° C. Slowly add (dropwise) 18 mL of bromine, then slowly add (dropwise) a solution of 8.55 g (0.124 mole) of NaNO₂ in 85 mL of water. Stir for 45 minutes at −3° to 0° C., then adjust to pH=10 by adding 50% NaOH (aqueous). Extract with EtOAc, wash the extracts with brine and dry the extracts over Na₂SO₄. Concentrate to a residue and chromatograph (silica gel, EtOAc/hexane gradient) to give 10.6 g and 3.28 g of the two product compounds 3C(i) and 3C(ii), respectively.

Mass Spec. for compound 3C(i): MH⁺=461.2.
Mass Spec. for compound 3C(ii): MH⁺=539.

Step C:

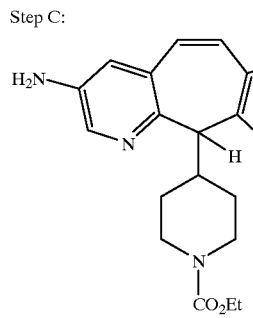

Step D:

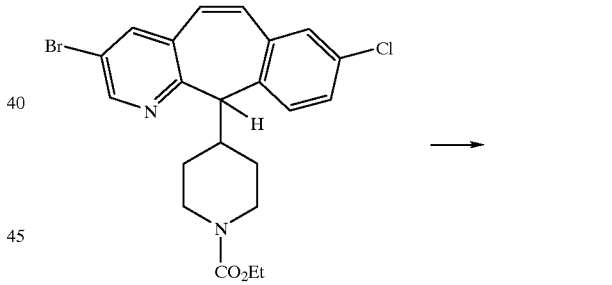

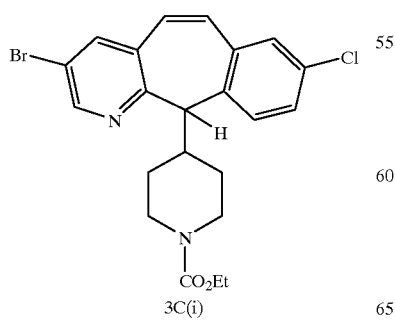

Hydrolyze the product 3C(i) of Step C by dissolving in concentrated HCl and heating to about 100° C. for 16 hours. Cool the mixture, then neutralize with 1 M NaOH (aqueous). Extract with CH₂Cl₂, dry the extracts over MgSO₄, filter and concentrate in vacuo to the title compound.

Mass Spec.: MH⁺=466.9.

PREPARATIVE EXAMPLE 4

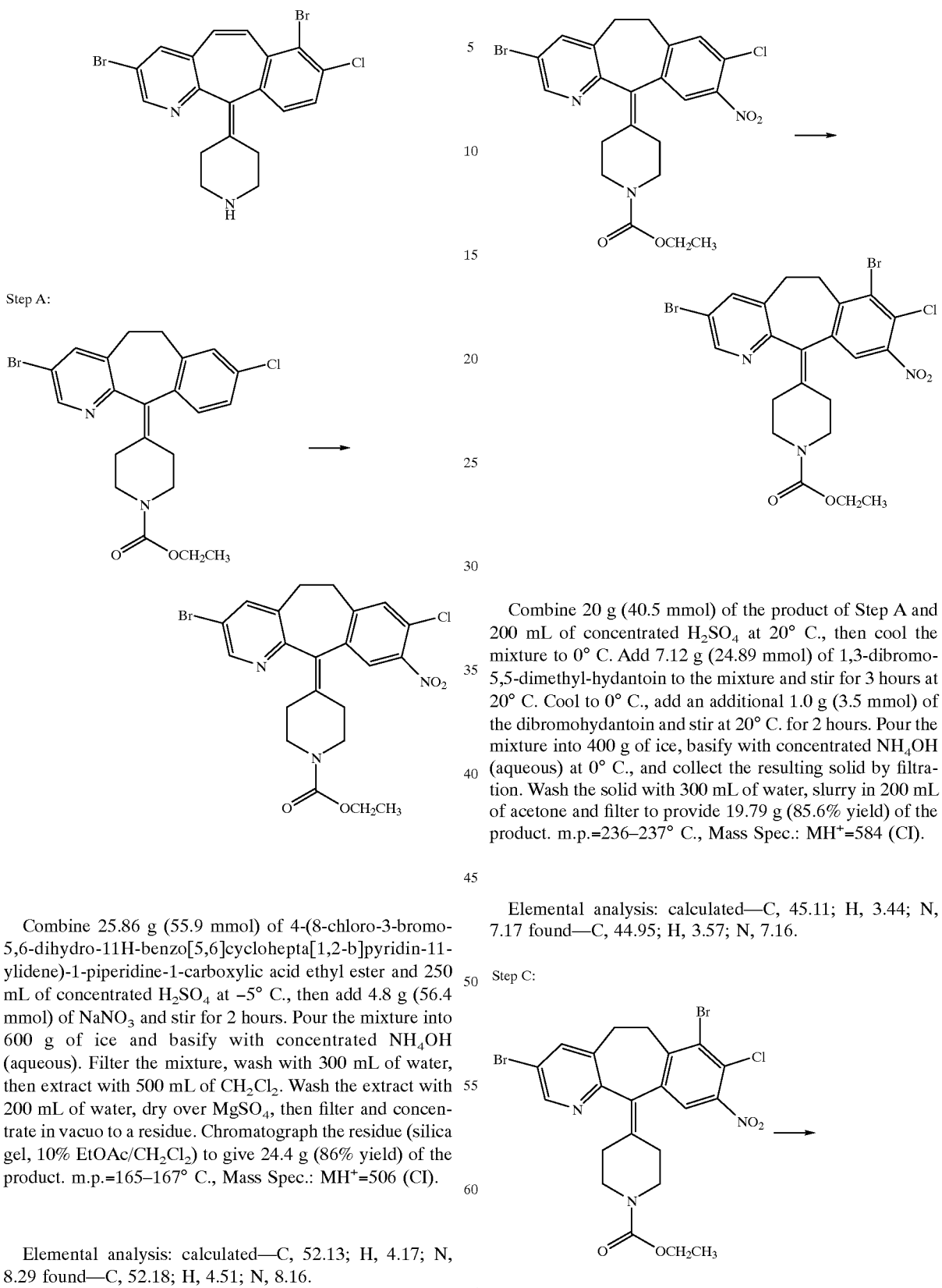

Step A:

Combine 25.86 g (55.9 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 250 mL of concentrated H$_2$SO$_4$ at −5° C., then add 4.8 g (56.4 mmol) of NaNO$_3$ and stir for 2 hours. Pour the mixture into 600 g of ice and basify with concentrated NH$_4$OH (aqueous). Filter the mixture, wash with 300 mL of water, then extract with 500 mL of CH$_2$Cl$_2$. Wash the extract with 200 mL of water, dry over MgSO$_4$, then filter and concentrate in vacuo to a residue. Chromatograph the residue (silica gel, 10% EtOAc/CH$_2$Cl$_2$) to give 24.4 g (86% yield) of the product. m.p.=165–167° C., Mass Spec.: MH$^+$=506 (CI).

Elemental analysis: calculated—C, 52.13; H, 4.17; N, 8.29 found—C, 52.18; H, 4.51; N, 8.16.

Step B:

Combine 20 g (40.5 mmol) of the product of Step A and 200 mL of concentrated H$_2$SO$_4$ at 20° C., then cool the mixture to 0° C. Add 7.12 g (24.89 mmol) of 1,3-dibromo-5,5-dimethyl-hydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated NH$_4$OH (aqueous) at 0° C., and collect the resulting solid by filtration. Wash the solid with 300 mL of water, slurry in 200 mL of acetone and filter to provide 19.79 g (85.6% yield) of the product. m.p.=236–237° C., Mass Spec.: MH$^+$=584 (CI).

Elemental analysis: calculated—C, 45.11; H, 3.44; N, 7.17 found—C, 44.95; H, 3.57; N, 7.16.

Step C:

-continued

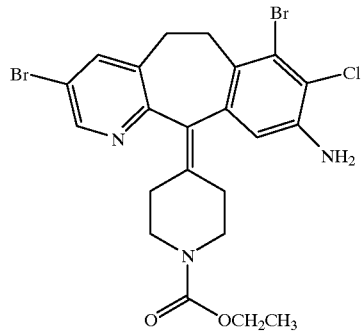

Combine 25 g (447 mmol) of Fe filings, 10 g (90 mmol) of CaCl$_2$ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of CH$_2$Cl$_2$, wash with 300 mL of water and dry over MgSO$_4$. Filter and concentrate in vacuo to a residue, then chromatograph (silica gel, 30% EtOAc/CH$_2$Cl$_2$) to give 11.4 g (60% yield) of the product. m.p.=211–212° C., Mass Spec.: MH$^+$=554 (CI).

Elemental analysis: calculated—C, 47.55; H, 3.99; N, 7.56 found—C, 47.45; H, 4.31; N, 7.49.

Step D:

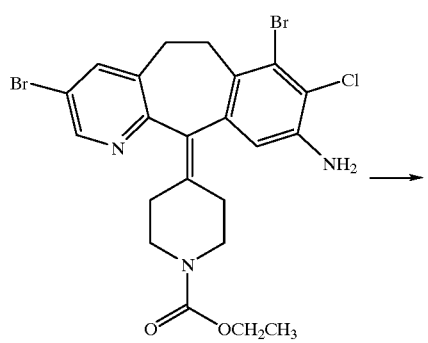

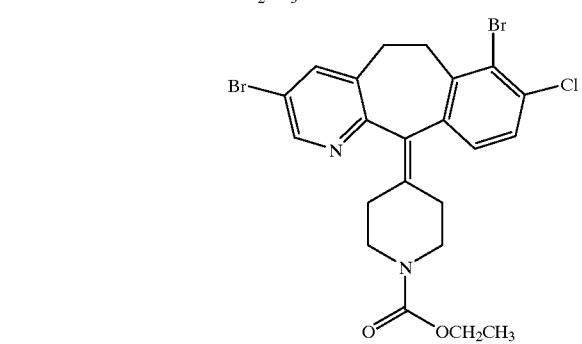

Slowly add (in portions) 20 g (35.9 mmol) of the product of Step C to a solution of 8 g (116 mmol) of NaNO$_2$ in 120 mL of concentrated HCl (aqueous) at −10° C. Stir the resulting mixture at 0° C. for 2 hours, then slowly add (dropwise) 150 mL (1.44 mole) of 50% H$_3$PO$_2$ at 0° C. over a 1 hour period. Stir at 0° C. for 3 hours, then pour into 600 g of ice and basify with concentrated NH$_4$OH (aqueous). Extract with 2×300 mL of CH$_2$Cl$_2$, dry the extracts over MgSO$_4$, then filter and concentrate in vacuo to a residue. Chromatograph the residue (silica gel, 25% EtOAc/hexanes) to give 13.67 g (70% yield) of the product. m.p.=163–165° C., Mass Spec.: MH$^+$=539 (CI).

Elemental analysis: calculated—C, 48.97; H, 4.05; N, 5.22 found—C, 48.86; H, 3.91; N, 5.18.

Step E:

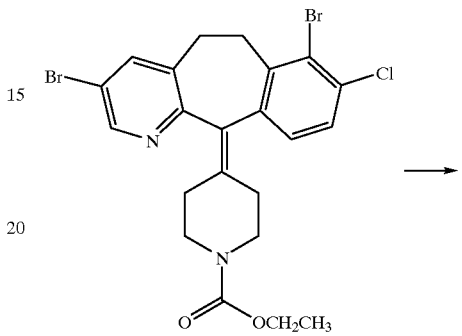

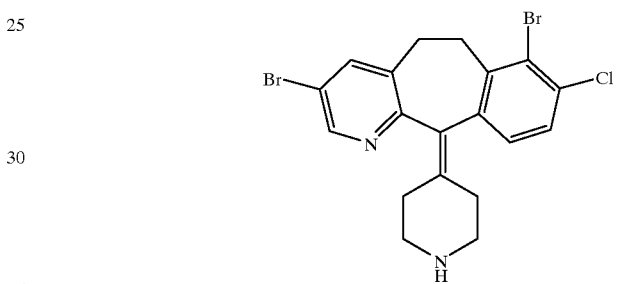

Combine 6.8 g (12.59 mmol) of the product of Step D and 100 mL of concentrated HCl (aqueous) and stir at 85° C. overnight. Cool the mixture, pour it into 300 g of ice and basify with concentrated NH$_4$OH (aqueous). Extract with 2×300 mL of CH$_2$Cl$_2$, then dry the extracts over MgSO$_4$. Filter, concentrate in vacuo to a residue, then chromatograph (silica gel, 10% MeOH/EtOAc+2% NH$_4$OH (aqueous)) to give 5.4 g (92% yield) of the title compound. m.p.= 172–174° C., Mass Spec.: MH$^+$=467.

Elemental analysis: calculated—C, 48.69; H, 3.65; N, 5.97 found—C, 48.83; H, 3.80; N, 5.97.

PREPARATIVE EXAMPLE 5

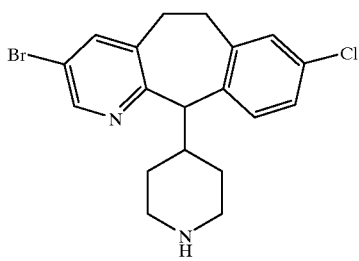

-continued

Step A:

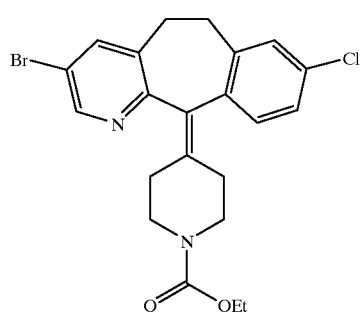

Hydrolyze 2.42 g of 4-(8-chloro-3-bromo-5,6-dihydro-11H-benzo[5,6]cyclohepta[1,2-b]pyridin-11-ylidene)-1-piperidine-1-carboxylic acid ethyl ester via substantially the same procedure as described in Preparative Example 3, Step D, to give 1.39 g (69% yield) of the product. $MH^+=389$.

Step B:

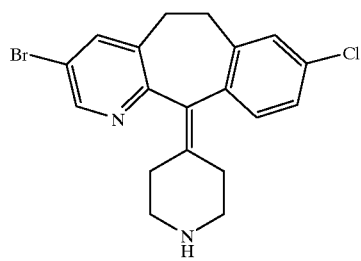

Combine 1 g (2.48 mmol) of the product of Step A and 25 mL of dry toluene, add 2.5 mL of 1 M DIBAL in toluene and heat the mixture at reflux. After 0.5 hours, add another 2.5 mL of 1 M DIBAL in toluene and heat at reflux for 1 hour. (The reaction is monitored by TLC using 50% MeOH/ $CH_2Cl_2$+$NH_4OH$ (aqueous).) Cool the mixture to room temperature, add 50 mL of 1 N HCl (aqueous) and stir for 5 min. Add 100 mL of 1 N NaOH (aqueous), then extract with EtOAc (3×150 mL). Dry the extracts over $MgSO_4$, filter and concentrate in vacuo to give 1.1 g of the title compound. $MH^+=391$.

PREPARATIVE EXAMPLE 6

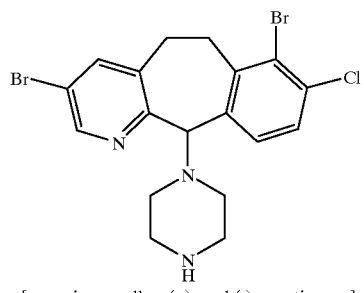

[racemic as well as (+)- and (-)-enantiomers]

Step A:

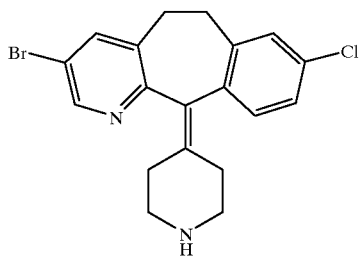

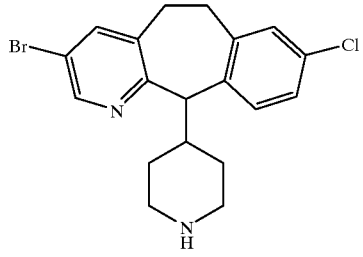

Combine 16.6 g (0.03 mole) of the product of Preparative Example 4, Step D, with a 3:1 solution of $CH_3CN$ and water (212.65 mL $CH_3CN$ and 70.8 mL of water) and stir the resulting slurry overnight at room temperature. Add 32.833 g (0.153 mole) of $NaIO_4$ and then 0.31 g (2.30 mmol) of $RuO_2$ and stir at room temperature (the addition of $RuO_2$ is accompanied by an exothermic reaction and the temperature climbs from 20° to 30° C.). Stir the mixture for 1.3 hrs. (temperature returned to 25° C. after about 30 min.), then filter to remove the solids and wash the solids with $CH_2Cl_2$. Concentrate the filtrate in vacuo to a residue and dissolve the residue in $CH_2Cl_2$. Filter to remove insoluble solids and wash the solids with $CH_2Cl_2$. Wash the filtrate with water, concentrate to a volume of about 200 mL and wash with bleach, then with water. Extract with 6 N HCl (aqueous). Cool the aqueous extract to 0° C. and slowly add 50% NaOH (aqueous) to adjust to pH=4 while keeping the temperature <30° C. Extract twice with $CH_2Cl_2$, dry over $MgSO_4$ and concentrate in vacuo to a residue. Slurry the residue in 20 mL of EtOH and cool to 0° C. Collect the resulting solids by filtration and dry the solids in vacuo to give 7.95 g of the product. $^1$H NMR ($CDCl_3$, 200 MHz): 8.7 (s, 1H); 7.85 (m, 6H); 7.5 (d, 2H); 3.45 (m, 2H); 3.15 (m, 2H).

Step B:

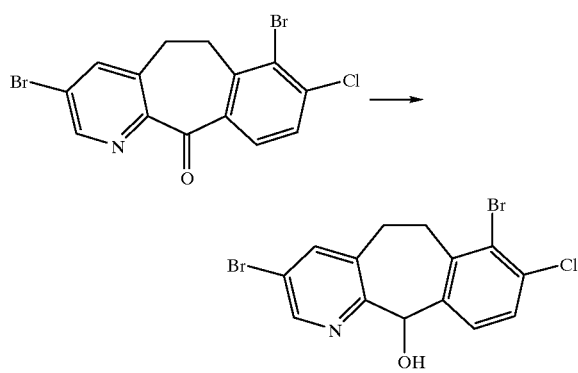

Combine 21.58 g (53.75 mmol) of the product of Step A and 500 mL of an anhydrous 1:1 mixture of EtOH and toluene, add 1.43 g (37.8 mmol) of NaBH$_4$ and heat the mixture at reflux for 10 min. Cool the mixture to 0° C., add 100 mL of water, then adjust to pH≈4–5 with 1 M HCl (aqueous) while keeping the temperature <10° C. Add 250 mL of EtOAc and separate the layers. Wash the organic layer with brine (3×50 mL) then dry over Na$_2$SO$_4$. Concentrate in vacuo to a residue (24.01 g) and chromatograph the residue (silica gel, 30% hexane/CH$_2$Cl$_2$) to give the product. Impure fractions were purified by rechromatography. A total of 18.57 g of the product was obtained. $^1$H NMR (DMSO-d$_6$, 400 MHz): 8.5 (s, 1H); 7.9 (s, 1H); 7.5 (d of d, 2H); 6.2 (s, 1H); 6.1 (s, 1H); 3.5 (m, 1H); 3.4 (m, 1H); 3.2 (m, 2H).

Step C:

Combine 18.57 g (46.02 mmol) of the product of Step B and 500 mL of CHCl$_3$, then add 6.70 mL (91.2 mmol) of SOCl$_2$, and stir the mixture at room temperature for 4 hrs. Add a solution of 35.6 g (0.413 mole) of piperazine in 800 mL of THF over a period of 5 min. and stir the mixture for 1 hr. at room temperature. Heat the mixture at reflux overnight, then cool to room temperature and dilute the mixture with 1 L of CH$_2$Cl$_2$. Wash with water (5×200 mL), and extract the aqueous wash with CHCl$_3$ (3×100 mL). Combine all of the organic solutions, wash with brine (3×200 mL) and dry over MgSO$_4$. Concentrate in vacuo to a residue and chromatograph (silica gel, gradient of 5%, 7.5%, 10% MeOH/CH$_2$Cl$_2$+NH$_4$OH) to give 18.49 g of the title compound as a racemic mixture.

Step D - Separation of Enantiomers:

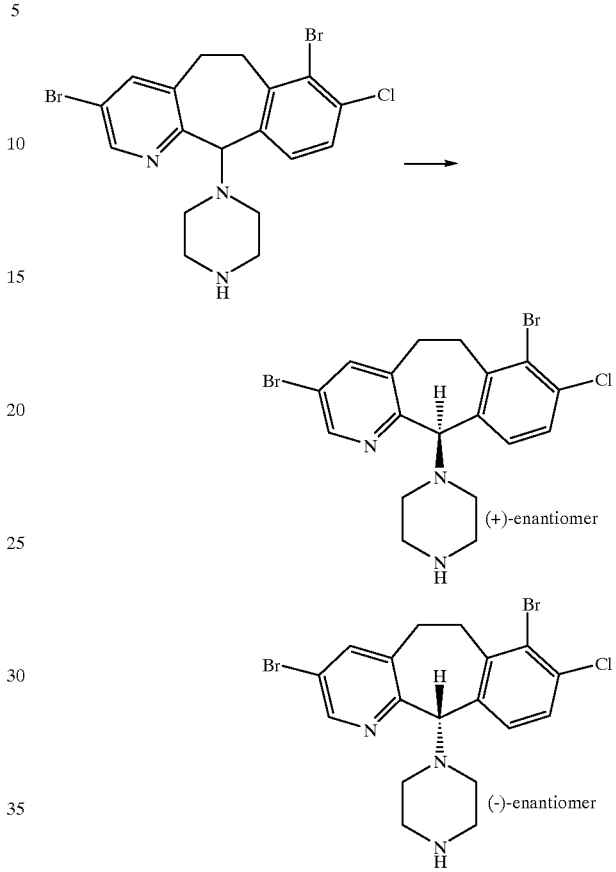

The racemic title compound of Step C is separated by preparative chiral chromatography (Chiralpack AD, 5 cm×50 cm column, flow rate 100 mL/min., 20% iPrOH/hexane+0.2% diethylamine), to give 9.14 g of the (+)-enantiomer and 9.30 g of the (−)-enantiomer.

Physical chemical data for (+)-enantiomer: m.p.= 74.5°–77.5° C.; Mass Spec. MH$^+$=471.9; $[\alpha]_D^{25}$=+97.4° (8.48 mg/2 mL MeOH).

Physical chemical data for (−)-enantiomer: m.p.= 82.9°–84.5° C.; Mass Spec. MH$^+$=471.8; $[\alpha]_D^{25}$=−97.4° (8.32 mg/2 mL MeOH).

PREPARATIVE EXAMPLE 7

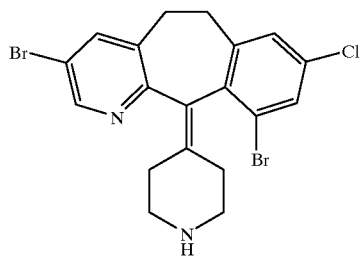

Step A:

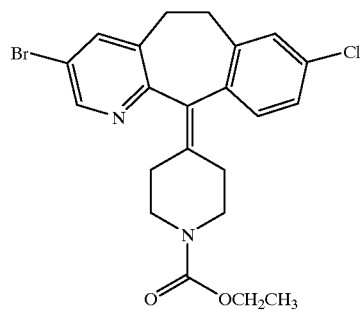

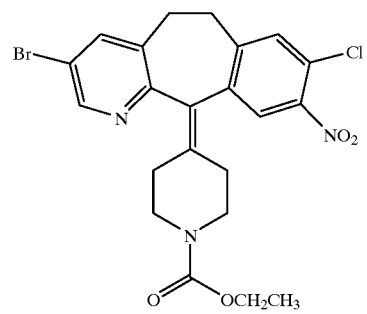

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of concentrated $H_2SO_4$ at −5° C., then add 3.89 g (38.5 mmol) of $KNO_3$ and stir for 4 hours. Pour the mixture into 3 L of ice and basify with 50% NaOH (aqueous). Extract with $CH_2Cl_2$, dry over $MgSO_4$, then filter and concentrate in vacuo to a residue. Recrystallize the residue from acetone to give 6.69 g of the product. $^1$H NMR (CDCl$_3$, 200 MHz): 8.5 (s, 1H); 7.75 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H). MH$^+$=506.

Step B:

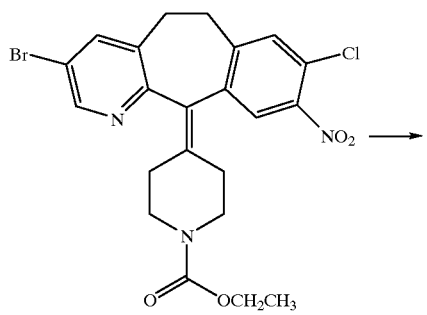

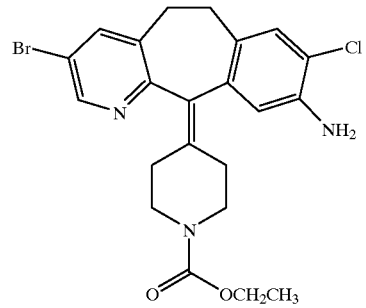

Combine 6.69 g (13.1 mmol) of the product of Step A and 100 mL of 85% EtOH/water, then add 0.66 g (5.9 mmol) of $CaCl_2$ and 6.56 g (117.9 mmol) of Fe and heat the mixture at reflux overnight. Filter the hot reaction mixture through Celite® and rinse the filter cake with hot EtOH. Concentrate the filtrate in vacuo to give 7.72 g of the product. Mass Spec.: MH$^+$=476.0.

Step C:

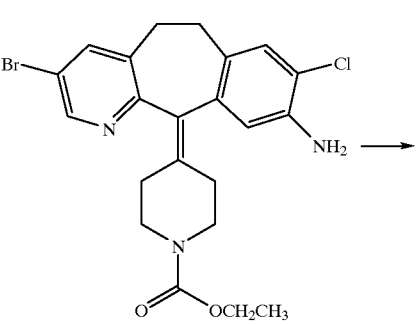

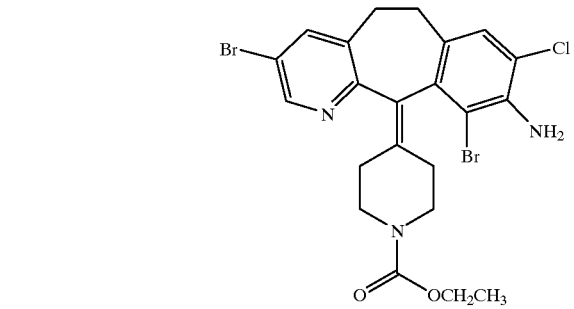

Combine 7.70 g of the product of Step B and 35 mL of HOAc, then add 45 mL of a solution of Br$_2$ in HOAc and stir the mixture at room temperature overnight. Add 300 mL of 1 N NaOH (aqueous), then 75 mL of 50% NaOH (aqueous) and extract with EtOAc. Dry the extract over MgSO$_4$ and concentrate in vacuo to a residue. Chromatograph the residue (silica gel, 20%–30% EtOAc/hexane) to give 3.47 g of the product (along with another 1.28 g of partially purified product). Mass Spec.: MH$^+$=554.

¹H NMR (CDCl₃, 300 MHz): 8.5 (s, 1H); 7.5 (s, 1H); 7.15 (s, 1H); 4.5 (s, 2H); 4.15 (m, 3H); 3.8 (br s, 2H); 3.4–3.1 (m, 4H); 9–2.75 (m, 1H); 2.7–2.5 (m, 2H); 2.4–2.2 (m, 2H); 1.25 (m, 3H).

Step D:

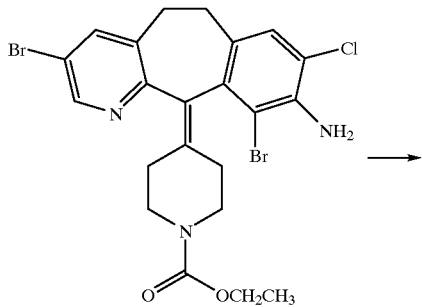

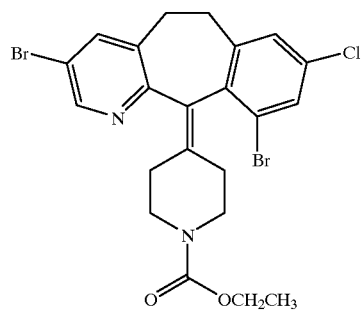

Combine 0.557 g (5.4 mmol) of t-butylnitrite and 3 mL of DMF, and heat the mixture at 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with CH₂Cl₂, dry the extract over MgSO₄ and concentrate in vacuo to a residue. Chromatograph the residue (silica gel, 10%–20% EtOAc/hexane) to give 0.74 g of the product. Mass Spec.: MH⁺=539.0.

¹H NMR (CDCl3, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

Step E:

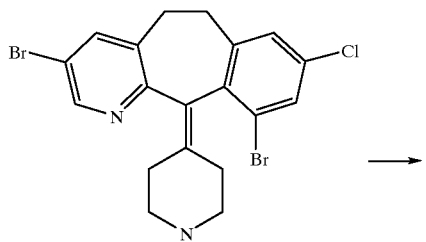

-continued

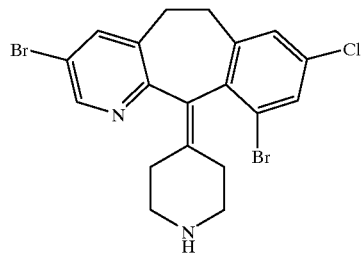

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with CH₂Cl₂. Dry the extract over MgSO₄ and concentrate in vacuo to give 0.59 g of the title compound. Mass Spec.: MH⁺=467. m.p.=123.9°–124.2° C.

PREPARATIVE EXAMPLE 8

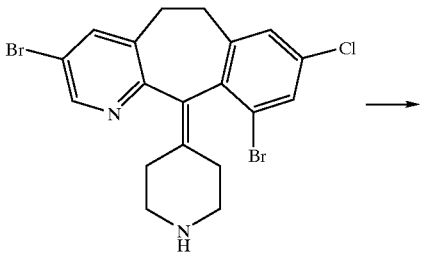

[racemic as well as (+)- and (−)-enantiomers]

Step A:

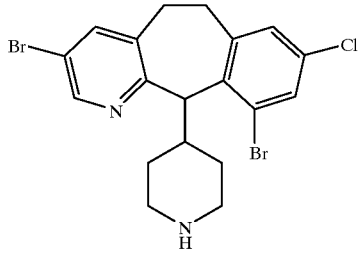

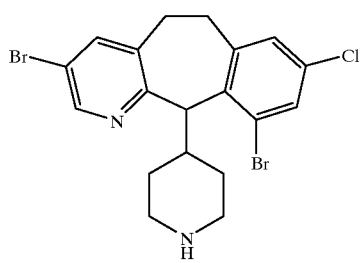

Prepare a solution of 8.1 g of the title compound from Preparative Example 7 in toluene and add 17.3 mL of a 1M solution of DIBAL in toluene. Heat the mixture at reflux and slowly add (dropwise) another 21 mL of 1 M DIBAL/toluene solution over a period of 40 min. Cool the reaction mixture to about 0° C. and add 700 mL of 1 M HCl (aqueous). Separate and discard the organic phase. Wash the aqueous phase with CH₂Cl₂, discard the extract, then basify the aqueous phase by adding 50% NaOH (aqueous). Extract with CH₂Cl₂, dry the extract over MgSO₄ and concentrate in vacuo to give 7.30 g of the title compound, which is a racemic mixture of enantiomers. MH+=469.

Step B - Separation of Enantiomers:

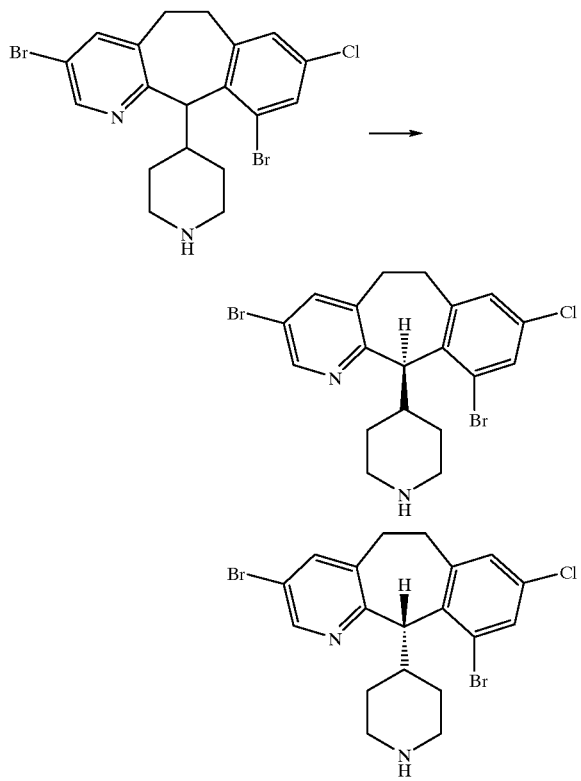

The racemic title compound of Step A is separated by preparative chiral chromatography (Chiralpack AD, 5 cm×50 cm column, using 20% iPrOH/hexane+0.2% diethylamine), to give the (+)-enantiomer and the (−)-enantiomer of the title compound.

Physical chemical data for (+)-enantiomer: m.p.=148.8° C.; Mass Spec. MH+=469; $[\alpha]_D^{25}$=+65.6° (12.93 mg/2 mL MeOH).

Physical chemical data for (−)-enantiomer: m.p.=112° C.; Mass Spec. MH+=469; $[\alpha]_D^{25}$=−65.2° (3.65 mg/2 mL MeOH).

PREPARATIVE EXAMPLE 9

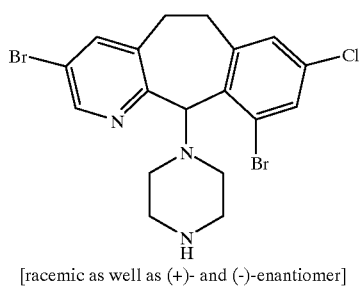

[racemic as well as (+)- and (−)-enantiomer]

Step A:

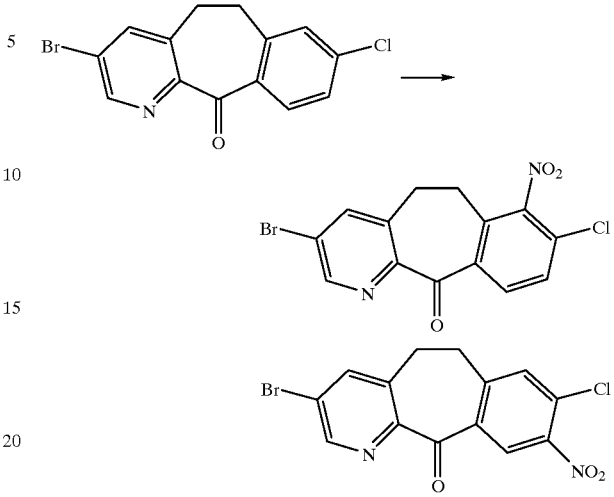

Combine 40.0 g (0.124 mole) of the starting ketone and 200 mL of $H_2SO_4$ and cool to 0° C. Slowly add 13.78 g (0.136 mole) of $KNO_3$ over a period of 1.5 hrs., then warm to room temperature and stir overnight. Work up the reaction using substantially the same procedure as described for Preparative Example 4, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds. MH+ (9-nitro)=367.

Step B:

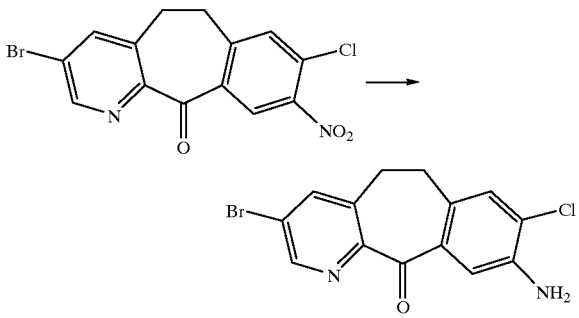

React 28 g (76.2 mmol) of the 9-nitro product of Step A, 400 mL of 85% EtOH/water, 3.8 g (34.3 mmol) of $CaCl_2$ and 38.28 g (0.685 mole) of Fe using substantially the same procedure as described for Preparative Example 4, Step C, to give 24 g of the product. MH+=337.

Step C:

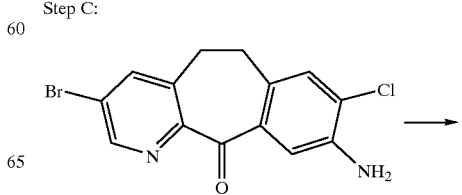

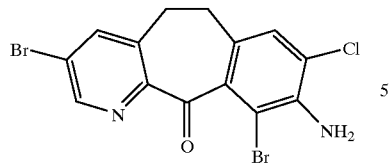

Combine 13 g (38.5 mmol) of the product of Step B, 140 mL of HOAc and slowly add a solution of 2.95 mL (57.8 mmol) of Br$_2$ in 10 mL of HOAc over a period of 20 min. Stir the reaction mixture at room temperature, then concentrate in vacuo to a residue. Add CH$_2$Cl$_2$ and water, then adjust to pH=8–9 with 50% NaOH (aqueous). Wash the organic phase with water, then brine and dry over Na$_2$SO$_4$. Concentrate in vacuo to give 11.3 g of the product.

$^1$H NMR (200 MHZ, CDCl$_3$): 8.73 (d, 1H); 7.74 (d, 1H); 7.14 (s, 1H); 4.63 (s, 2H); 3.23–3.15 (m, 2H); and 3.07–2.98 (m, 2H).

Step D:

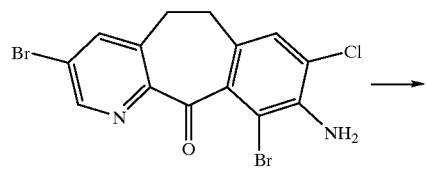

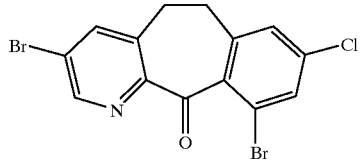

Cool 100 mL of concentrated HCl (aqueous) to 0° C., then add 5.61 g (81.4 mmol) of NaNO$_2$ and stir for 10 min. Slowly add (in portions) 11.3 g (27.1 mmol) of the product of Step C and stir the mixture at 0°–3° C. for 2.25 hrs. Slowly add (dropwise) 180 mL of 50% H$_3$PO$_2$ (aqueous) and allow the mixture to stand at 0° C. overnight. Slowly add (dropwise) 150 mL of 50% NaOH over 30 min., to adjust to pH=9, then extract with CH$_2$Cl$_2$. Wash the extract with water, then brine and dry over Na$_2$SO$_4$. Concentrate in vacuo to a residue and chromatograph (silica gel, 2% EtOAc/CH$_2$Cl$_2$) to give 8.6 g of the product. MH$^+$=399.9.

$^1$H NMR (200 MHZ, CDCl$_3$): 8.75 (d, 1H); 7.77 (d, 1H); 7.56 (d, 1H); 7.21 (d, 1H); and 3.3–3.0 (m, 4H).

Step E:

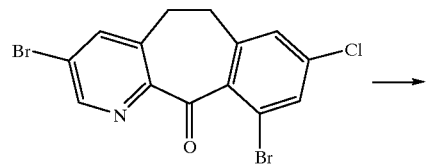

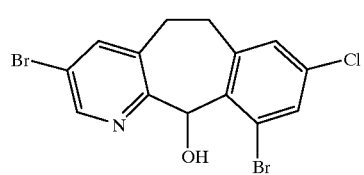

Combine 8.6 g (21.4 mmol) of the product of Step D and 300 mL of MeOH and cool to 0°–2° C. Add 1.21 g (32.1 mmol) of NaBH$_4$ and stir the mixture at ~0° C. for 1 hr. Add another 0.121 g (3.21 mmol) of NaBH$_4$, stir for 2 hr. at 0° C., then let stand overnight at 0° C. Concentrate in vacuo to a residue then partition the residue between CH$_2$Cl$_2$ and water. Separate the organic phase and concentrate in vacuo (50° C.) to give 8.2 g of the product.

$^1$H NMR (200 MHZ, CDCl$_3$): 8.44 (d, 1H); 7.63 (d, 1H); 7.47 (d, 1H); 7.17 (d, 1H); 6.56 (d, 1H); 4.17–4.0 (m, 1H); 7.39 (d, 1H); 3.46–3.3 (m, 1H); 3.05–2.74 (m, 2H).

Step F:

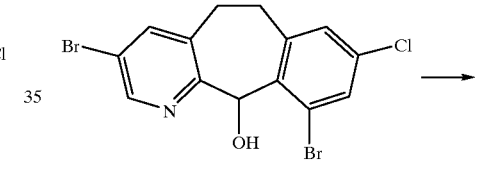

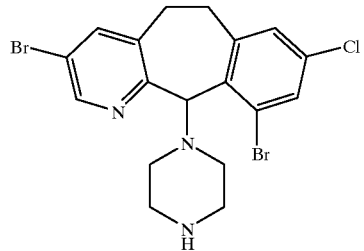

Combine 8.2 g (20.3 mmol) of the product of Step E and 160 mL of CH$_2$Cl$_2$, cool to 0° C., then slowly add (dropwise) 14.8 mL (203 mmol) of SOCl$_2$ over a 30 min. period. Warm the mixture to room temperature and stir for 4.5 hrs., then concentrate in vacuo to a residue, add CH$_2$Cl$_2$ and wash with 1 N NaOH (aqueous) then brine and dry over Na$_2$SO$_4$. Concentrate in vacuo to a residue, then add dry THF and 8.7 g (101 mmol) of piperazine and stir at room temperature overnight. Concentrate in vacuo to a residue, add CH$_2$Cl$_2$, and wash with 0.25 N NaOH (aqueous), water, then brine.

Dry over Na$_2$SO$_4$ and concentrate in vacuo to give 9.46 g of the crude product. Chromatograph (silica gel, 5% MeOH/CH$_2$Cl$_2$+NH$_3$) to give 3.59 g of the title compound, as a racemate. $^1$H NMR (CDCl$_3$, 200 MHz): 8.43 (d, 1H); 7.55 (d, 1H); 7.45 (d, 1H); 7.11 (d, 1H); 5.31 (s, 1H); 4.86–4.65 (m, 1H); 3.57–3.40 (m, 1H); 2.98–2.55 (m, 6H); 2.45–2.20 (m, 5H). MH$^+$=470.

Step G - Separation of Enantiomers:

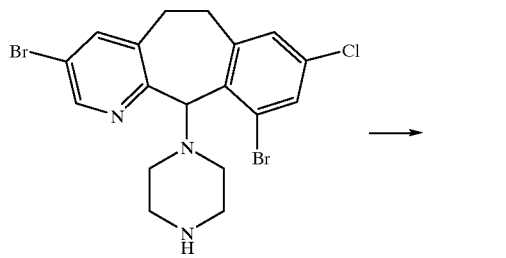

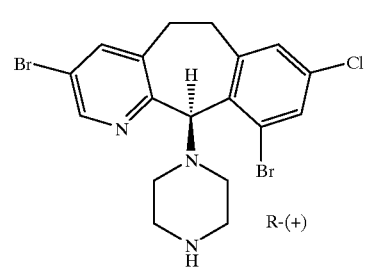

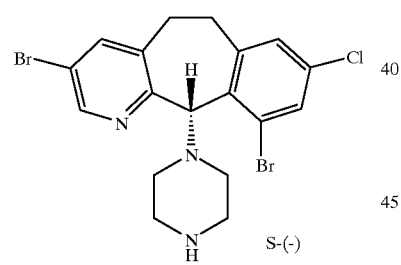

The racemic title compound from Step F (5.7 g) is chromatographed as described for Preparative Example 6, Step D, using 30% iPrOH/hexane+0.2% diethylamine, to give 2.88 g of the R-(+)-enantiomer and 2.77 g of the S-(−)-enantiomer of the title compound.

Physical chemical data for the R-(+)-enantiomer: Mass Spec. MH$^+$=470; $[\alpha]_D^{25}$=+12.1° (10.9 mg/2 mL MeOH).

Physical chemical data for the S-(−)-enantiomer: Mass Spec. MH$^+$=470; $[\alpha]_D^{25}$=−13.2° (11.51 mg/2 mL MeOH).

PREPARATIVE EXAMPLE 10

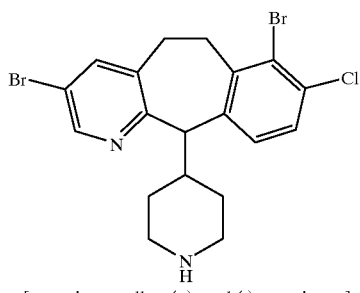

[racemic as well as (+)- and (−)-enantiomer]

Step A:

Combine 13 g (33.3 mmol) of the title compound from Preparative Example 4, Step D, and 300 mL of toluene at 20° C., then add 32.5 mL (32.5 mmol) of a 1 M solution of DIBAL in toluene. Heat the mixture at reflux for 1 hr., cool to 20° C., add another 32.5 mL of 1 M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with CH$_2$Cl$_2$ (3×200 mL), dry the organic layers over MgSO$_4$, then concentrate in vacuo to a residue. Chromatograph (silica gel, 12% MeOH/CH$_2$Cl$_2$+4% NH$_4$OH) to give 10.4 g of the title compound as a racemate. Mass Spec.: MH$^+$=469 (FAB). partial $^1$H NMR (CDCl$_3$, 400 MHz): 8.38 (s, 1H); 7.57 (s, 1H); 7.27 (d, 1H); 7.06 (d, 1H); 3.95 (d, 1H).

Step B - Separation of Enantiomers:

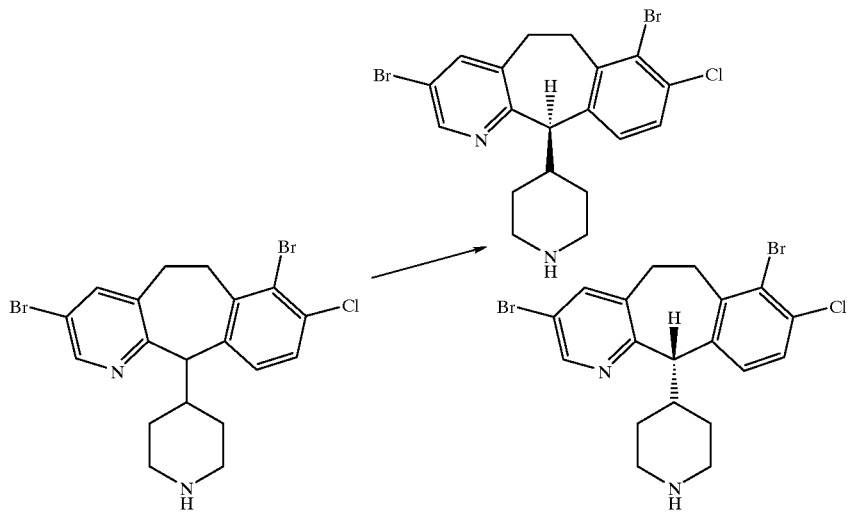

The racemic title compound of Step A is separated by preparative chiral chromatography (Chiralpack AD, 5 cm×50 cm column, using 5% iPrOH/hexane+0.2% diethylamine), to give the (+)-enantiomer and the (−)-enantiomer of the title compound.

Physical chemical data for (+)-enantiomer: Mass Spec. MH⁺=469 (FABS); $[\alpha]_D^{25}$=+43.5° (c=0.402, EtOH); partial ¹H NMR (CDCl₃, 400 MHz): 8.38 (s, 1H); 7.57 (s, 1H); 7.27 (d, 1H); 7.05 (d, 1H); 3.95 (d, 1H).

Physical chemical data for (−)-enantiomer: Mass Spec. MH⁺=469 (FAB); $[\alpha]_D^{25}$=−41.8° (c=0.328 EtOH); partial ¹H NMR (CDCl₃, 400 MHz): 8.38 (s, 1H); 7.57 (s, 1H); 7.27 (d, 1H); 7.05 (d, 1H); 3.95 (d, 1H).

PREPARATIVE EXAMPLE 11

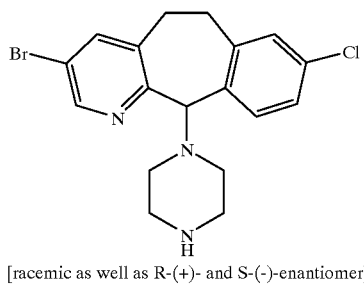

[racemic as well as R-(+)- and S-(−)-enantiomer]

Treat 4-(8-chloro-3-bromo-5,6-dihydro-11H-benzo[5,6]cyclohepta[1,2-b]pyridin-11-ylidene)-1-piperidine-1-carboxylic acid ethyl ester via substantially the same procedure as described in Preparative Example 6, Steps A–D, to give as the product of Step C, the racemic title compound, and as the products of Step D the R-(+)-enantiomer and S-(−)-enantiomer of the title compound.

Physical chemical data for the R-(+)-enantiomer: ¹³C NMR (CDCl₃): 155.8 (C); 146.4 (CH); 140.5 (CH); 140.2 (C); 136.2 (C); 135.3 (C); 133.4 (C); 132.0 (CH); 129.9 (CH); 125.6 (CH); 119.3 (C); 79.1 (CH); 52.3 (CH₂); 52.3 (CH₂); 45.6 (CH₂); 45.6 (CH₂); 30.0 (CH₂); 29.8 (CH₂). $[\alpha]_D^{25}$=+25.8° (8.46 mg/2 mL MeOH).

Physical chemical data for the S-(−)-enantiomer: ¹³C NMR (CDCl₃): 155.9 (C); 146.4 (CH); 140.5 (CH); 140.2 (C); 136.2 (C); 135.3 (C); 133.3 (C); 132.0 (CH); 129.9 (CH); 125.5 (CH); 119.2 (C); 79.1 (CH); 52.5 (CH₂); 52.5 (CH₂); 45.7 (CH₂); 45.7 (CH₂); 30.0 (CH₂); 29.8 (CH₂). $[\alpha]_D^{25}$=−27.9° (8.90 mg/2 mL MeOH).

EXAMPLE 1

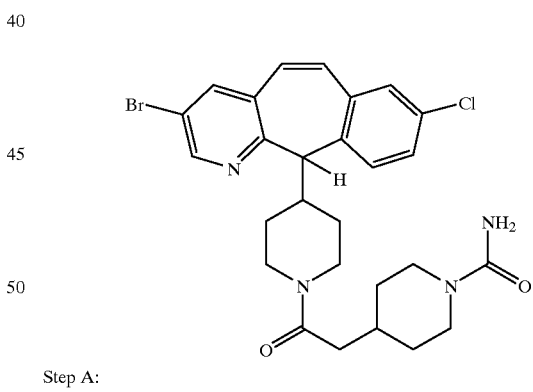

Step A:

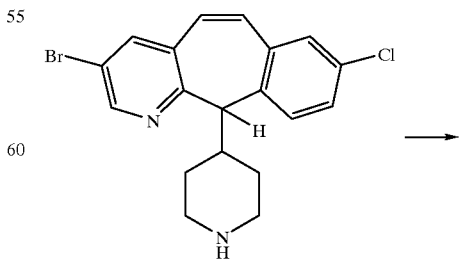

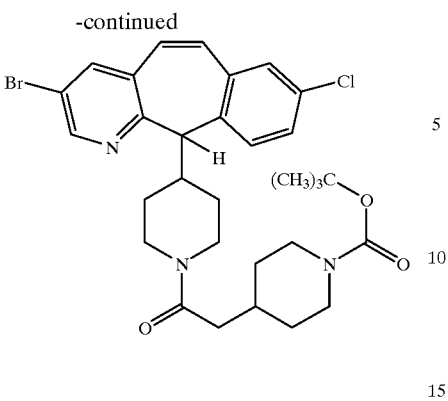

Dissolve 1.160 g (2.98 mmol) of the title compound from Preparative Example 3 in 20 mL of DMF, stir at room temperature, and add 0.3914 g (3.87 mmol) of 4-methylmorpholine, 0.7418 g (3.87 mmol) of DEC, 0.5229 g (3.87 mmol) of HOBT, and 0.8795 g (3.87 mmol) of 1-N-t-butoxycarbonylpiperidinyl-4-acetic acid. Stir the mixture at room temperature for 2 days, then concentrate in vacuo to a residue and partition the residue between CH$_2$Cl$_2$ and water. Wash the organic phase successively with saturated NaHCO$_3$ (aqueous), 10% NaH$_2$PO$_4$ (aqueous) and brine. Dry the organic phase over MgSO$_4$, filter and concentrate in vacuo to a residue. Chromatograph the residue (silica gel, 2% MeOH/CH$_2$Cl$_2$+NH$_3$) to give 1.72 g of the product. m.p.=94.0–94.5° C., Mass Spec.: MH$^+$=614.

Elemental analysis: calculated—C, 60.54; H, 6.06; N, 6.83 found—C, 59.93; H, 6.62; N, 7.45.

Step B:

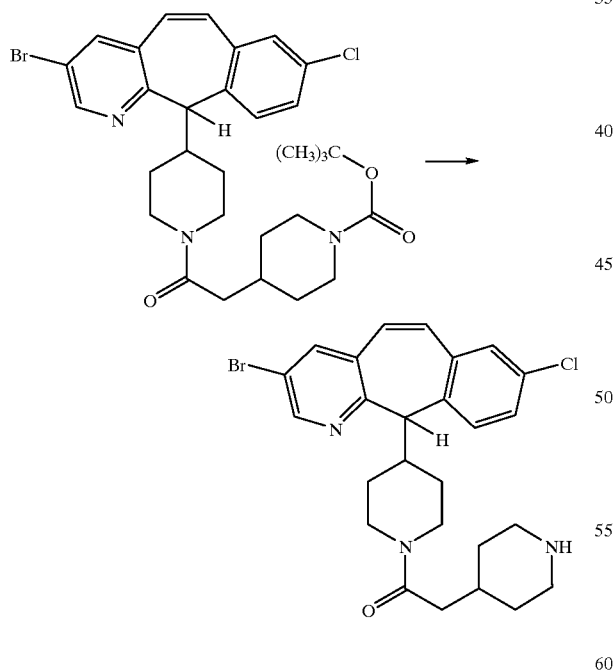

Combine 1.67 g (2.7 mmol) of the product of Step A and 20 mL of CH$_2$Cl$_2$ and stir at 0° C. Add 20 mL of TFA, stir the mixture for 2 hours, then basify the mixture with 1 N NaOH (aqueous). Extract with CH$_2$Cl$_2$, dry the organic phase over MgSO$_4$, filter and concentrate in vacuo to give 1.16 g of the product. m.p.=140.2–140.8° C., Mass Spec.: MH$^+$=514.

Step C:

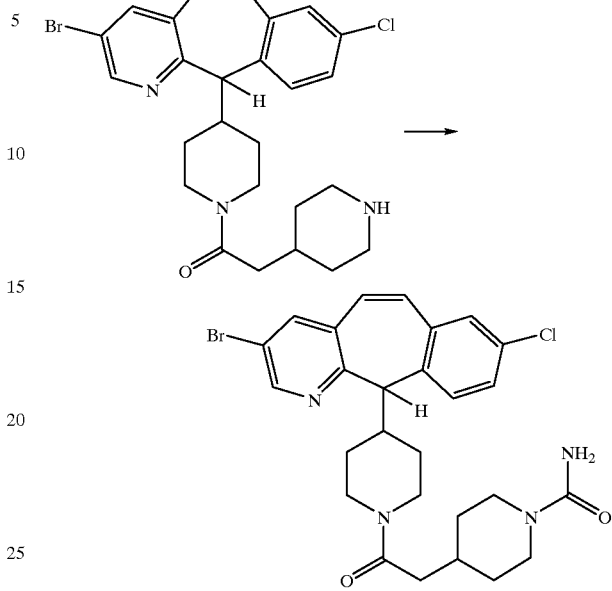

Combine 0.50 g of the product of Step B, 20 mL of CH$_2$Cl$_2$ and 4.5 equivalents of (CH$_3$)$_3$SiNCO and stir at room temperature for 3 hours. Extract the mixture with saturated NaHCO$_3$ (aqueous) and dry the organic phase over MgSO$_4$. Filter and concentrate in vacuo to give 0.8 g of the crude product. Chromatograph the crude product (silica gel, 5% MeOH/CH$_2$Cl$_2$+NH$_3$) to give 0.26 g of the product. m.p.=170.2–170.5° C., Mass Spec.: MH$^+$=557.

EXAMPLE 2

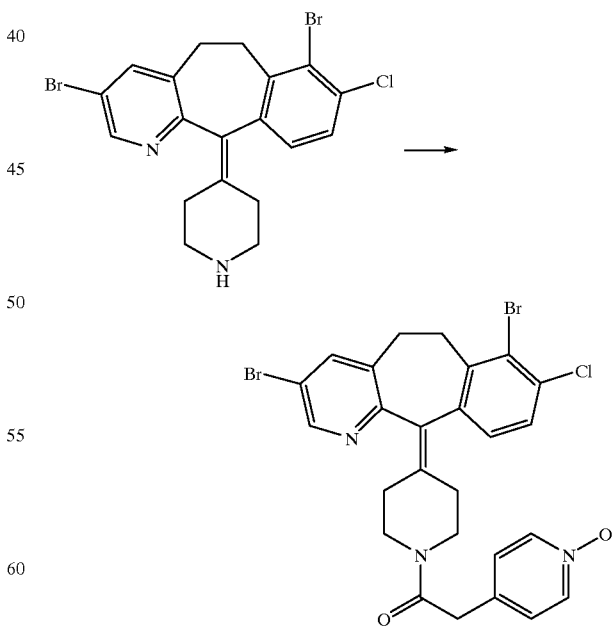

Combine 0.5 g (1.06 mmol) of the title compound of Preparative Example 4, 0.4 g (2.61 mmol) of the title compound of Preparative Example 1, 5 mL of dry DMF, and 0.5 mL (4.53 mmol) of 4-methylmorpholine, at 0° C., then add 0.6 g (3.12 mmol) of DEC and 0.4 g (2.96 mmol) of HOBT and stir the mixture overnight at 20° C. Concentrate in vacuo to a residue and extract the residue with CH$_2$Cl$_2$ (2×50 mL). Wash the extracts with 25 mL of water, dry over MgSO$_4$, then concentrate in vacuo to a residue and chromatograph (silica gel, 10% MeOH/EtOAc+2% NH$_4$OH (aqueous)) to give 0.6 g (93.7% yield) of the title compound. Mass Spec.: MH$^+$=602 (FABS); partial $^1$H NMR (CDCl$_3$, 300 MHz): 8.48 (s, 1H); 8.16 (d, 2H); 7.61 (s, 1H); 7.29 (m, 1H); 7.18 (d, 2H); 7.04 (d, 1H); 3.71 (s, 2H).

Elemental analysis: calculated—C, 48.81; H, 4.10; N, 6.57 found—C, 49.10; H, 3.79; N, 6.74.

EXAMPLE 3

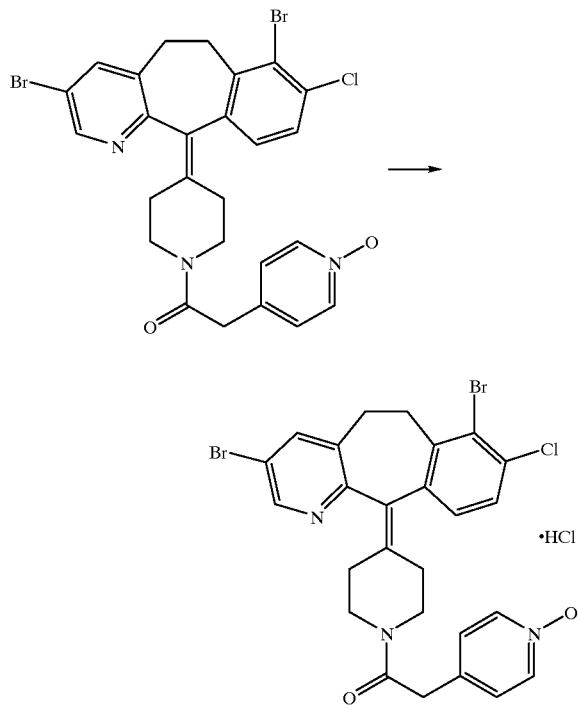

Dissolve 5.9 g (9.78 mmol) of the title compound of Example 2 in 300 mL of 1:5 CH$_2$Cl$_2$/EtOAc at 0° C. Slowly add (dropwise) 3 mL of 4 N HCl (aqueous) and stir the mixture at 0° C. for 5 min. Add 200 mL of Et$_2$O, collect the resulting solids by filtration and wash the solids with 50 mL of Et$_2$O. Dry the solids at 20° C. and 0.2 mm Hg to give 5.9 g (96% yield) of the title compound. Mass Spec.: MH$^+$=602 (FAB). partial $^1$H NMR (DMSO-d$_6$, 300 MHz): δ8.66 (d, 2H); 8.51 (s, 1H); 7.95 (s, 1H); 7.67 (d, 2H); 7.47 (m, 1H); 7.15 (m, 1H); 3.99 (s, 2H).

Elemental analysis: calculated—C, 48.77; H, 3.62; N, 6.56 found—C, 48.34; H, 3.95; N, 6.84.

EXAMPLE 4

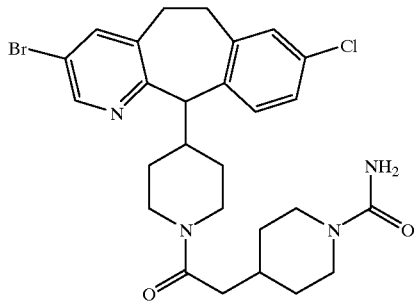

Step A:

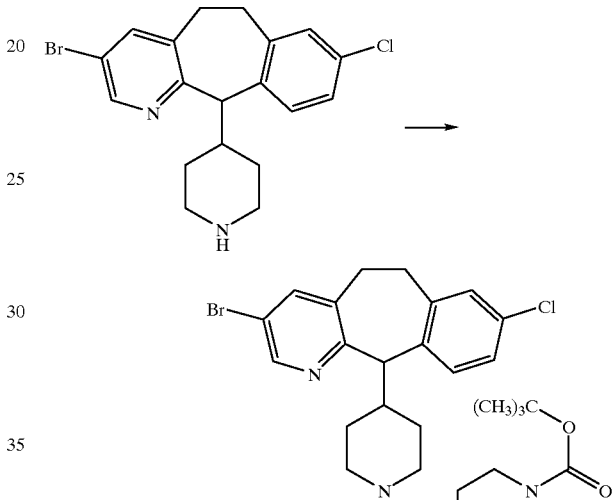

Combine 0.501 g (1.28 mmol) of the title compound of Preparative Example 5 and 20 mL of dry DMF, then add 0.405 g (1.664 mmol) of 1-N-t-butoxycarbonylpiperidinyl-4-acetic acid, 0.319 g (1.664 mmol) of DEC, 0.225 g (1.664 mmol) of HOBT, and 0.168 g (1.664 mmol) of 4-methylmorpholine and stir the mixture at room temperature overnight. Concentrate the mixture in vacuo to a residue, then partition the residue between 150 mL of CH$_2$Cl$_2$ and 150 mL of saturated NaHCO$_3$ (aqueous). Extract the aqueous phase with another 150 mL of CH$_2$Cl$_2$. Dry the organic phase over MgSO$_4$, and concentrate in vacuo to a residue. Chromatograph the residue (silica gel, 500 mL hexane, 1 L of 1% MeOH/CH$_2$Cl$_2$+0.1% NH$_4$OH (aqueous), then 1 L of 2% MeOH/CH$_2$Cl$_2$+0.1% NH$_4$OH (aqueous)) to give 0.575 g of the product. m.p.=115°–125° C.; Mass Spec.: MH$^+$=616.

Step B:

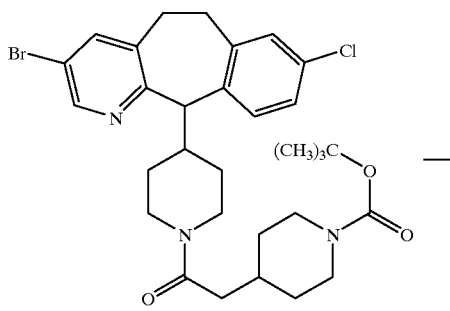

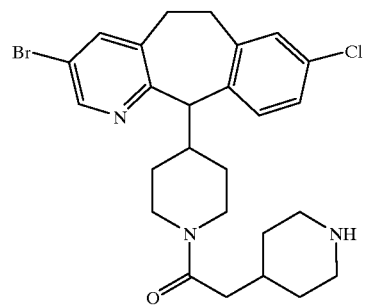

Combine 0.555 g (0.9 mmol) of the product of Step A and 15 mL of CH₂Cl₂ and cool the mixture to 0° C. Add 15 mL of TFA and stir at 0° C. for 2 hours. Concentrate in vacuo at 40–45° C. to a residue, then partition the residue between 150 mL of CH₂Cl₂ and 100 mL of saturated NaHCO₃ (aqueous). Extract the aqueous layer with 100 mL of CH₂Cl₂, combine the extracts and dry over MgSO₄. Concentrate in vacuo to give 0.47 g of the product. m.p.=140°–150° C.; Mass Spec.: MH⁺=516.

Step C:

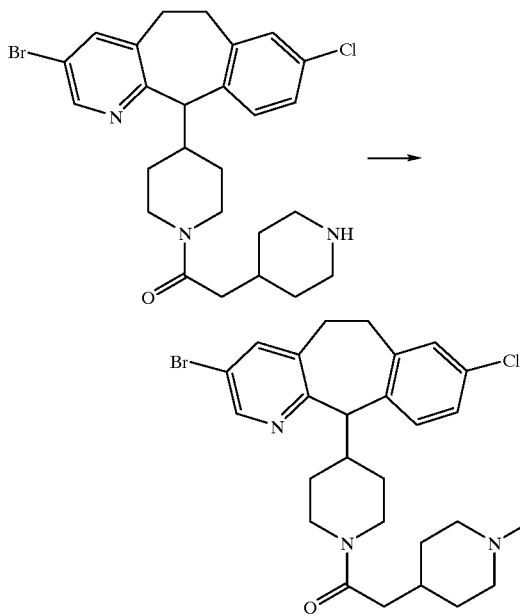

Combine 0.449 g (0.87 mmol) of the product of Step B, 20 mL of CH₂Cl₂ and 0.501 g (0.59 mmol) of (CH₃)₃SiNCO and stir at room temperature overnight. Add 50–75 mL of saturated NaHCO₃ (aqueous) and stir for 0.5 hours. Dilute with CH₂Cl₂, separate the layers and extract the aqueous layer with 2×100 mL of CH₂Cl₂. Dry the combined CH₂Cl₂ extracts over MgSO₄ and concentrate in vacuo to a residue. Chromatograph the residue (silica gel, 500 mL CH₂Cl₂; 1 L of 1% MeOH/CH₂Cl₂+0.1% NH₄OH; 1 L of 2% MeOH/CH₂Cl₂+0.2% NH₄OH; then with 3% MeOH/CH₂Cl₂+0.3% NH₄OH) to give 0.33 g of the title compound. m.p.=145°–155° C.; Mass Spec.: MH⁺=559.

EXAMPLE 5

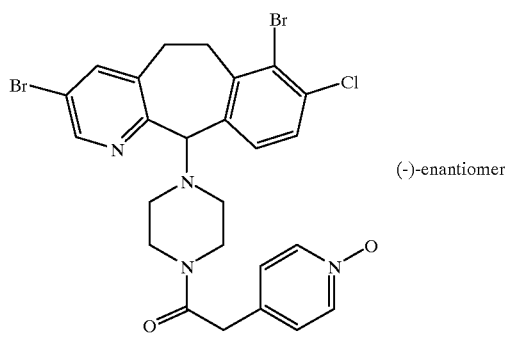

(-)-enantiomer

Combine 3.0 g (6.36 mmol) of the (–)-enantiomer of the title compound from Preparative Example 6, Step D, and 70 mL of dry DMF. Add 3.84 mL (34.94 mmol) of N-methylmorpholine, 3.28 g (17.11 mmol) of DEC, 2.23 g (16.52 mmol) of HOBT and 2.09 (13.55 mmol) of 4-pyridylacetic acid N-oxide from Preparative Example 1 and stir the mixture at room temperature overnight. Concentrate in vacuo to remove the DMF, add 100 mL of saturated NaHCO₃ (aqueous) and 10 mL of CH₂Cl₂ and stir for 15 min. Extract the mixture with CH₂Cl₂ (2×500 mL), dry the extracts over MgSO₄ and concentrate in vacuo to a residue. Chromatograph the residue (500 g reverse phase C18 silica, gradient of 75%, 80%, then 85% MeOH/water+ 0.1% HOAc). Concentrate the desired fractions in vacuo to remove MeOH and add 50 mL of 1 M NaOH (aqueous). Stir for 15 min., then extract with CH₂Cl₂ (2×500 mL). Dry the extract over MgSO₄ and concentrate in vacuo to give 3.4 g of the title compound. m.p.=148.9°–150.5° C.; $[\alpha]_D^{25}$=–56.37° (9.4 mg/2 mL MeOH); Mass Spec. MH⁺=605.

The title compound of Example 5 can also be isolated as its HCl salt by treating a solution of the product in HCl and CH₂Cl₂ at room temperature, followed by concentration in vacuo to give the HCl salt. $[\alpha]_D^{25}$=–31.90° (4.80 mg/2 mL MeOH +1 mL of water).

Using the (+)-enantiomer of the product of Preparative Example 6 and following essentially the same procedure as described above for Example 5, the analogous (+)-enantiomer (Example 5A), i.e., the enantiomer of the title compound of Example 5, is prepared. m.p.=149.0°–150.5° C.; Mass Spec.: MH⁺=605; $[\alpha]_D^{25}$=+67.1° (7.0 mg/2 mL MeOH).

The title compound of Example 5A can also be isolated as its HCl salt as described above for Example 5. m.p.=152.9° C. (dec.); $[\alpha]_D^{25}$=+41.7° (2 mL MeOH+1 mL of water).

Using the racemic title compound of Preparative Example 6, Step C, and following essentially the same procedure as described above for Example 5, the racemate (Example 5B), is prepared. m.p.=84.3°–85.6° C.; Mass Spec.: MH⁺=607.

EXAMPLE 6

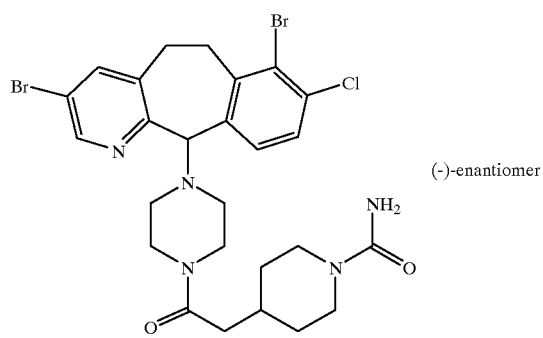
(-)-enantiomer

Step A:

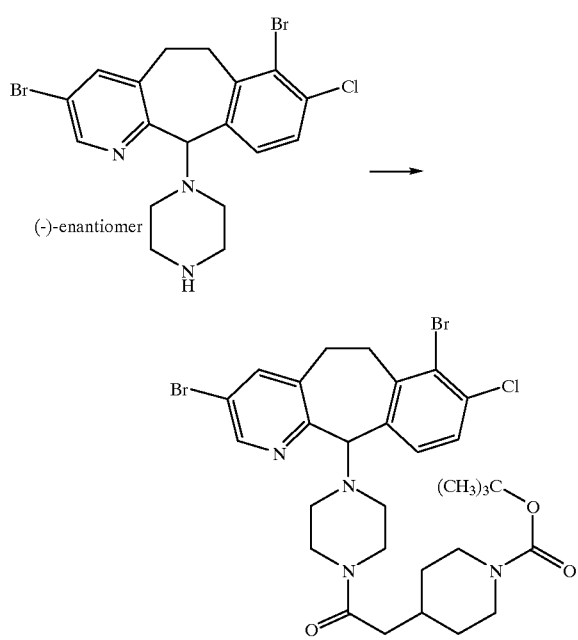

Combine 3.21 g (6.80 mmol) of the (–)-enantiomer product of Preparative Example 6 and 150 mL of anhydrous DMF. Add 2.15 g (8.8 mmol) of 1-N-t-butoxycarbonylpiperidinyl-4-acetic acid, 1.69 g (8.8 mmol) of DEC, 1.19 g (8.8 mmol) of HOBT and 0.97 mL (8.8 mmol) of N-methylmorpholine and stir the mixture at room temperature overnight. Concentrate in vacuo to remove the DMF and add 50 mL of saturated NaHCO$_3$ (aqueous). Extract with CH$_2$Cl$_2$ (2×250 mL), wash the extracts with 50 mL of brine and dry over MgSO$_4$. Concentrate in vacuo to a residue and chromatograph (silica gel, 2% MeOH/CH$_2$Cl$_2$+10% NH$_4$OH) to give 4.75 g of the product. m.p.=75.7°–78.5° C.; Mass Spec.: MH$^+$=695; $[\alpha]_D^{25}$=–5.5° (6.6 mg/2 mL MeOH).

Step B:

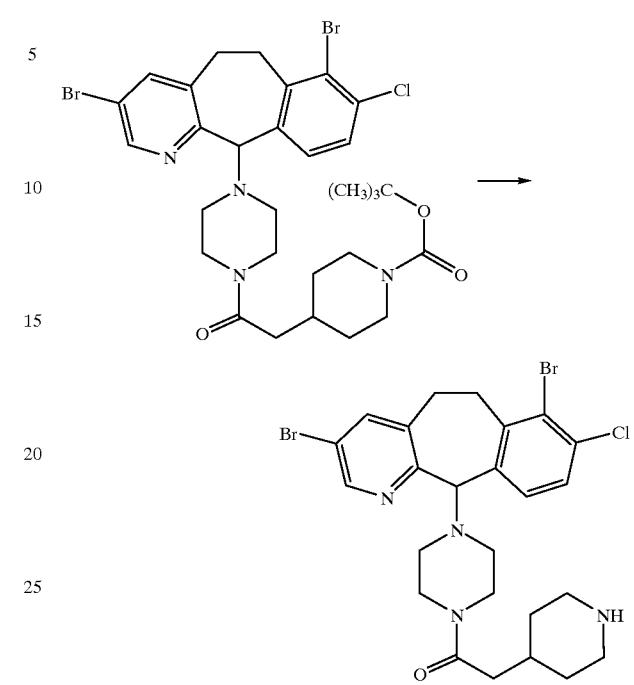

Combine 4.70 g (6.74 mmol) of the product of Step A and 30 mL of MeOH, then add 50 mL of 10% H$_2$SO$_4$/dioxane in 10 mL aliquots over a 1 hr. period. Pour the mixture into 50 mL of water and add 15 mL of 50% NaOH (aqueous) to adjust to pH≈10–11. Filter to remove the resulting solids and extract the filtrate with CH$_2$Cl$_2$ (2×250 mL). Concentrate the aqueous layer in vacuo to remove the MeOH and extract again with 250 mL of CH$_2$Cl$_2$. Dry the combined extracts over MgSO$_4$ and concentrate in vacuo to give the product. m.p.=128.1°–131.5° C.; Mass Spec.: MH$^+$=595; $[\alpha]_D^{25}$=–6.02° (9.3 mg/2 mL MeOH).

Step C:

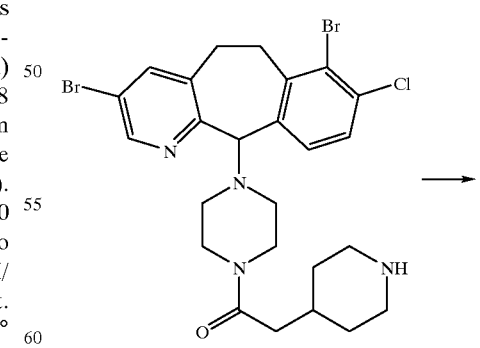

-continued

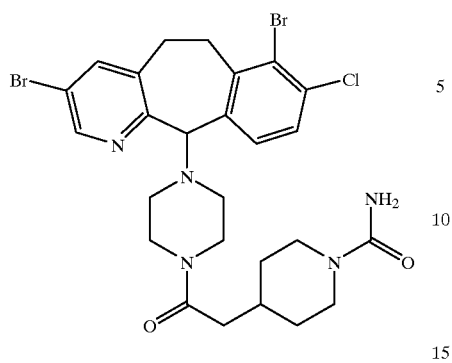

Combine 3.64 g (5.58 mmol) of the product of Step B and 30 mL of CH$_2$Cl$_2$, then add 6.29 mL (44.64 mmol) of (CH$_3$)$_3$SiNCO and stir the mixture for 2 days at room temperature. Add 25 mL of NaHCO$_3$ (aqueous), then extract with CH$_2$Cl$_2$ (2×250 mL). Wash the extracts with 25 mL of brine and dry over MgSO$_4$. Concentrate in vacuo to a residue and chromatograph (silica gel, gradient of 2.5%, 5.0%, then 7.5% MeOH/CH$_2$Cl$_2$+10% NH$_4$OH) to give the title compound. m.p.=150.5°–153.0° C.; Mass Spec.: MH$^+$= 638; [α]$_D^{25}$=−61.4° (8.18 mg/2 mL MeOH).

EXAMPLE 7

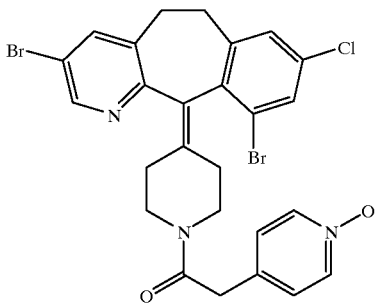

React the title compound of Preparative Example 7 and the title compound of Preparative Example 1 using substantially the same procedure as described for Example 2, to give 0.25 g of the title compound, which is a racemic mixture of atropisomers. Mass Spec.: MH$^+$=602. m.p.=167.2°–167.8° C.

The HCl salt of the title compound of Example 7 is prepared by stirring for 1 hr. with HCl/CH$_2$Cl$_2$, then concentrating in vacuo to give the salt.

Examples 7A & 7B

Example 7A

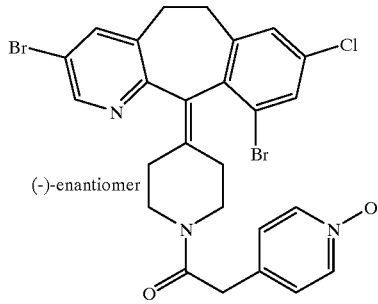

(−)-enantiomer

Example 7B

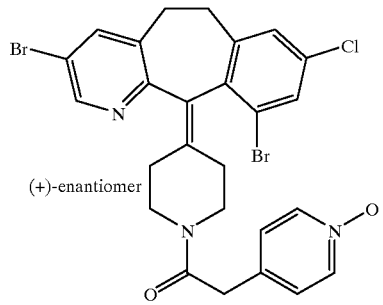

(+)-enantiomer

The title compound of Example 7 is a racemic mixture of atropisomers. Those atropisomers are separated by preparative chromatography (HPLC), using an Chiralpack AD column (5 cm×50 cm) and 40% i-PrOH/hexane+0.2% diethylamine as the mobile phase to give the (+)- and (−)-enantiomers, Examples 7B and 7A, respectively.

Physical chemical data for (−)-enantiomer, Example 7A: m.p.=114.2°–114.8° C.; [α]$_D^{25}$=−154.6° (8.73 mg/2 mL, MeOH).

Physical chemical data for (+)-enantiomer, Example 7B: m.p.=112.6°–113.5° C.; [α]$_D^{25}$=+159.7° (10.33 mg/2 mL, MeOH).

EXAMPLE 8

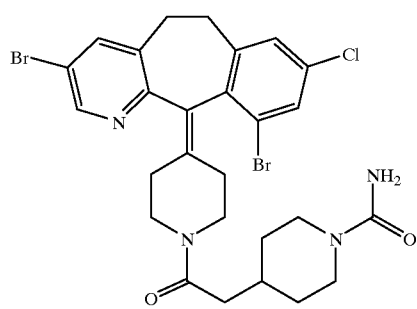

Step A:

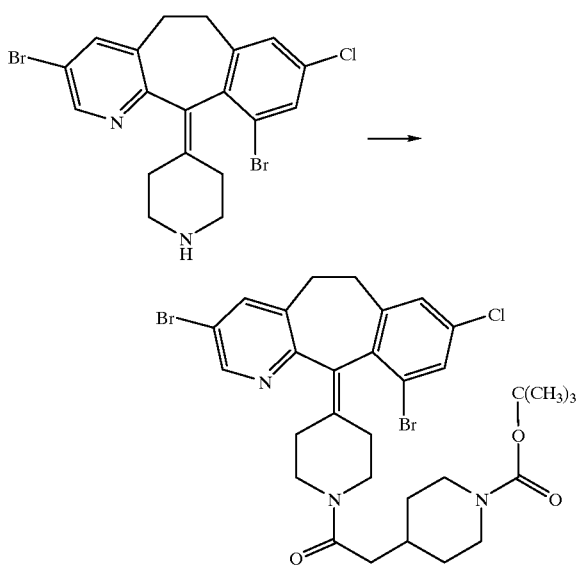

React 6.0 g (12.8 mmol) of the title compound of Preparative Example 7 and with 3.78 g (16.6 mmol) of 1-N-t-butoxycarbonylpiperidinyl-4-acetic acid using substantially the same procedures as described for Example 6, Step A, to give 8.52 g of the product. Mass Spec.: MH$^+$=692 (FAB). $^1$H NMR (CDCl$_3$, 200 MHz): 8.5 (d, 1H); 7.5 (d, 2H); 7.2 (d, 1H); 4.15–3.9 (m, 3H); 3.8–3.6 (m, 1H); 3.5–3.15 (m, 3H); 2.9 (d, 2H); 2.8–2.5 (m, 4H); 2.4–1.8 (m, 6H); 1.8–1.6 (br d, 2H); 1.4 (s, 9H); 1.25–1.0 (m, 2H).

Step B:

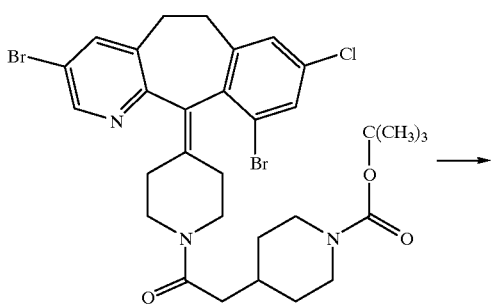

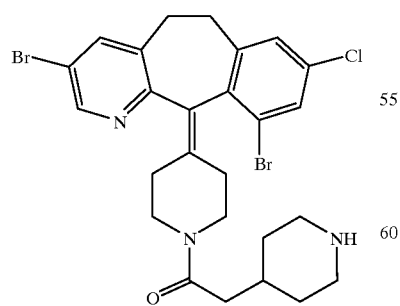

Combine 8.50 g of the product of Step A and 60 mL of CH$_2$Cl$_2$, then cool to 0° C. and add 55 mL of TFA. Stir the mixture for 3 h at 0° C., then add 500 mL of 1 N NaOH (aqueous) followed by 30 mL of 50% NaOH (aqueous). Extract with CH$_2$Cl$_2$, dry over MgSO$_4$ and concentrate in vacuo to give 7.86 g of the product. Mass Spec.: MH$^+$=592 (FAB). $^1$H NMR (CDCl$_3$, 200 MHz): 8.51 (d, 1H); 7.52 (d of d, 2H); 7.20 (d, 1H); 4.1–3.95 (m, 2H); 3.8–3.65 (m, 2H); 3.5–3.05 (m, 5H); 3.0–2.5 (m, 6H); 2.45–1.6 (m, 6H);1.4–1.1 (m, 2H).

Step C:

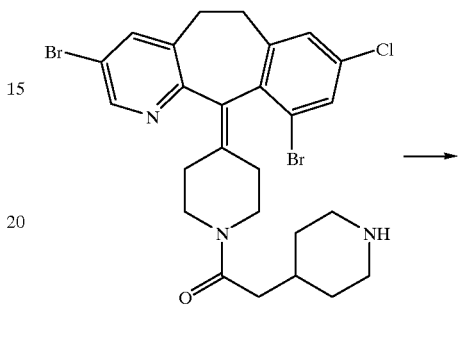

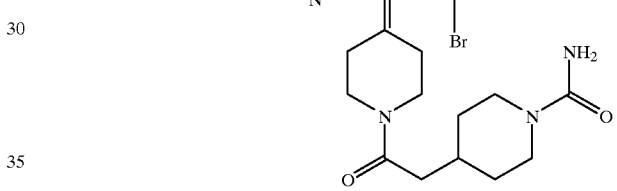

Treat 7.80 g (13.1 mmol) of the product of Step B with 12.1 g (105 mmol) of (CH$_3$)$_3$SiNCO using substantially the same procedure as described for Example 6, Step C, to give 5.50 g of the title compound, which is a racemic mixture of atropisomers. m.p.=163.6°–164.0° C. Mass spec.: MH$^+$=635 (FAB). $^1$H NMR (CDCl$_3$, 200 MHz): 8.5 (d, 1H); 7.52 (d, 1H); 7.48 (d, 1H); 7.21 (d, 1H); 4.54, (s, 2H); 4.1–3.6 (m, 4H); 3.45–3.15 (m, 4H); 3.0–2.5 (m, 5H); 2.45–1.6 (m, 7H); 1.4–1.0, (m, 2H).

Examples 8A & 8B

Example 8A

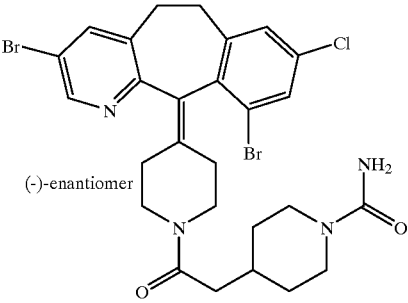

(-)-enantiomer

-continued

Example 8B

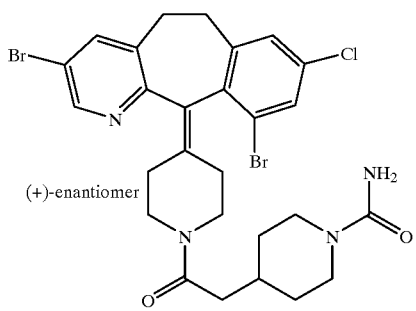

Examples 9A & 9B

Example 9A

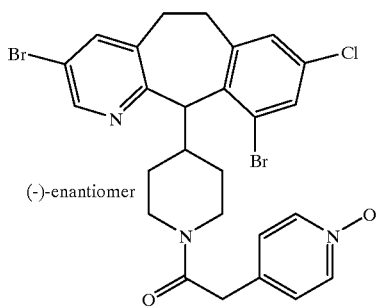

The title compound of Example 8 is a racemic mixture of atropisomers. Those atropisomers are separated by preparative chromatography (HPLC), using an Chiralpack AD column (5 cm×50 cm) and 20% i-PrOH/hexane+0.2% diethylamine as the mobile phase, at a flow rate of 100 mL/min., to give the (+)- and (−)-enantiomers, Examples 8B and 8A, respectively.

Physical chemical data for (−)-enantiomer, Example 8A: m.p.=142.9°–143.5° C.; $[\alpha]_D^{25}$=−151.7° (11.06 mg/2 mL, MeOH).

Physical chemical data for (+)-enantiomer, Example 8B: m.p.=126.5°–127.0° C.; $[\alpha]_D^{25}$=+145.6° (8.38 mg/2 mL, MeOH).

EXAMPLE 9

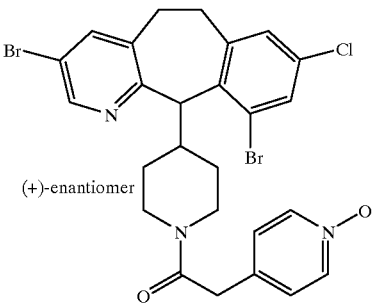

Combine 3.32 g of the (+)-enantiomer of the title compound of Preparative Example 8, Step B, 2.38 g of the title compound of Preparative Example 1, 1.92 g of HOBT, 2.70 g of DEC, 1.56 mL of N-methylmorpholine and 50 mL of dry DMF and stir at 25° C. for 24 hrs. Concentrate in vacuo, then dilute the residue with $CH_2Cl_2$. Wash with 1 N NaOH (aqueous), then with saturated $NaH_2PO_4$ (aqueous) and dry over $MgSO_4$. Concentrate in vacuo to a residue and chromatograph (silica gel, 2% MeOH/$CH_2Cl_2$+$NH_4OH$) to give 3.82 g of the title compound. Mass Spec.: $MH^+$=604 (FAB).

The hydrochloride salt was prepared by dissolution of the title compound from Example 9 in dichloromethane saturated with hydrogen chloride. Concentration in vacuo provided the title compound from Example 9 as the HCl salt. m.p.=166.5° C.; $[\alpha]_D^{22}$=+70.8° (9.9 mg/2 mL MeOH).

Example 9B

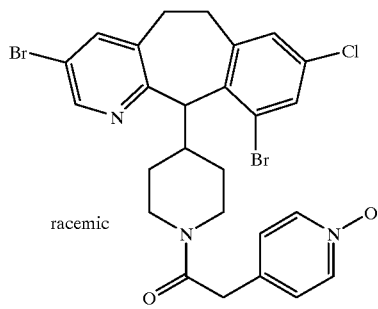

The (−)-enantiomer of the title compound of Preparative Example 8, Step B, (3.38 g) is reacted with 2.20 g of the title compound of Preparative Example 1, via substantially the same procedure as described for Example 9 to give 3.58 g of the title compound of Example 9A.

The HCl salt of the title compound of Example 9A is prepared by dissolving of the title compound in $CH_2Cl_2$, adding 6M HCl (g) in $CH_2Cl_2$, then concentrating in vacuo to give the salt. m.p.=129° C.; $[\alpha]_D^{25}$=−72.3° (3.32 mg/2 mL MeOH).

The racemic title compound of Preparative Example 8, Step A, is reacted with the title compound of Preparative Example 1, via substantially the same procedure as described for Example 9 to give the title compound of Example 9B. m.p.=145.0° C.

EXAMPLE 10

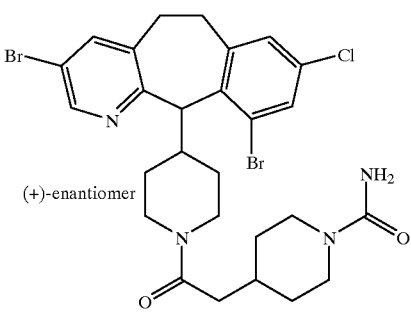

Step A:

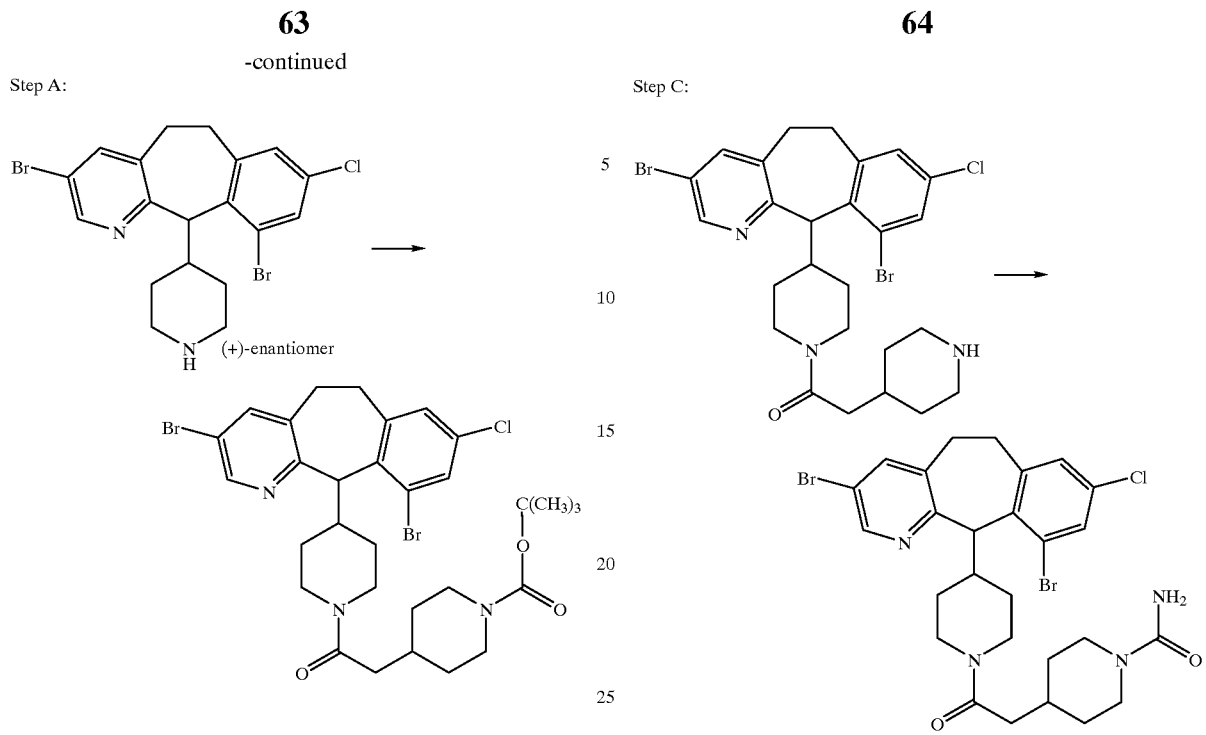

React 1.33 g of the (+)-enantiomer of the title compound of Preparative Example 8, Step B, with 1.37 g of 1-N-t-butoxycarbonylpiperidinyl-4-acetic acid using substantially the same procedures as described for Example 6, Step A, to give 2.78 g of the product. Mass Spec.: MH$^+$=694.0 (FAB); $[\alpha]_D^{25}$=+34.1° (5.45 mg/2 mL, MeOH).

Step B:

Treat 2.78 g of the product of Step A via substantially the same procedure as described for Example 8, Step B, to give 1.72 g of the product. m.p.=104.1° C.; Mass Spec.: MH$^+$=594; $[\alpha]_D^{25}$=+53.4° (11.42 mg/2 mL, MeOH).

Step C:

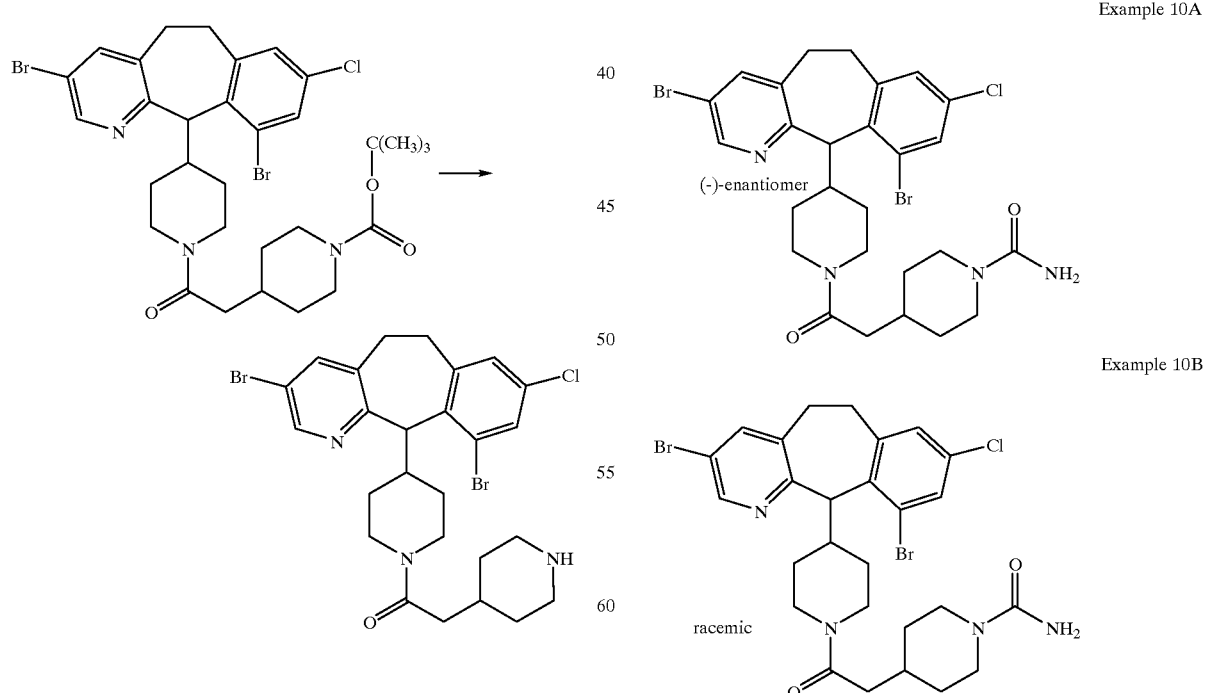

Treat 1.58 g of the product of Step B with 6 mL of $(CH_3)_3SiNCO$ using substantially the same procedure as described for Example 6, Step C, to give 1.40 g of the title compound. m.p.=140° C.; Mass spec.: MH$^+$=637; $[\alpha]_D^{25}$=+49.1° (4.24 mg/2 mL, MeOH).

Recrystallization from acetone provided the title compound as a solid. m.p.=214.5–215.9° C.

Examples 10A & 10B

Example 10A

Example 10B

The (−)-enantiomer of the title compound of Preparative Example 8, Step B, (3.38 g) is converted to the title compound (Example 10A) via substantially the same procedure as described for Example 10, Steps A–C, to give the title compound Example 10A. m.p.=152° C.; Mass spec.: MH$^+$=637; [α]$_D^{25}$=−62.5° (1,12 mg/2 mL MeOH).

The racemic title compound of Preparative Example 8, Step A, is converted to the title compound (Example 9B) via substantially the same procedure as described for Example 10, Steps A–C to give the title compound Example 10B. m.p.=111.2° C. (dec).

EXAMPLE 11

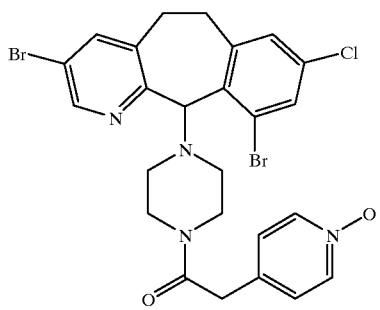

The title compound is prepared using the racemic title compound from Preparative Example 9, Step F, following substantially the same procedure as described for Example 2. $^1$H NMR (CDCl$_3$, 400 MHz): 8.44 (d, 1H); 8.14 (d, 2H): 7.58 (d, 1H); 7.47 (d, 1H); 7.14 (m, 3H); 5.32 (s, 1H); 4.65–4.57 (m, 1H); 3.68 (s, 2H); 3.65–3.39 (m, 4H); 2.91–2.87 (m, 1H); 2.69–2.63 (m, 1H); 2.45–2.33 (m, 4H). MH$^+$=605.

Example 11A & 11B

Example 11A

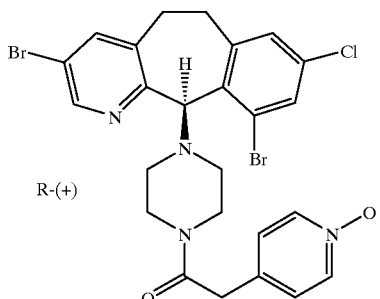

R-(+)

Example 11B

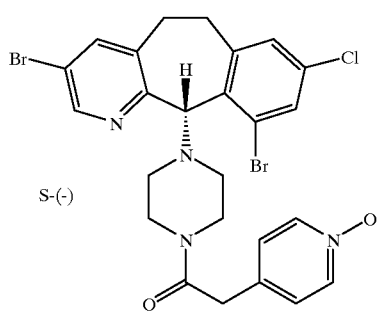

S-(−)

Using the R(+)- or S(−)-enantiomer of the title compound from Preparative Example 9, Step G, the R(+)-enantiomer (Example 11A) or the S-(−)-enantiomer (Example 11B) is prepared using substantially the same procedure as described for Example 2.

Physical chemical data for R-(+)-enantiomer, Example 11A: m.p.=167.0°–167.8° C.; [α]$_D^{25}$=+32.6° (c=1, MeOH); $^1$H NMR (CDCl$_3$, 400 MHz): 8.44 (d, 1H); 8.14 (d, 2H): 7.58 (d, 1H); 7.47 (d, 1H); 7.14 (m, 3H); 5.32 (s, 1H); 4.65–4.57 (m, 1H); 3.68 (s, 2H); 3.65–3.39 (m, 4H); 2.91–2.87 (m, 1H); 2.69–2.63 (m, 1H); 2.45–2.33 (m, 4H). MH$^+$=605.

Physical chemical data for S-(−)-enantiomer, Example 11B: [α]$_D^{25}$=−38.2° (14.67 mg/2 mL, MeOH); $^1$H NMR (CDCl$_3$, 400 MHz): 8.44 (d, 1H); 8.14 (d, 2H): 7.58 (d, 1H); 7.47 (d, 1H); 7.14 (m, 3H); 5.32 (s, 1H); 4.64–4.57 (m, 1H); 3.67 (s, 2H); 3.70–3.34 (m, 4H); 2.95–2.87 (m, 1H); 2.69–2.63 (m, 1H); 2.45–2.31 (m, 4H). MH$^+$=605.

EXAMPLE 12

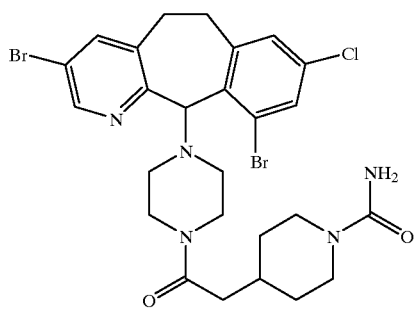

The title compound of this Example is prepared using the racemic title compound from Preparative Example 9, Step F, by following substantially the same procedures as described for Example 8, Steps A–C. This compound is a racemate.

Examples 12A & 12B

Example 12A

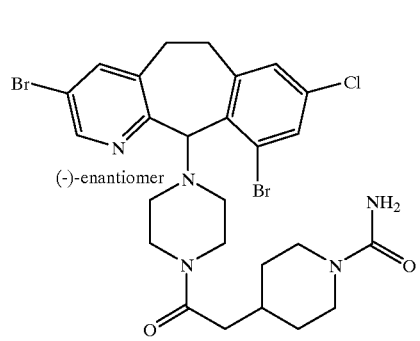

(−)-enantiomer

Example 12B

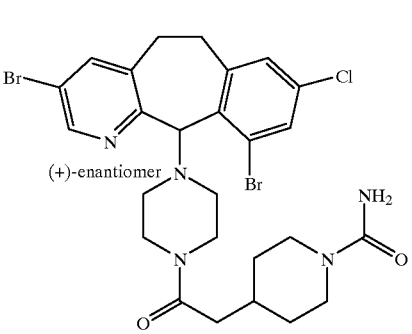

(+)-enantiomer

The title compound of Example 12 is a racemic mixture. Chromatograph 2.45 g of the compound of Example 12, using an Chiralpack AD column and 20% i-PrOH/hexane+ 0.2% diethylamine as the mobile phase, at a flow rate of 100 mL/min., to give 0.970 g of the (+)-enantiomer and 0.982 g of the (−)-enantiomer, Examples 12B and 12A, respectively.

Physical chemical data for (−)-enantiomer, Example 12A: $^1$H NMR (CDCl$_3$, 200 MHz): 8.43 (d, 1H); 7.58 (d, 1H); 7.48 (d, 1H); 7.14 (d, 1H); 5.32 (s, 1H); 4.5–4.75 (m, 1H); 4.4 (s, 2H); 3.9 (d, 2H); 3.2–3.7 (m, 5H); 2.52–3.05 (m, 4H); 1.85–2.5 (m, 6H); 1.5–1.85 (m, 4H); 1.0–1.4 (m, 1H). $[\alpha]_D^{25}$=−31.20 (c=0.453, MeOH).

Physical chemical data for (+)-enantiomer, Example 12B: $^1$H NMR (CDCl$_3$, 200 MHz): 8.43 (d, 1H); 7.58 (d, 1H); 7.48 (d, 1H); 7.14 (d, 1H); 5.32 (s, 1H); 4.5–4.75 (m, 1H); 4.4 (s, 2H); 3.9 (d, 2H); 3.2–3.7 (m, 5H); 2.52–3.05 (m, 4H); 1.85–2.5 (m, 6H); 1.5–1.85 (m, 4H); 1.0–1.4 (m, 1H). $[\alpha]_D^{25}$=+29.8° (c=0.414, MeOH).

EXAMPLE 13

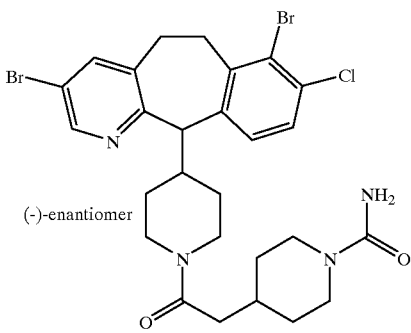

(−)-enantiomer

Step A:

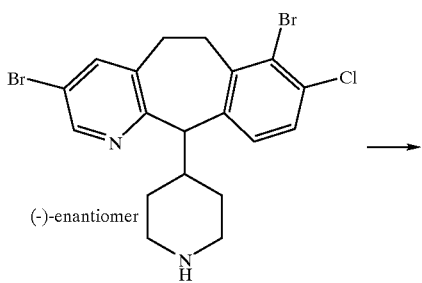

(−)-enantiomer

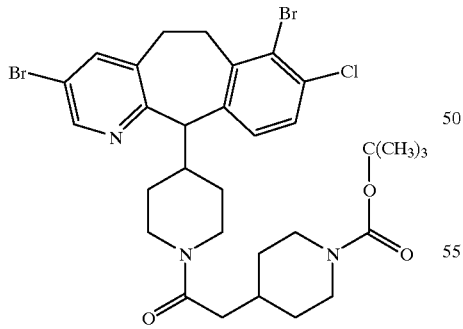

React 1.35 g of the (−)-enantiomer of the title compound of Preparative Example 10, Step B, with 1.4 g of 1-N-t-butoxycarbonylpiperidinyl-4-acetic acid following substantially the same procedures as described for Example 6, Step A, to give 2.0 g of the product. Mass Spec.: MH$^+$=694 (FAB). partial $^1$H NMR (CDCl$_3$, 300 MHz): 8.38 (s, 1H); 7.60 (s, 1H); 7.25 (d, 1H); 7.05 (m, 1H); 1.45 (s, 9H).

Step B:

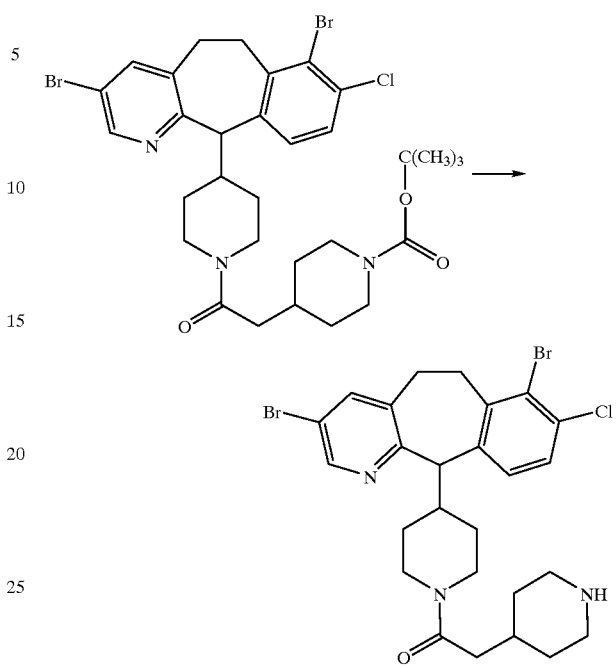

Treat 1.95 g of the product of Step A via substantially the same procedure as described for Example 8, Step B, to give 1.63 g of the product. Mass Spec. MH$^+$=594 (FAB). Partial $^1$H NMR (CDCl$_3$, 300 MHz): 8.38 (s, 1H); 7.60 (s, 1H); 7.25 (d, 1H); 7.03 (m, 1H); 4.64 (d, 1H); 3.90 (m, 2H).

Step C:

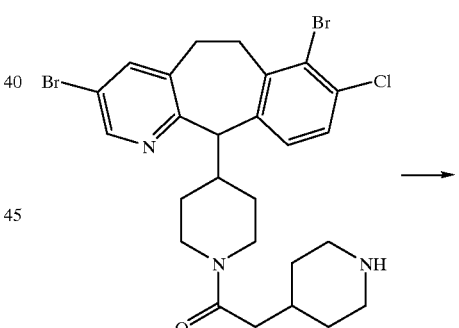

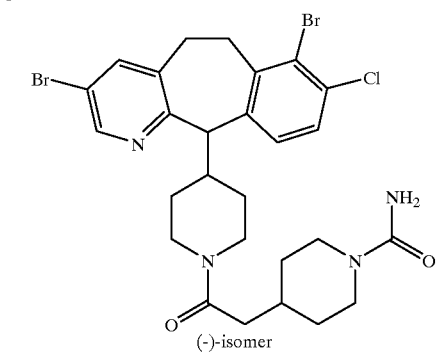

(−)-isomer

Treat 1.6 g of the product of Step B with 1.3 mL of (CH$_3$)$_3$SiNCO using substantially the same procedure as described for Example 6, Step C, to give 1.27 g of the title compound. Mass spec.: MH⁺=637 (FABS); $[\alpha]_D^{25}$=−33.1° (c=0.58, EtOH). partial ¹H NMR (CDCl₃, 400 MHz): 8.38 (s, 1H); 7.59 (s, 1H); 7.25 (d, 1H); 7.04 (m, 1H); 4.60 (d, 1H); 4.41 (s, 2H).

Examples 13A & 13B

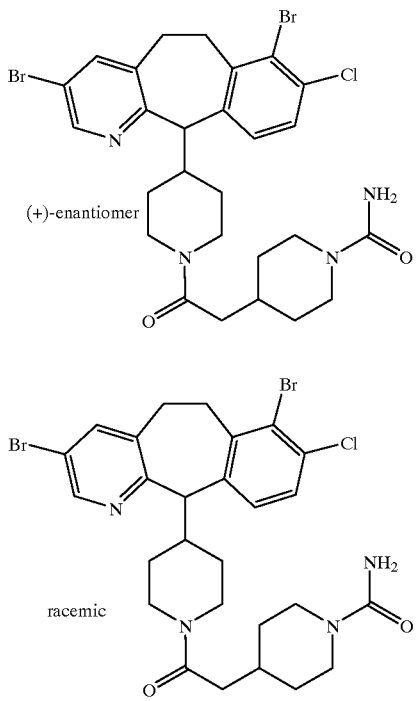

Example 13A
(+)-enantiomer

Example 13B
racemic

The (+)-enantiomer of the title compound from Preparative Example 10, Step B, (2.1 g) is converted to the title compound via substantially the same procedure as described for Example 10, Steps A–C, to give the title compound, Example 13A. Mass spec.: MH⁺=637 (FABS); $[\alpha]_D^{25}$=+32.4° (c=0.57, EtOH). Partial ¹H NMR (CDCl₃, 400 MHz): 8.39 (s, 1H); 7.59 (s, 1H); 7.25 (d, 1H); 7.04 (m, 1H); 4.60 (d, 1H); 4.41 (s, 2H). partial ¹H NMR (DMSO-d₆, 400 MHz): 8.42 (s, 1H); 7.88 (s, 1H); 7.41 (d, 1H); 7.29 (m, 1H); 5.85 (s, 2H); 4.20 (d, 1H).

The racemic title compound from Preparative Example 10, Step A, is converted to the racemic title compound, Example 13B, in an analogous manner. Partial ¹H NMR (CDCl₃, 400 MHz): 8.38 (s, 1H); 7.59 (s, 1H); 7.25 (d, 1H); 7.04 (m, 1H); 4.60 (d, 1H); 4.41 (s, 2H). partial ¹H NMR (DMSO-d₆, 400 MHz): 8.42 (s, 1H); 7.88 (s, 1H); 7.41 (d, 1H); 7.29 (d, 1H); 5.85 (s, 2H); 4.20 (d, 1H).

EXAMPLE 14

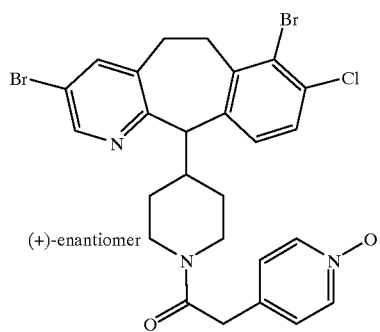

(+)-enantiomer

React 2.6 g of the (+)-enantiomer of the title compound of Preparative Example 10, Step B, and 1.68 g of the title compound of Preparative Example 1 following substantially the same procedure as described for Example 9 to give 2.10 g of the title compound. Mass spec.: MH⁺=604 (FAB); $[\alpha]_D^{25}$=+34.1° (10.98 mg/2 mL, EtOH). partial ¹H NMR (CDCl₃, 400 MHz): 8.38 (s, 1H); 8.15 (d, 2H); 7.58 (s, 1H); 7.26 (d, 1H); 7.15 (d, 2H); 7.03 (d, 1H); 4.57 (d, 1H).

To prepare the HCl salt of the title compound of Example 14 dissolve 700 mg of the title compound in 4 mL of CH₂Cl₂, add 4 mL of Et₂O, cool to 0° C. and slowly add (dropwise) 1 mL of HCl (g) in dioxane. Add 2 mL of Et₂O and stir at 0° C. for 7 min. Dilute with 30 mL of Et₂O, filter to collect the solid product and wash with 30 mL of Et₂O. Dry the solids in vacuo to give 0.836 g of the HCl salt of Example 14. $[\alpha]_D^{25}$=+64.8° (9.94 mg/2 mL, EtOH).

Example 14A & 14B

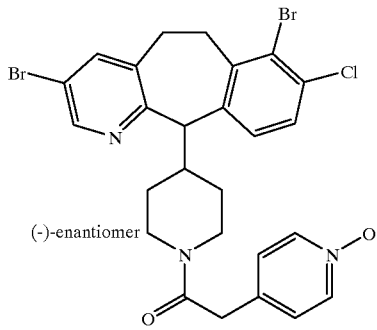

Example 14A
(−)-enantiomer

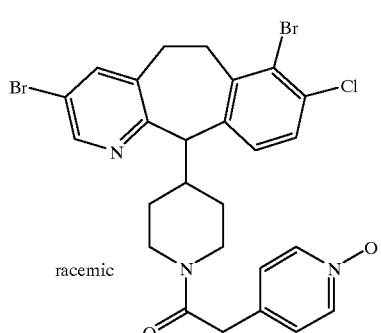

Example 14B
racemic

The (−)-enantiomer of the title compound of Preparative Example 10, Step B, (0.60 g) is reacted with 0.39 g of the title compound of Preparative Example 1, via substantially the same procedure as described for Example 9 to give 0.705 g of the title compound. Mass spec.: MH$^+$=604 (FABS); $[\alpha]_D^{25}$=−41.8° (EtOH). Partial $^1$H NMR (CDCl$_3$, 300 MHz): 8.38 (s, 1H); 8.15 (d, 2H); 7.58 (s, 1H); 7.26 (d, 1H); 7.15 (d, 2H); 7.03 (d, 1H); 4.57 (d, 1H).

The HCl salt of the title compound of Example 14A is prepared via substantially the same procedure as described for Example 14. $[\alpha]_D^{25}$=−63.2° (EtOH).

The racemic title compound of Preparative Example 10, Step A, is converted to the racemic title compound of Example 14B following substantially the same procedure as described for Example 9. Partial $^1$H NMR (CDCl$_3$, 400 MHz): 8.38 (s, 1H); 8.15 (d, 2H); 7.58 (s, 1H); 7.26 (d, 1H); 7.15 (d, 2H); 7.03 (d, 1H); 4.57 (d, 1H). Partial $^1$H NMR (DMSO-d$_6$, 400 MHz): 8.77 (d, 2H); 8.47 (s, 1H); 7.95 (s, 1H); 7.74 (d, 2H); 7.43 (m, 1H); 7.27 (d, 1H); 4.3 5 (d, 1H).

EXAMPLE 15

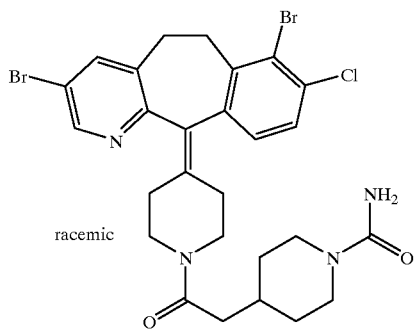

racemic

The title compound of Preparative Example 4 is reacted via substantially the same methods as described for Example 8, Steps A–C, to give the title compound, which is a racemate. Mass Spec.: MH$^+$=635 (FAB). Partial $^1$H NMR (CDCl$_3$): 8.45 (s, 1H); 7.60 (s, 1H); 7.35 (d, 1H); 7.05 (d, 1H); 4.45 (s, 1H).

EXAMPLE 16A & 16B

Example 16A

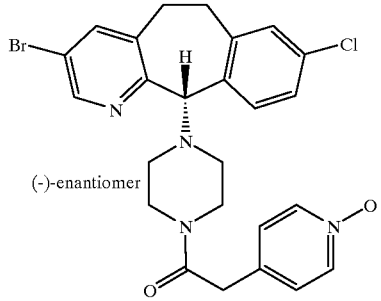

(+)-enantiomer

-continued

Example 16B (−)-enantiomer

The R-(+)-enantiomer or the S-(−) enantiomer of the title compound of Preparative Example 11 is treated via substantially the same procedure as described for Example 2 to give the R-(+)-enantiomer of the title compound or the S-(−)-enantiomer of the title compound, Examples 16A and 16B, respectively.

Physical chemical data for the R-(+)-enantiomer: $^{13}$C NMR (CDCl$_3$): 166.5 (C); 154.8 (C); 146.6 (CH); 140.8 (CH); 140.4 (C); 138.5 (CH); 138.5 (CH); 136.3 (C); 134.6 (C); 133.8 (C); 133.6 (C); 132.0 (CH); 130.0 (CH); 126.3 (CH); 126.3 (CH); 125.8 (CH); 119.6 (C); 78.4 (CH); 51.1 (CH$_2$); 50.6 (CH$_2$); 45.4 (CH$_2$); 41.5 (CH$_2$); 38.0 (CH$_2$); 30.1 (CH$_2$); 30.0 (CH$_2$). $[\alpha]_D^{25}$=+30.7° (10.35 mg/2 mL MeOH).

Physical chemical data for the S-(−)-enantiomer: $^{13}$C NMR (CDCl$_3$): 166.5 (C); 154.8 (C); 146.6 (CH); 140.8 (CH); 140.4 (C); 138.5 (CH); 138.5 (CH); 136.3 (C); 134.6 (C); 133.8 (C); 133.6 (C); 132.0 (CH); 130.0 (CH); 126.3 (CH); 126.3 (CH); 125.8 (CH); 119.6 (C); 78.4 (CH); 51.1 (CH$_2$); 50.6 (CH$_2$); 45.4 (CH$_2$); 41.5 (CH$_2$); 38.0 (CH$_2$); 30.1 (CH$_2$); 29.9 (CH$_2$). $[\alpha]_D^{25}$=−30.9° (9.70 mg/2 mL MeOH).

EXAMPLES 17 & 17A

Example 17

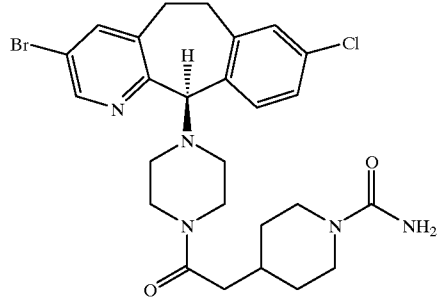

Example 17A

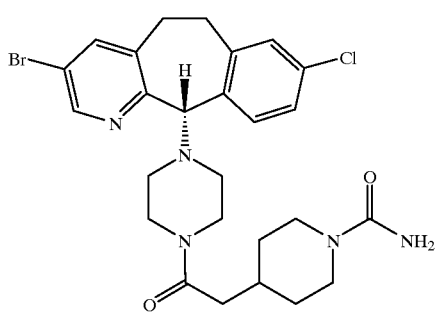

Treat the (+)-enantiomer or the (−)-enantiomer of the title compound of Preparative Example 11 via substantially the same procedure as described for Example 1, Steps A–C, to give the R-(+)-enantiomer of the title compound or the S-(−)-enantiomer of the title compound, Examples 17 and 17A, respectively.

Physical chemical data for the R-(+)-enantiomer: $^{13}$C NMR (CDCl$_3$): 169.3 (C); 157.5 (C); 155.0 (C); 146.6 (CH); 140.8 (CH); 140.4 (C); 136.3 (C); 134.8 (C); 133.7 (C); 132.0 (CH); 130.0 (CH); 125.8 (CH); 119.6 (C); 78.5 (CH); 51.4 (CH$_2$); 50.9 (CH$_2$); 45.2 (CH$_2$); 43.9 (CH$_2$); 43.9 (CH$_2$); 41.1 (CH$_2$); 38.8 (CH$_2$); 32.5 (CH); 31.5 (CH$_2$); 31.5 (CH$_2$); 30.1 (CH$_2$); 30.0 (CH$_2$). $[\alpha]_D^{29.8}$=+28.7° (10.1 mg/2 mL MeOH).

Physical chemical data for the S-(−)-enantiomer: $^{13}$C NMR (CDCl$_3$): 169.3 (C); 157.6 (C); 155.0 (C); 146.6 (CH); 140.8 (CH); 140.4 (C); 136.3 (C); 134.8 (C); 133.7 (C); 132.0 (CH); 130.0 (CH); 125.8 (CH); 119.6 (C); 78.5 (CH); 51.4 (CH$_2$); 50.9 (CH$_2$); 45.2 (CH$_2$); 43.9 (CH$_2$); 43.9 (CH$_2$); 41.1 (CH$_2$); 38.8 (CH$_2$); 32.5 (CH); 31.5 (CH$_2$); 31.5 (CH$_2$); 30.1 (CH$_2$); 30.0 (CH$_2$). $[\alpha]_D^{24.8}$=−28.5° (10.1 mg/2 mL MeOH).

EXAMPLE 18

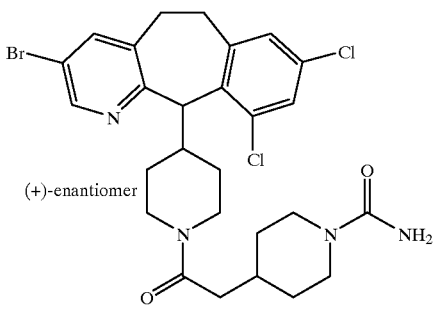
(+)-enantiomer

Step A:

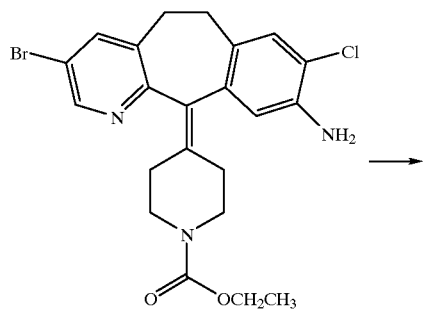

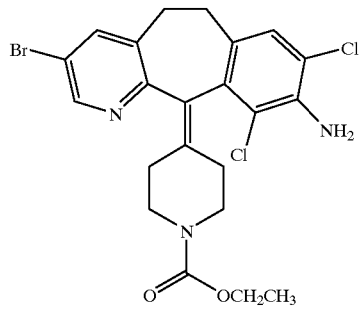

Dissolve 9.90 g (18.9 mmol) of the product of Preparative Example 7, Step B, in 150 mL CH$_2$Cl$_2$ and 200 mL of CH$_3$CN and heat to 60° C. Add 2.77 g (20.8 mmol) N-chlorosuccinimide and heat to reflux for 3 h., monitoring the reaction by TCL (30% EtOAc/H20). Add an additional 2.35 g (10.4 mmol) of N-chlorosuccinimide and reflux an additional 45 min. Cool the reaction mixture to room temperature and extract with 1N NaOH and CH$_2$Cl$_2$. Dry the CH$_2$Cl$_2$ layer over MgSO$_4$, filter and purify by flash chromatography (1200 mL normal phase silica gel, eluting with 30% EtOAc/H$_2$O) to obtain 6.24 g of the desired product. M.p. 193–195.4° C. MH$^+$=510.

Step B:

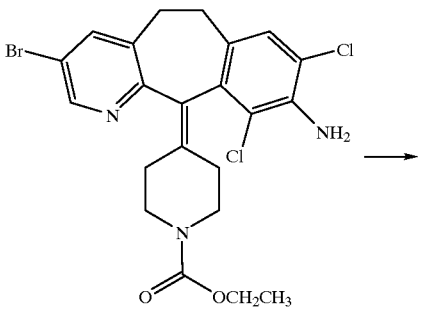

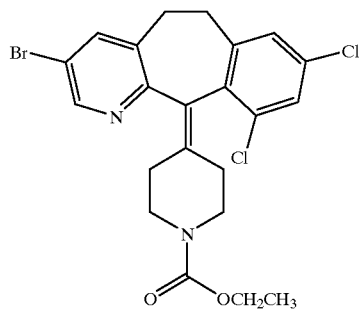

To 160 mL of conc. HCl at −10° C. add 2.07 g (30.1 mmol) NaNO$_2$ and stir for 10 min. Add 5.18 g (10.1 mmol) of the product of Step A and warm the reaction mixture from −10° C. to 0° C. for 2 h. Cool the reaction to −10° C., add 100 mL H$_3$PO$_2$ and let stand overnight. To extract the reaction mixture, pour over crushed ice and basify with 50% NaOH/CH$_2$Cl$_2$. Dry the organic layer over MgSO$_4$, filter and concentrate to dryness. Purify by flash chromatography (600 mL normal phase silica gel, eluting with 20% EtOAc/hexane) to obtain 3.98 g of product. Mass spec.: MH$^+$=495.

Step C:

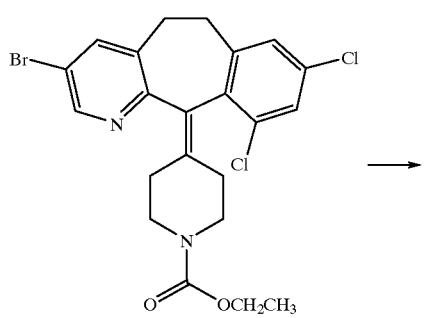

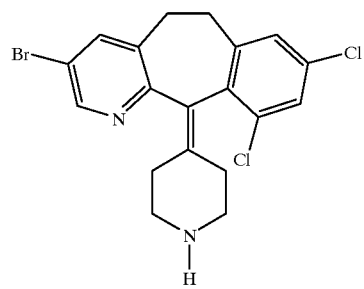

Dissolve 3.9 g of the product of Step B in 100 mL conc. HCl and reflux overnight. Cool the mixture, basify with 50% w/w NaOH and extract the resultant mixture with $CH_2Cl_2$. Dry the $CH_2Cl_2$ layer over $MgSO_4$, evaporate the solvent and dry under vacuum to obtain 3.09 g of the desired product. Mass spec.: $MH^+$=423.

Step D:

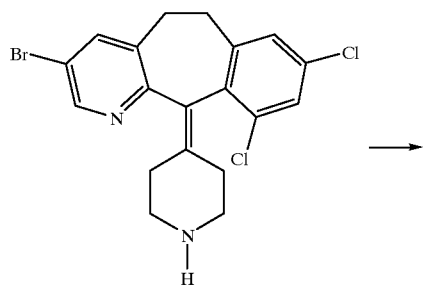

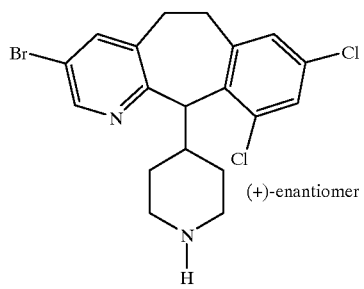

Using a procedure similar to that described in Preparative Example 8, obtain 1.73 g of the desired product, m.p. 169.6–170.1° C.; $[\alpha]_D^{25}$=+48.2° (c=1, MeOH). $MH^+$=425.

Step E:

Use a procedure similar to that of Example 4 with the product of Step D as the starting material to obtain the title compound. M.p. 152.3–153.3° C.; $[\alpha]_D^{25}$=+53.0° (c=1, MeOH). $MH^+$=593.

EXAMPLE 19

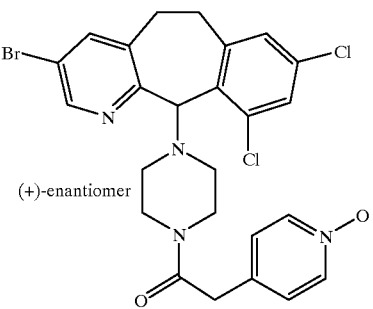

Step A:

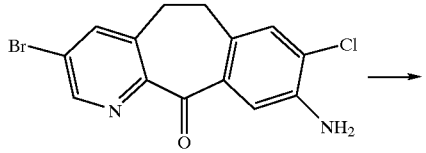

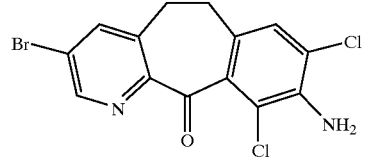

Treat 15.0 g (44.4 mmol) of the product of Preparative Example 9, Step B, with 6.52 g (48.9 mmol) of N-chlorosuccinimide in a manner similar to that described in Example 18, Step A and extract as described to obtain 16.56 g of the desired product, m.p. 234.7–235.0° C. $MH^+$=370.

Step B:

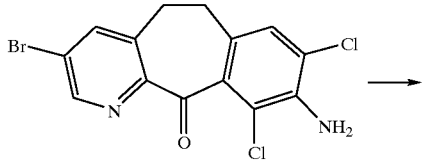

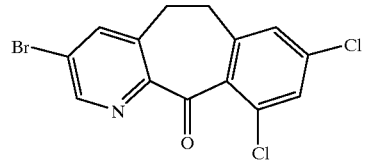

Treat 16.95 g (45.6 mmol) of the product of Step A in the manner described in Example 18, Step B, to obtain 13.07 g of the desired product, m.p. 191.7–192.1° C. $MH^+$=356.

Step C:

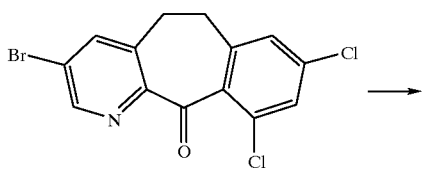

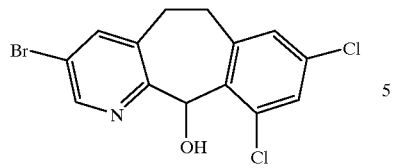

Using the procedure substantially as described in Preparative Example 9, Step E, treat 10.0 g (28.0 mmol) of the product of Step B with NaBH₄ to obtain the desired product, which is used in the next step without further purification.

Step D:

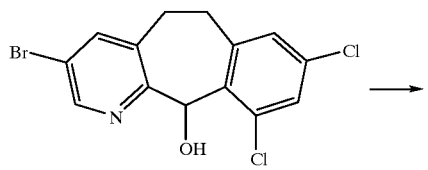

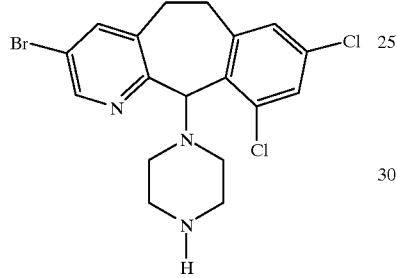

Dissolve 10.0 g (27.9 mmol) of the product of Step C in 200 mL CH₂Cl₂ under N₂ with stirring at room temperature. Cool the reaction mixture to 0° C. and add 2.63 g of triethylamine and 4.80 g (41.9 mmol) of methanesulfonyl chloride. To the resultant solution at 0° C. add a solution of 16.84 g (19.6 mmol) piperazine and 100 mL of THF, immediately followed by 100 mL DMF. Stir overnight at room temperature. Evaporate the solvent and extract the resultant residue with CH₂Cl₂ and sat'd NaHCO₃. Dry the CH₂Cl₂ layer over MgSO₄, filter and concentrate to obtain the crude product. Chromatograph the crude product on 1200 mL silica gel, eluting with 5% CH₃OH(sat'd with NH₃) in CH₂Cl₂ to obtain a racemic mixture. Separate the racemic compound by chiral chromatography using a Chiralpack AD column (5 cm×50 cm), eluting with 30% iPrOH/hexane with 0.2% diethylamine. Mass spec.: MH⁺= 426. The desired isomer is the (+)-enantiomer.

Step E:

Stir 2.0 g (4.7 mmol) of the product of Step D in 40 mL DMF under N₂, cool the mixture to 0° and add 0.615 g (6.1 mmol) N-methylmorpholine, 1.1668 g (6.1 mmol) DEC, 0.8225 g (6.1 mmol) HOBT and 1.6042 g (6.1 mmol) of the product of Preparative Example 1. Stir overnight at room temperature. Evaporate the solvent and extract the resultant residue with CH₂Cl₂/water, sat'd NaHCO₃, 10% NaH₂PO₄ and brine. Separate the CH₂Cl₂ layer, dry over MgSO₄, filter and concentrate to dryness. Purify the resultant residue by flash chromatography on 400 mL of normal phase silica gel, eluting with 5% CH₃OH/NH₃—CH₂Cl₂ to obtain 2.43 g of the title compound, m.p. 145.3–146.1° C.; $[\alpha]_D^{25}$=+33.6° (c=1, MeOH). MH⁺=561.

EXAMPLE 20

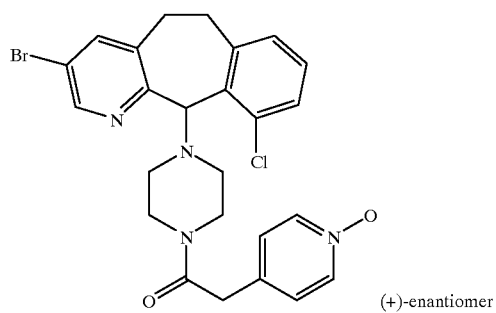

Step A:

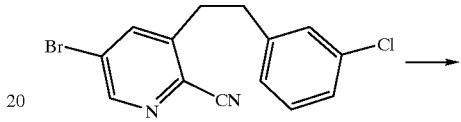

Heat 200 mg of the cyano starting material in 17 g polyphosphoric acid at 190–200° C. for 45 min. Pour the resultant mixture into ice, add 30% HCl and stir for 30 min. Extract with CH₂Cl₂, wash with brine, dry over Na₂SO₄, filter and concentrate. Purify by preparative TLC, eluting with EtOAc/hexane to obtain 21 mg of the desired product (also obtained 59 mg of the 10-chloro product).

Step B:

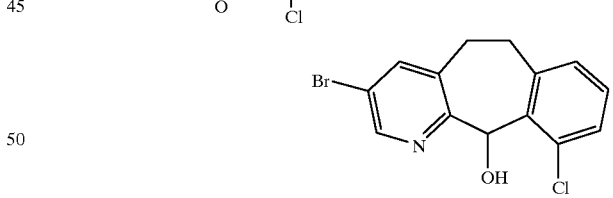

Using the procedure substantially as described in Preparative Example 9, Step E, treat 1.75 g (5.425 mmol) of the product of Step A with NaBH₄ to obtain the desired product.

Step C:

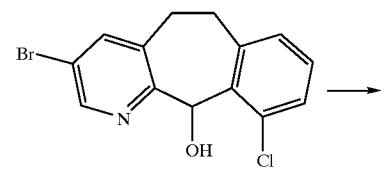

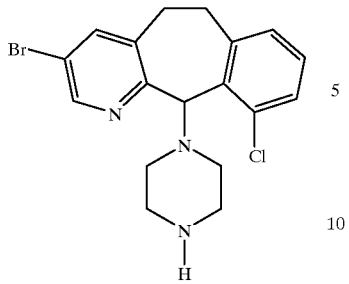

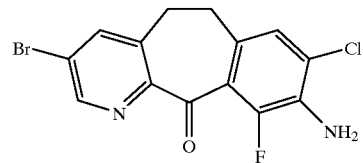

Dissolve the residue obtained in Step B in 50 mL CH$_2$Cl$_2$ at room temperature, add 3.95 mL (5.425 mmol) of SOCl$_2$ and stir at room temperature overnight. Remove excess SOCl$_2$ and solvent under vacuum. Dissolve the residue in CH$_2$Cl$_2$, wash with sat'd NaHCO$_3$ and brine, dry over Na$_2$SO$_4$, filter and concentrate. Add 25 mL THF to the resultant residue, add 2.33 g (27.125 mmol) piperazine and stir at room temperature overnight. Evaporate the solvent, add CH$_2$Cl$_2$ wash with sat'd NaHCO$_3$ and brine, dry over Na$_2$SO$_4$, filter and concentrate. Purify the resultant residue by chiral chromatography using a Chiralpack AD column and eluting with 20% iPrOH/hexane with 0.2% diethylamine. Mass spec.: MH$^+$=392. The desired isomer is the (+)-enantiomer.

Step D:

Combine 770 mg (1.960 mmol) of the product of Step C, 323 μl (2.548 mmol) N-methylmorpholine, 344 mg (2.548 mmol) HOBT, 487 mg (2.548 mmol) DEC and 390 mg (2.548 mmol) of the compound of Preparative Example 1 in 8 ml DMF and stir at room temperature overnight. Evaporate the solvent, add EtOAc and wash with sat'd NaHCO$_3$, water and brine, and dry over Na$_2$SO$_4$. Purify by flash chromatography on silica gel, eluting with EtOAc to 10, 12% (10%NH$_4$OH/CH$_3$OH)/EtOAc gradient. Further purify by preparative TLC (1000μ silica gel) to obtain 750 mg of the title compound, [α]$_D^{25}$=+23.3° (c=0.322, MeOH).

EXAMPLE 21

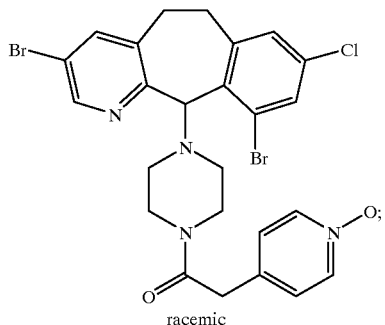
racemic

Step A:

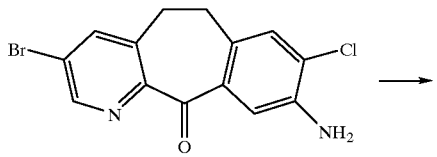

Dissolve 10.0 g (29.6 mmol) of the product of Preparative Example 9, Step B, in 150 mL CH$_2$Cl$_2$ and 200 mL CH$_3$CN at room temperature. Heat the mixture to 60° C., add 10.45 g (32.6 mmol) of 1-fluoro-4-hydroxy-1,4-diazoniabicyclo[2,2,2]octane bis-(tetrafluoroborate) and heat to reflux for 4 h. Cool the mixture to room temperature, extract with CH$_2$Cl$_2$ and 1 N NaOH. Dry the CH$_2$Cl$_2$ layer over MgSO$_4$, filter and concentrate to dryness. Purify the resultant residue by flash chromatography using 1400 mL normal phase silica gel eluted with 10% EtOAc-CH$_2$Cl$_2$+2 drops NH$_4$OH to obtain 2.00 g of product, m.p. 103.2–103.5° C. MH$^+$=355.

Step B:

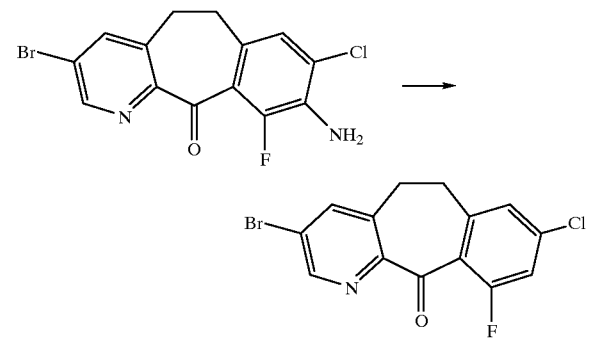

Using a procedure substantially as described in Preparative Example 9, Step D, treat 1.80 g (5.1 mmol) of the product of Step A. Purify the crude product by flash chromatography using 200 mL normal phase silica gel eluted with 20% EtOAc/hexane. Mass spec.: MH$^+$=339.

Step C:

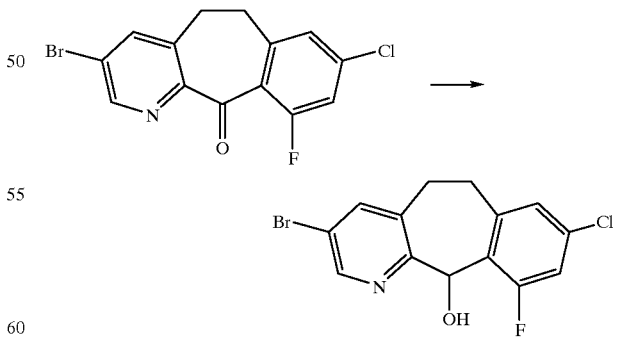

Using the procedure substantially as described in Preparative Example 9, Step E, treat 0.47 g (1.4 mmol) of the product of Step B with NaBH$_4$ to obtain the desired product. Mass spec.: MH$^+$=342.

Step D:

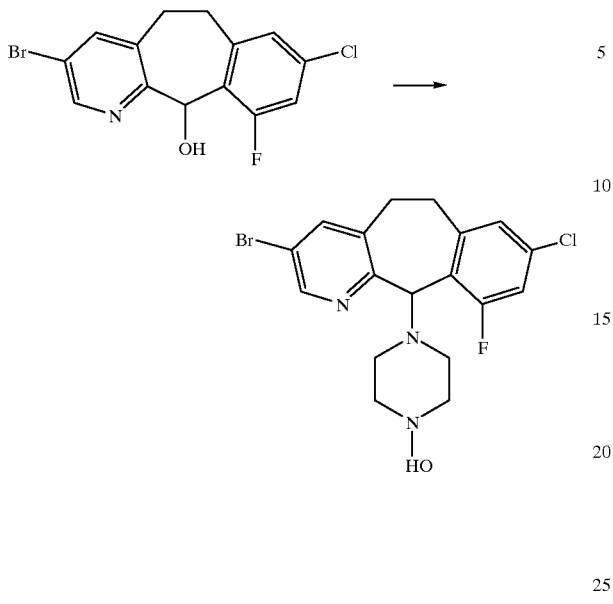

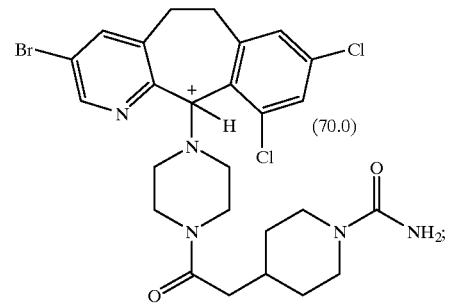
(70.0)

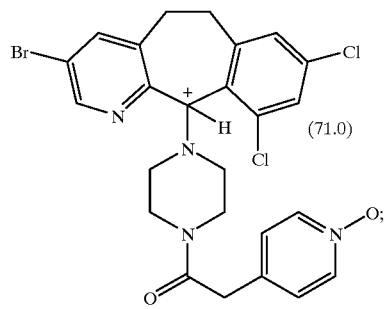
(71.0)

Dissolve 0.37 g (1.1 mmol) of the product of Step C in 20 mL toluene under $N_2$ and cool from room temperature to 0° C. Add 0.3855 g (3.2 mmol) of $SOCl_2$ and stir at room temperature, then add 10 mL $CHCl_3$ and stir for 3 h. Evaporate the solvent, extract the resultant residue with 1 N NaOH—$CH_2Cl_2$, dry the $CH_2Cl_2$ layer over $MgSO_4$, filter and concentrate to dryness. Dissolve the residue in 10 mL THF under $N_2$, add 0.465 g (5.4 mmol) of piperazine, 10 mL THF and stir overnight at room temperature. Repeat the extraction procedure to obtain the desired product. Mass spec.: $MH^+$=410.

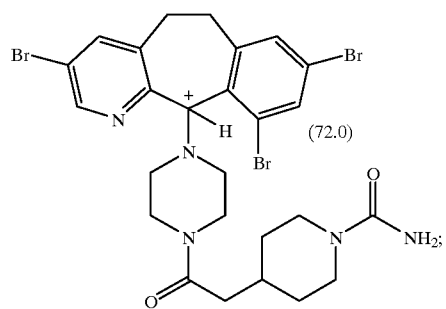
(72.0)

Step E:

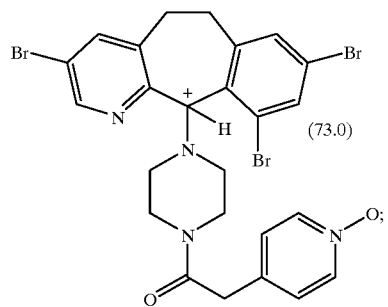
(73.0)

Treat 0.44 g (1.1 mmol) of the product of Step D with N-methylmorpholine, 4-pyridylacetic acid N-oxide, DEC and HOBT in DMF as described in Example 5. Evaporate the solvent and extract the resultant residue with $CH_2Cl_2$—$H_2O$, sat'd $NaHCO_3$, 10% $NaH_2PO_4$ and brine. Dry the $CH_2Cl_2$ layer over $MgSO_4$, filter and concentrate to dryness. Purify the resultant residue by flash chromatography on 150 mL normal phase silica gel, eluting with 5% $CH_3OH/NH_3$—$CH_2Cl_2$ to obtain 0.41 g of the title compound, m.p. 155.0–155.6° C.; Mass spec.: $MH^+$=545.

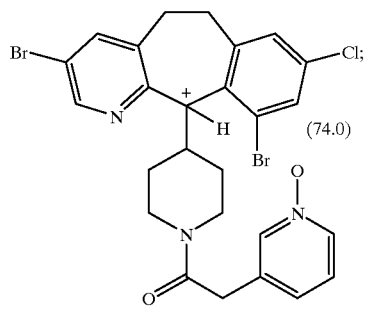
(74.0)

Using appropriate starting materials and procedures as described above, the following compounds could be made:

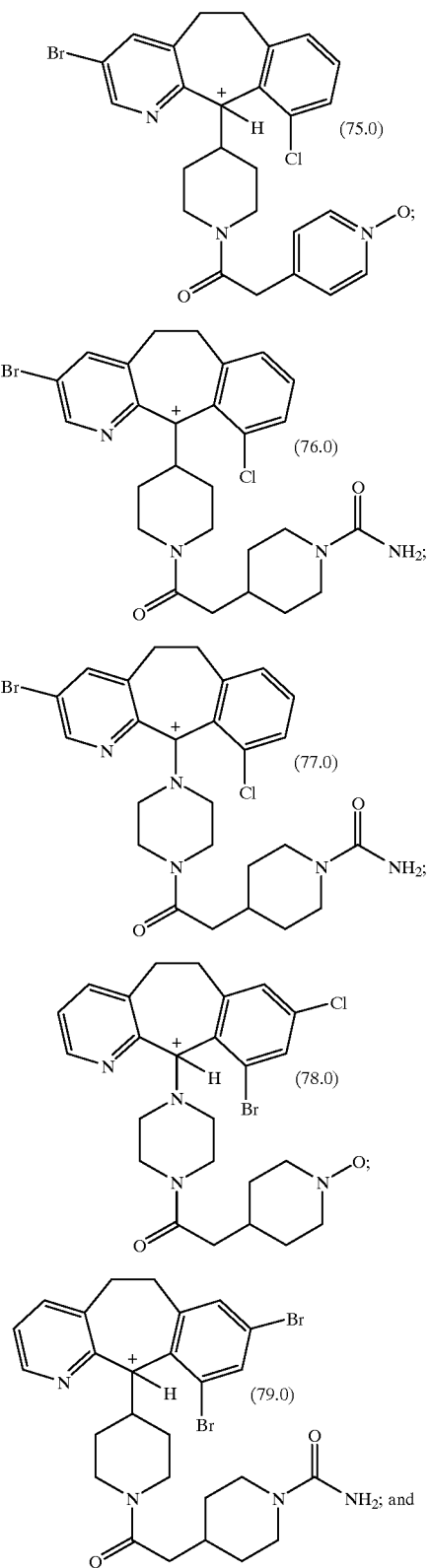

Assays

1. In vitro Enzyme assays: Inhibition of Farnesyl Protein Transferase and Geranylgeranyl Protein Transferase Both farnesyl protein transferase (FPT) and geranylgeranyl protein transferase (GGPT) I were partially purified from rat brain by ammonium sulfate fractionation followed by Q-Sepharose (Pharmacia, Inc.) anion exchange chromatography essentially as described by Yokoyama et al (Yokoyama, K., et al., (1991), A protein geranylgeranyltransferase from bovine brain: Implications for protein prenylation specificity, *Proc. Natl. Acad. Sci USA* 88: 5302–5306, the disclosure of which is incorporated herein by reference thereto). Human farnesyl protein transferase was also expressed in *E. coli*, using cDNA clones encoding both the a and b subunits. The methods used were similar to those published (Omer, C. et al., (1993), Characterization of recombinant human farnesyl protein transferase: Cloning, expression, farnesyl diphosphate binding, and functional homology with yeast prenyl-protein transferases, Biochemistry 32:5167–5176). Human farnesyl protein transferase was partially-purified from the soluble protein fraction of *E. coli* as described above. The tricyclic farnesyl protein transferase inhibitors disclosed herein inhibited both human and rat enzyme with similar potencies. Two forms of val$^{12}$-Ha-Ras protein were prepared as substrates for these enzymes, differing in their carboxy terminal sequence. One form terminated in cysteine-valine-leucine-serine (Ras-CVLS) the other in cystein-valine-leucine-leucine (Ras-CVLL). Ras-CVLS is a substrate for the farnesyl protein transferase while Ras-CVLL is a substrate for geranylgeranyl protein transferase I. The cDNAs encoding these proteins were constructed so that the proteins contain an amino-terminal extension of 6 histidine residues. Both proteins were expressed in *Escherichia coli* and purified using metal chelate affinity chromatography. The radiolabelled isoprenyl pyrophosphate substrates, [$^3$H]farnesyl pyrophosphate and [$^3$H]geranylgeranyl pyrophosphate, were purchased from DuPont/New England Nuclear.

Several methods for measuring farnesyl protein transferase activity have been described (Reiss et al 1990, *Cell* 62: 81; Schaber et al 1990, *J. Biol. Chem.* 265: 14701; Manne et al 1990, *PNAS* 87: 7541; and Barbacid & Manne 1993, U.S. Pat. No. 5,185,248). The activity was assayed by measuring the transfer of [$^3$H]farnesyl from [$^3$H]farnesyl pyrophosphate to Ras-CVLS using conditions similar to those described by Reiss et al. 1990 (*Cell* 62: 81) The reaction mixture contained 40 mM Hepes, pH 7.5; 20 mM magnesium chloride; 5 mM dithiothreitol; 0.25 μM [$^3$H] farnesyl pyrophosphate; 10 ml Q-Sepharose-purified farnesyl protein transferase; the indicated concentration of tricyclic compound or dimethylsulfoxide (DMSO) vehicle control (5% DMSO final); and 5 mM Ras-CVLS in a total volume of 100 ml. The reaction was allowed to proceed for 30 minutes at room temperature and then stopped with 0.5 ml of 4% sodium dodecyl sulfate (SDS) followed by 0.5 ml of cold 30% TCA. Samples were allowed to sit on ice for 45 minutes and precipitated Ras protein was then collected on GF/C filter paper mats using a Brandel cell harvester. Filter mats were washed once with 6% TCA, 2% SDS and radioactivity was measured in a Wallac 1204 Betaplate BS liquid scintillation counter. Percent inhibition was calculated relative to the DMSO vehicle control.

The geranylgeranyl protein transferase I assay was essentially identical to the farnesyl protein transferase assay described above, with two exceptions: [3H] geranylgeranylpyrophosphate replaced farnesyl pyrophosphate as the isoprenoid donor and Ras-CVLL was the protein acceptor. This is similar to the assay reported by Casey et al (Casey, P. J., et al., (1991), Enzymatic modification of proteins with a geranylgeranyl isoprenoid, *Proc. Natl. Acad. Sci, USA* 88: 8631–8635, the disclosure of which is incorporated herein by reference thereto).

2. Cell-Based Assay: Transient Expression of val$^{12}$-Ha-Ras-CVLS and val$^{12}$-Ha-Ras-CVLL in COS Monkey Kidney Cells: Effect of Farnesyl Protein Transferase Inhibitors on Ras Processing and on Disordered Cell Growth Induced By Transforming Ras COS monkey kidney cells were transfected by electroporation with the plasmid pSV-SPORT (Gibco/BRL) containing a cDNA insert encoding either Ras-CVLS or Ras-CVLL, leading to transient overexpression of a Ras substrate for either farnesyl protein transferase or geranylgeranyl protein transferase I, respectively (see above).

Following electroporation, cells were plated into 6-well tissue culture dishes containing 1.5 ml of Dulbecco's-modified Eagle's media (GIBCO, Inc.) supplemented with 10% fetal calf serum and the appropriate farnesyl protein transferase inhibitors. After 24 hours, media was removed and fresh media containing the appropriate drugs was re-added.

48 hours after electroporation cells were examined under the microscope to monitor disordered cell growth induced by transforming Ras. Cells expressing transforming Ras become more rounded and refractile and overgrow the monolayer, reminiscent of the transformed phenotype. Cells were then photographed, washed twice with 1 ml of cold phosphate-buffered saline (PBS) and removed from the dish by scraping with a rubber policeman into 1 ml of a buffer containing 25 mM Tris, pH 8.0; 1 mM ethylenediamine tetraacetic acid; 1 mM phenylmethylsulfonyl fluoride; 50 mM leupeptin; and 0.1 mM pepstatin. Cells were lysed by homogenization and cell debris was removed by centrifugation at 2000×g for 10 min.

Cellular protein was precipitated by addition of ice-cold trichloroacetic acid and redissolved in 100 ml of SDS-electrophoresis sample buffer. Samples (5–10 ml) were loaded onto 14% polyacrylamide minigels (Novex, Inc.) and electrophoresed until the tracking dye neared the bottom of the gel. Proteins resolved on the gels were electroblotted onto nitrocellulose membranes for immunodetection.

Membranes were blocked by incubation overnight at 4° C. in PBS containing 2.5% dried milk and 0.5% Tween-20 and then incubated with a Ras-specific monoclonal antibody, Y13-259 (Furth, M. E., et al., (1982), Monoclonal antibodies to the p21 products of the transforming gene of Harvey murine sarcoma virus and of the cellular ras gene family, *J. Virol.* 43: 294–304), in PBS containing 1% fetal calf serum for one hour at room temperature. After washing, membranes were incubated for one hour at room temperature with a 1:5000 dilution of secondary antibody, rabbit anti-rat lgG conjugated to horseradish peroxidase, in PBS containing 1% fetal calf serum. The presence of processed and unprocessed Ras-CVLS or Ras-CVLL was detected using a colorimetric peroxidase reagent (4-chloro-1-naphthol) as described by the manufacturer (Bio-Rad).

3. Cell Mat Assay

Normal human HEPM fibroblasts were planted in 3.5 cm dishes at a density of 5×10$^4$ cells/dish in 2 ml growth medium, and incubated for 3–5 d to achieve confluence. Medium was aspirated from each dish and the indicator tumor cells, T24-BAG4 human bladder carcinoma cells expressing an activated H-ras gene, were planted on top of the fibroblast monolayer at a density of 2×10$^3$ cells/dish in 2 ml growth medium, and allowed to attach overnight. Compound-induced colony inhibition was assayed by addition of serial dilutions of compound directly to the growth medium 24 h after tumor cell planting, and incubating cells for an additional 14 d to allow colony formation. Assays were terminated by rinsing monolayers twice with phosphate-buffered saline (PBS), fixing the monolayers with a 1% glutaraldehyde solution in PBS, then visualizing tumor cells by staining with X-Gal (Price, J., et al., Lineage analysis in the vertebrate nervous system by retrovirus-mediated gene transfer, Proc. Natl. Acad. Sci.84, 156–160 (1987)). In the colony inhibition assay, compounds were evaluated on the basis of two IC$_{50}$ values: the concentration of drug required to prevent the increase in tumor cell number by 50% (tIC$_{50}$) and the concentration of drug required to reduce the density of cells comprising the cell mat by 50% (mIC$_{50}$). Both IC$_{50}$ values were obtained by determining the density of tumor cells and mat cells by visual inspection and enumeration of cells per colony and the number of colonies under the microscope. The therapeutic index of the compound was quantitatively expressed as the ratio of mIC$_{50}$/tIC$_{50}$, with values greater than one indicative of tumor target specificity.

Additional assays were carried out by following essentially the same procedure as described above, but with substitution of alternative indicator tumor cell lines in place of the T24-BAG cells. The assays were conducted using either DLD-1-BAG human colon carcinoma cells expressing as activated K-ras gene or SW620-BAG human colon carcinoma cells expressing an activated K-ras gene. Using other tumor cell lines known in the art, the activity of the compounds of this invention against other types of cancer cells (such as those listed herein on pages 15 and 16) can be demonstrated.

4. Soft Agar Assay

Anchorage-independent growth is a characteristic of tumorigenic cell lines. Human tumor cells are suspended in growth medium containing 0.3% agarose and an indicated concentration of a farnesyl transferase inhibitor. The solution is overlayed onto growth medium solidified with 0.6% agarose containing the same concentration of farnesyl transferase inhibitor as the top layer. After the top layer is solidified, plates are incubated for 10–16 days at 37° C. under 5% CO$_2$ to allow colony outgrowth. After incubation, the colonies are stained by overlaying the agar with a solution of MTT (3-[4,5-dimethylthiazol-2-yl]-2,5-diphenyltetrazolium bromide, Thiazolyl blue) (1 mg/mL in PBS). Colonies are counted and the IC50's determined.

TABLE 1

FPT INHIBITION

| EXAMPLE | FPT IC$_{50}$ ($\mu$M) | EXAMPLE | FPT IC$_{50}$ ($\mu$M) |
|---|---|---|---|
| 1 | <0.034 | 2 | 0.010 |
|   |        |   | 0.016 |
| 4 | 0.046 | 16A | 0.032 |
|   |       |     | 0.026 |
| 16B | 0.038 | 11B | >0.095 |
|     | 0.023 |     |        |
| 15 | 0.022 | 7 | 0.012 |
| 8 | 0.021 | 11A | 0.0018 |
|   |       |     | 0.0021 |
| 5 | 0.0023 | 12B | 0.0025 |
| 9 | 0.0013 | 10 | 0.0019 |
| 7B | <0.003 | 8B | 0.013 |
| 14A | 0.0026 | 14 | 0.062 |
| 13A | 0.078 | 13 | 0.005 |
| 5A | >0.099 | 7A | >0.1 |
| 8A | >0.094 | 10A | >0.094 |
| 9A | >0.088 | 6 | 0.0031 |
| 11 | 0.002 | 5B | ~0.003 |
| 12A | >0.094 | 13B | 0.005 |
| 14B | 0.005 | 5 · HCl salt | 0.0038 |
| 14A · HCl salt | <0.0031 | 9B | 0.003 |
| 10B | 0.003 | 17 | 0.043 |
| 17A | 0.048 | 18 | 0.0031 |
| 19 | <0.0038 | 20 | 0.0062 |
| 21 | 0.0084 |   |   |

TABLE 2

COMPARISON OF FPT INHIBITION AND GGPT INHIBITION

| EXAMPLE | ENZYME INHIBITION FPT IC$_{50}$ $\mu$M | ENZYME INHIBITION GGPT IC$_{50}$ $\mu$M |
|---|---|---|
| 2 | 0.010 | >300 |
|   | 0.016 |      |
| 4 | 0.046 | >35.7 |
| 5B | ~0.003 | >300 |
| 16A | 0.032 | >38 |
|     | 0.026 |     |
| 16B | 0.038 | >76 |
|     | 0.023 |     |
| 7 | 0.012 | >300 |
| 11A | 0.0018 | >66 |
|     | 0.0021 |     |
| 9 | 0.0013 | >59 |
| 5 | 0.0023 | >66 |
| 14A | 0.0026 | >62 |
| 13 | 0.005 | >63 |
| 7B | <0.003 | >66 |
| 8B | 0.013 | >60 |
| 18 | 0.0031 | >50 |
| 20 | 0.0062 | >38 |

TABLE 3

ACTIVITY IN COS CELLS

| Example | Inhibition of Ras Processing IC$_{50}$ ($\mu$M) | Example | Inhibition of Ras Processing IC$_{50}$ ($\mu$M) |
|---|---|---|---|
| 8 | <0.25 | 2 | 0.25 |
| 15 | 0.60 | 16A | 0.5 |
| 16B | 0.125 | 11 | <0.25 |
| 7 | <0.25 | 5B | 0.05 |
| 10 | <0.025 | 10A | 2.0 |
| 12B | <0.025 | 12A | 0.95 |
| 11A | <0.025 | 11B | 2.25 |
| 5 | 0.098 | 14A · HCl salt | 0.015 |
| 13 | 0.420 | 9 | 0.010 |
| 7B | 0.025 | 8B | 0.280 |
| 9A | 0.85 | 5 · HCl salt | 0.010 |
| 5A | 5.0 | 14A | 0.480 |
|    | 1.0 |     |        |
| 14 | >1.0 | 13A | >1.0 |
| 7A | >1.0 | 8A | >1.0 |
| 17 | 0.350 | 17A | 0.500 |
| 14B | 0.045 | 6 | 0.040 |
| 18 | 0.025 | 19 | 0.045 |
| 20 | ~0.030 | 21 | 0.42 |

TABLE 4

INHIBITION OF TUMOR CELL GROWTH - MAT ASSAY

| Example | Tumor (T-24) IC$_{50}$ ($\mu$M) | Tumor (DLD-1) IC$_{50}$ ($\mu$M) | Tumor (SW620) IC$_{50}$ ($\mu$M) | Normal IC$_{50}$ ($\mu$M) |
|---|---|---|---|---|
| 1 | <1.6 | — | — | >25 |
| 4 | 3.1 | — | — | >25 |
| 7 | <1.6 | <1.6 | 6.25 | >25 |
| 5B | <1.6 | 3.1 | 10 | >25 |
| 13B | <1.6 | 3.1 | >3.1 | 25 |
| 11B | <1.6 | 8 | 18 | >25 |
| 9A | <1.6 | 12.5 | 12.5 | 18 |
| 10A | <1.6 | 2.0 | 1.6 | 8 |
| 5 | <1.6 | 3.1 | 6.25 | >25 |
| 14A | <1.6 | 6.25 | 12.5 | >25 |
| 13A | 3.1 | 6.25 | 6.25 | >25 |
| 7B | <1.6 | 1.6 | 3.1 | >25 |
| 8A | <1.6 | <1.6 | 3.1 | >25 |
| 2 | <1.6 | 6.25 | 6.25 | >25 |
| 16B | <1.6 | 6.25 | 25 | >25 |
| 8 | <1.6 | 3.1 | 3.1 | >25 |
| 15 | 3.1 | 6.25 | >6.25 | >25 |
| 11A | <1.6 | <1.6 | >6.25 | >25 |
| 9 | <1.6 | <1.6 | 6.25 | >25 |
| 10 | <1.6 | <1.6 | 3.1 | >25 |
| 12A | <1.6 | 2.0 | 4 | >25 |
| 5A | 12.5 | 12.5 | >25 | >25 |
| 14 | <1.6 | 6.25 | >12.5 | >25 |
| 13 | <1.6 | 3.1 | >1.6 | >25 |
| 8B | <1.6 | <1.6 | 3.1 | >25 |
| 17 | 1.6 | 6.25 | 25 | >25 |
| 17A | 3.1 | 4 | 18 | >25 |
| 10B | <1.6 | 1.6 | 1.6 | >25 |
| 12B | <1.6 | 3.1 | 6.25 | >25 |
| 7A | <1.6 | 1.6 | 3.1 | >25 |
| 6 | <1.6 | 4.0 | 6.24 | — |
| 19 | <1.6 | <1.6 | 6.25 | >25 |

TABLE 5

INHIBITION OF HUMAN TUMOR CELL GROWTH - SOFT AGAR ASSAY

| | IC$_{50}$ ($\mu$M) | |
|---|---|---|
| Tumor Cell Line | Example 10 | Example 18 |
|---|---|---|
| K ras NIH 3T3 | 0.40 | 0.8 |
| H ras NIH 3T3 | 0.075 | 0.175 |
| HTB 177 | 0.04 | 0.2 |

TABLE 5-continued

INHIBITION OF HUMAN TUMOR CELL GROWTH - SOFT AGAR ASSAY

| | $IC_{50}$ ($\mu$M) | |
|---|---|---|
| Tumor Cell Line | Example 10 | Example 18 |
| (NSCLC) K ras mutation | | |
| HTB 173 (NCI H146) | 0.05 | — |
| (SCLC) ras mut. not detected | | |
| A549 | 0.150 | 0.3 |
| (lung) K ras mutation | | |
| HTB 175 | 0.250 | 0.6 |
| (SCLC) ras mut. not detected | | |
| HTB 119 (NCI H69) | 0.3 | — |
| (SCLC) | | |
| HTB 183 (NCI H661) | 0.5 | — |
| (NSCLC) ras mut. not detected | | |
| HPAF II | <0.5 | — |
| (pancreatic) K ras mutation | | |
| MCF-7 | <0.6 | — |
| (breast) ras mut. not detected | | |
| HBL100 | <0.6 | — |
| (breast) ras mut. not detected | | |
| Du4475 | 0.6 | — |
| (breast) ras mut. not detected | | |
| MDA MB 468 | 0.6 | — |
| (breast) ras mut. not detected | | |
| DU 145 | 0.6 | — |
| (prostate) ras mut. not detected | | |
| MDA MB453 (breast) | 0.6 | — |
| BT474 (breast) | 1.0 | — |
| PC3 (prostate) | 1.25 | — |
| DLD 1 | 2.5 | — |
| (colon) K ras mutation | | |
| AsPc-1 | 3.0 | — |
| (pancreatic) K ras mutation | | |

Determined ras mutation status by ELISA (Oncogene Science)

Results

1. Enzymology

The data demonstrate that the compounds of the invention are inhibitors of Ras-CVLS farnesylation by partially purified rat brain farnesyl protein transferase (FPT). The data also show that there are compounds of the invention which can be considered as very potent ($IC_{50}$ <<0.1 $\mu$M) inhibitors of Ras-CVLS farnesylation by partially purified rat brain FPT.

The data also demonstrate that compounds of the invention are poorer inhibitors of geranylgeranyl protein transferase (GGPT) assayed using Ras-CVLL as isoprenoid acceptor. This selectivity is important for the therapeutic potential of the compounds used in the methods of this invention, and increases the potential that the compounds will have selective growth inhibitory properties against Ras-transformed cells.

2. Cell-Based: COS Cell Assay

Western blot analysis of the Ras protein expressed in Ras-transfected COS cells following treatment with the tricyclic farnesyl protein transferase inhibitors of this invention indicated that they inhibit Ras-CVLS processing, causing accumulation of unprocessed Ras (see Table 3). The compound of Example 2, for example, inhibited Ras-CVLS processing with an $IC_{50}$ value of 0.025 $\mu$M, but did not block the geranylgeranylation of Ras-CVLL at concentrations up to 33 $\mu$M.

These results provide evidence for specific inhibition of farnesyl protein transferase, but not geranylgeranyl transferase I, by compounds of this invention in intact cells and indicate their potential to block cellular transformation by activated Ras oncogenes.

3. Cell-Based: Cell Mat Assay

Tricyclic farnesyl protein transferase inhibitors of this invention also inhibited the growth of Ras-transformed tumor cells in the Mat assay without displaying cytotoxic activity against the normal monolayer.

In Vivo Anti-Tumor Studies

Tumor cells ($5\times10^5$ to $8\times10^6$) of DLD-1 (human colon carcinoma cells, ATCC # 221) are innolculated subcutaneously into the flank of 5–6 week old athymic nu/nu female mice. Tumor bearing animals are selected and randomized when the tumors are established. Animals are treated with vehicle ($\beta$-cyclodextrin for i.p. or corn oil for p.o.) only or with a compound of the present invention in vehicle four times a day (QID) for 7 days per week for 4 weeks. The percent inhibition of tumor growth relative to vehicle controls is determined by tumor measurements. The results are reported in Table 6.

TABLE 6

IN VIVO ANTI-TUMOR STUDIES

| Example | Experiment No. | Dose (mg/kg) | Average % Tumor Inhibition |
|---|---|---|---|
| 16B | 1 | 50 p.o. | 77 |
| | 2 | 10 p.o. | 50 |
| 4 | 1 | 50 p.o. | 41 |
| | 2 | 10 p.o. | 18 |
| | 3 | 50 p.o. | 41 |
| | 4 | 10 p.o. | 14 |
| 2 | 1 | 50 p.o. | 47 |
| | 2 | 10 p.o. | 25 |
| | 3 | 50 p.o. | 52.66 |
| | 4 | 10 p.o | 31.94 |
| 1 | 1 | 50 p.o. | 38.2 |
| | 2 | 10 p.o. | 17.16 |
| | 3 | 50 p.o. | 35.4 |
| | 4 | 10 p.o. | 34.0 |
| 7 | 1 | 50 p.o. | 76.5 |
| | 2 | 10 p.o. | 35.1 |
| 11A | 1 | 50 p.o. | 63.8 |
| | 2 | 10 p.o. | 44.8 |
| 11B | 1 | 50 p.o. | 38.8 |
| | 2 | 10 p.o | 17.0 |
| 9 | 1 | 50 p.o. | 68 |
| | 2 | 10 p.o. | 19 |
| 10 | 1 | 50 po. | 77 |
| | 2 | 10 p.o. | 49 |
| 5 | 1 | 50 p.o. | 38 |
| | 2 | 10 p.o. | 24 |
| 14A | 1 | 50 p.o. | 59 |
| | 2 | 10 p.o. | 48 |
| 13 | 1 | 50 p.o. | 61 |
| | 2 | 10 p.o. | 7 |
| 12B | 1 | 50 p.o. | 83 |
| | 2 | 10 p.o. | 37.7 |
| 5 | 1 | 50 p.o. | 38 |
| | 2 | 10 p.o. | 24 |
| 7A | 1 | 50 p.o. | 55.1 |
| | 2 | 10 p.o. | 33.7 |
| 8B | 1 | 50 p.o. | 62.5 |
| | 2 | 10 p.o. | 29.2 |
| 6 | 1 | 50 p.o. | 61.2 |
| | 2 | 10 p.o. | 35.4 |
| 18 | 1 | 50 p.o. | 73 |
| | 2 | 10 p.o. | 43 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

PHARMACEUTICAL DOSAGE FORM EXAMPLES

Example A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound selected from the group consisting of:
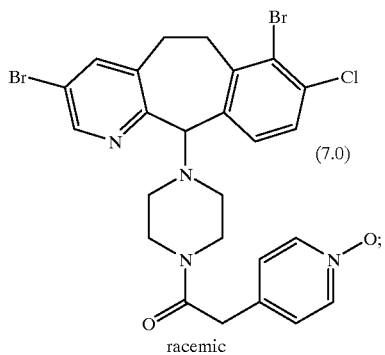
(7.0)
racemic
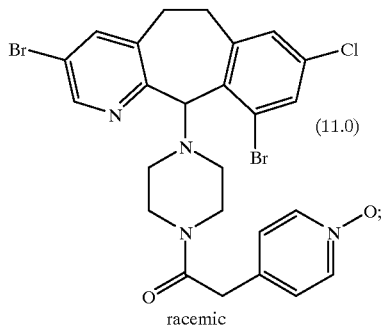
(11.0)
racemic
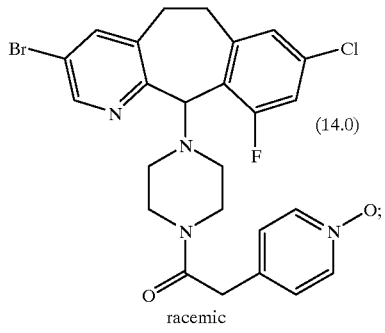
(14.0)
racemic
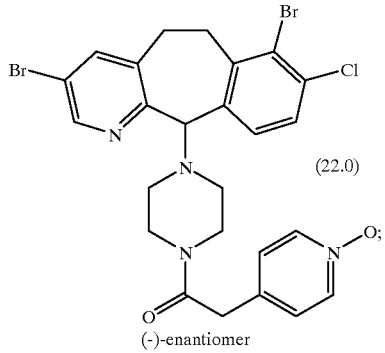
(22.0)
(−)-enantiomer
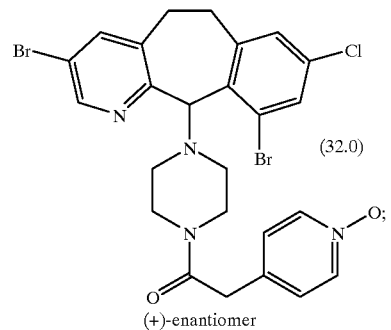
(32.0)
(+)-enantiomer
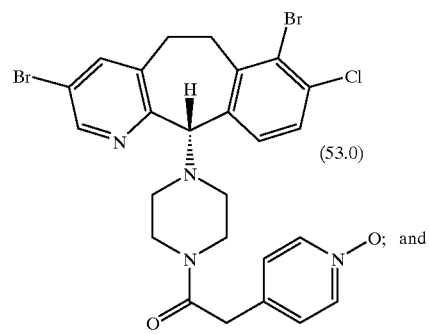
(53.0); and
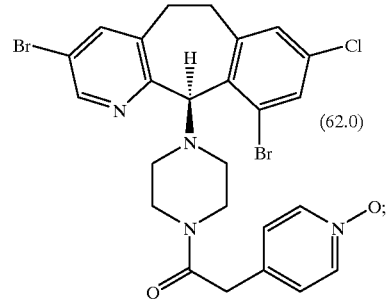
(62.0);
or pharmaceutically acceptable salts thereof.
2. The compound of claim 1 selected from the group consisting of:
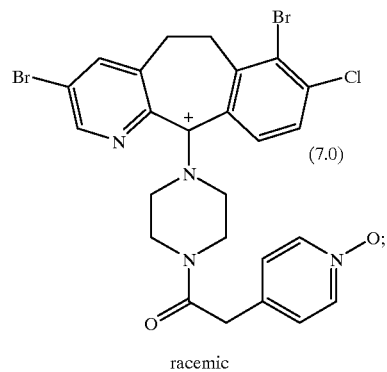
(7.0)
racemic

-continued
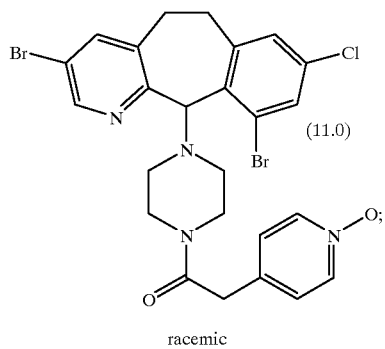
racemic
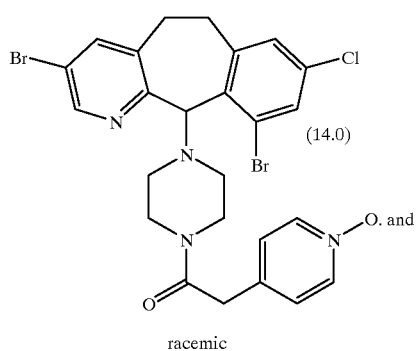
racemic
3. The compound of claim 1 selected from the group consisting of:
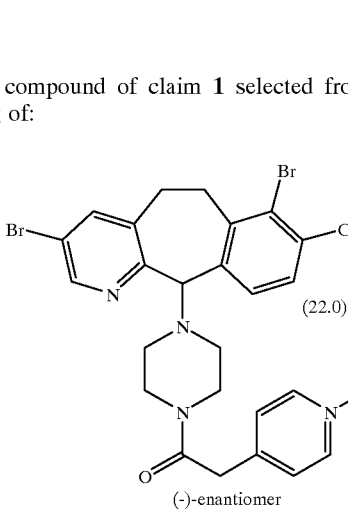
(−)-enantiomer
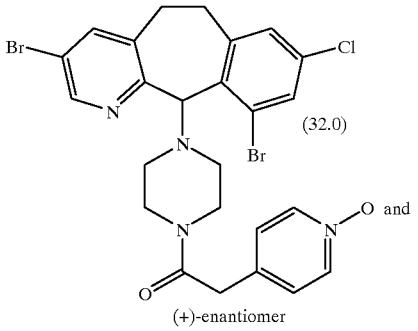
(+)-enantiomer and
4. The compound of claim 1 selected from the group consisting of:
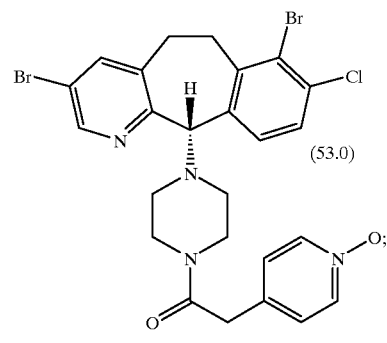
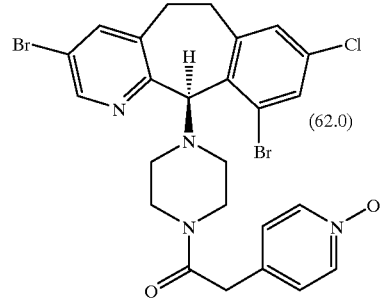
5. The compound of claim 1 having the formula:
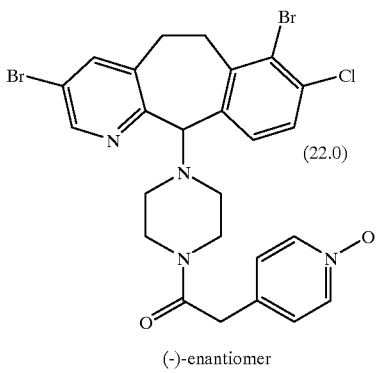
(−)-enantiomer
6. The compound of claim 1 having the formula:
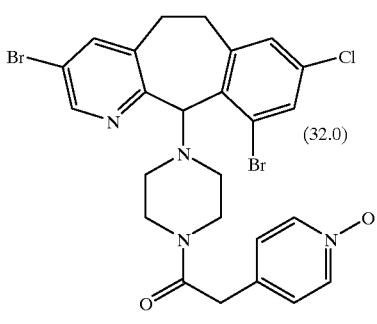
(−)-enantiomer 7. The compound of claim 1 having the formula:

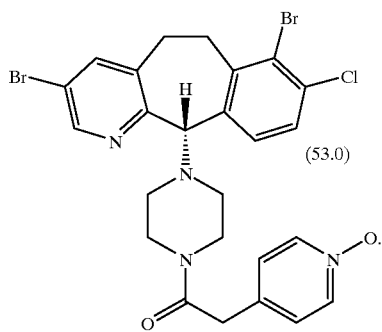

(53.0)

8. The compound of claim 1 having the formula:

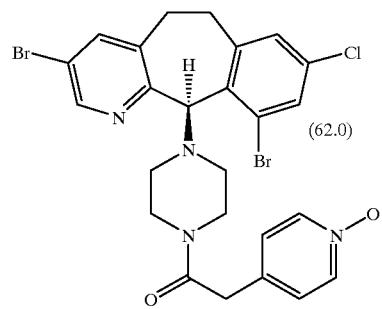

(62.0)

9. A method of inhibiting farnesyl protein transferase in tumor cells expressing an activated ras oncogene comprising administering to a human in need thereof, a farnesyl protein transferase inhibiting amount of a compound of claim 1.

10. A method of inhibiting farnesyl protein transferase comprising adminstering an effective amount of a compound of claim 1 to a human in need thereof.

11. A method of treating tumor cells wherein the cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumor cells, breast tumor cells or prostate tumor cells in a human by inhibition of farnesyl protein transferase comprising administering to a human in need thereof a compound of claim 1 in an amount that inhibits farnesyl protein transferase.

12. A pharmaceutical composition comprising an effective amount of a compound of claim 1 in combination with a pharmaceutically acceptable carrier.

* * * * *